(12) United States Patent
Hinuma et al.

(10) Patent No.: US 7,410,776 B2
(45) Date of Patent: Aug. 12, 2008

(54) POLYPEPTIDES, THEIR PRODUCTION AND USE

(75) Inventors: Shuji Hinuma, Tsukuba (JP); Kazuhiko Tatemoto, Maebashi (JP); Masaki Hosoya, Tsuchiura (JP); Yugo Habata, Tsukuba (JP); Ryo Fujii, Tsukuba (JP); Chieko Kitada, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 710 days.

(21) Appl. No.: 10/184,722

(22) Filed: Jun. 27, 2002

(65) Prior Publication Data

US 2003/0092618 A1 May 15, 2003

Related U.S. Application Data

(60) Division of application No. 09/255,518, filed on Feb. 22, 1999, now Pat. No. 6,492,324, which is a continuation of application No. PCT/JP98/05805, filed on Dec. 22, 1998.

(30) Foreign Application Priority Data

| Dec. 24, 1997 | (JP) | ................................... 9-353955 |
| Feb. 16, 1998 | (JP) | ................................ 10-032577 |
| Aug. 4, 1998 | (JP) | ................................ 10-220853 |
| Sep. 25, 1998 | (JP) | ................................ 10-271645 |

(51) Int. Cl.
*C12P 21/06* (2006.01)
*C12N 5/06* (2006.01)
*C12N 1/20* (2006.01)
*C12N 15/00* (2006.01)

(52) U.S. Cl. ................... 435/69.1; 435/326; 435/252.3; 435/320.1

(58) Field of Classification Search ........................ None
See application file for complete search history.

(56) References Cited

FOREIGN PATENT DOCUMENTS

WO   WO94/12635   6/1994

OTHER PUBLICATIONS

Abachi et al. (1995; Accession No. U26942). pp. 1-8.*
☐☐Edinger et al (1998). Journal of Virology. 72, 7934-7940.*
O'Dowd et al, (1993). Gene. 136, 355-355-360.*
Marra et al (1996; Accession No. W33327) pp. 1-2.*
Maggio et al (1999). J. Pharm. Exp. Therap. 291, 251-257.*
Tatemoto et al (1998). BBRC. 251, 471-476.*
Drolet et al (1990). Molecular Microbiology. 4, 1381-91.*
H. Choe, et al. "The Orphan Seven-Transmembrane Receptor-Apj Supports the Entry of Primary T-Cell-Line-Tropic and Dualtropic Human Immunodeficiency Virus Type 1", *Journal of Virology*, Jul. 1998, p. 6113-6118.
B. O'Dowd, et al. "A Human Gene That Shows Identity With The Gene Encoding The Angiotensin Receptor Is Located On Chromosome 11", *Gene*, 136 (1993) p. 355-360.
K. Tatemoto, et al. "Isolation and Characterization of a Novel Endogenous Peptide Ligand for the Human APJ Receptor", *Biochemical And Biophysical Research Communications*, vol. 251, No. 2, Oct. 20, 1998, p. 471-476.
T. L. Hoffman, et al. "HIV Type 1 Envelope Determinants For Use Of The CCR2b, CCR3, STRL33, and APJ Coreceptors", *Proc. Natl. Acad. Sci. USA*, vol. 95, pp. 11360-11365, Sep. 1998.
A. L. Edinger, et al. "An Orphan Seven-Transmembrane Domain Receptor Expressed Widely in the Brain Functions as a Coreceptor for Human Immunodeficiency Virus Type 1 and Simian Immunodeficiency Virus", *Journal Of Virology*, Oct. 1998, p. 7934-7940.
Y.Zhang, et al. "Use of Coreceptors Other Than CCR5 by Non-Syncytium-Inducing Adult and Pediatric Isolates of Human Immunodeficiency Virus Type 1 Is Rare In Vitro", *Journal Of Virology*, Nov. 1998, p. 9337-9344.
Database EMBL, ID MM32712 Accession No. W33327, May 16, 1996.
Stadel, J. M. et al., "Orphan G Protein-Coupled Receptors: A Neglected Opportunity For Pioneer Drug Discovery", *Trends In Pharmacological Sciences*, vol. 18, No. 11, Nov. 1, 1997, pp. 430-437.
Communication from EPO dated Jun. 26, 2003 and International Preliminary Examination Report.

* cited by examiner

*Primary Examiner*—David Romeo
*Assistant Examiner*—Steven H Standley
(74) *Attorney, Agent, or Firm*—Christine C. O'Day; David G. Conlin; Edwards Angell Palmer & Dodge, LLP

(57) ABSTRACT

This invention relates to a novel polypeptide involving in the modulation of central nervous system function, circulatory function, immune function, gastrointestinal function, metabolic function, reproductive function, etc., it can be used as a drug for treating or preventing a variety of diseases, e.g. HIV infection or AIDS (acquired immune deficiency syndrome) or the like.

4 Claims, 23 Drawing Sheets

FIG. 1

| FIG. 1A |
| FIG. 1B |
| FIG. 1C |

FIG. 1A

```
  1   GAATTCCGGGGGGTAAGCAAGAGAGGGTGGAGGAAATTCTGCAGGAGACAGGCTTC                    58
 59   CTCCAGGGTCTGGAGAACCCAGAGGCAGCTCCTCCTGAGTGCTGGGAAGGACTCTGGCA                  118
119   TCTTCAGCCCTTCTTACTCTCTGAGGCTCCTGGTGTCCCGGACCCTCGCCCTCTTCTCCACTCCCC           178
         (partial) TCTTCAGCCCTTCTTACTCTCTGAGGCTCCTGGTGTCCCGGACCCTCGCCCTCTTCTCCACTCCCC
179   GTGACAGAGACCACGGAGCCACGGAGCTGGTGATTTTGACAACTACTATGGGCAGACAACCAGTCTGAGTGT    238
239   AGCATGGAGGAAGGTGGTGATTTTGACAACTACTATGGGCAGACAACCAGTCTGAGTGT                   298
  1                  MetGluGluGlyGlyAspPheAspAsnTyrTyrGlyAlaAspAsnGlnSerGluCys     19

299   GAGTACACAGACTGGAAATCCTCGGGGCCCCTCATCCCTGCCATCTACATGTTGGTCTTC                 358
 19   GluTyrThrAspTrpLysSerSerGlyAlaLeuIleProAlaIleTyrMetLeuValPhe                  39

359   CTCCTGGGCACCACGGAAAACGGTCTCTGGACCGTGTTTCGGAGCAGCCGGGAG                       418
 39   LeuLeuGlyThrThrGlyAsnGlyLeuValLeuValLeuTrpThrValPheArgSerSerArgGlu            59

419   AAGAGGCGCTCAGCTGATATCTTCATTGCTAGCCTGGCGGTGGCTGACCTTCGTG                      478
 59   LysArgArgSerAlaAspIlePheIleAlaSerLeuAlaValAlaAspLeuThrPheVal                  79

479   GTGACGCTGCCCCTGTGGCTACCTACACGTACCGGGACTACTGACTGGCCCTTTGGGACC                 538
 79   ValThrLeuProLeuTrpLeuProThrAlaThrTyrThrTyrArgAspTyrAspTrpProPheGlyThr         99
```

| | | |
|---|---|---|
| 539 | TTCTTCTGCAAGCTCAGCAGCTACCTCATCTTCGTCAACATGTACGCCAGCGTCTTCTGC | 598 |
| 99 | PhePheCysLysLeuSerSerTyrLeuIlePheValAsnMetTyrAlaSerValPheCys | 119 |
| 599 | CTCACCGGCCTCAGCTTCGACCGCTACCTGGAGGCCAGTGGCCAATGCTCGG | 658 |
| 119 | LeuThrGlyLeuSerPheAspArgTyrLeuAlaIleValArgProValAlaAsnAlaArg | 139 |
| 659 | CTGAGGCTGCGGGTGCAGGCGGCCCTGTGCCACGGCAGTTCTTTGGTGCTGGCCGCCCTC | 718 |
| 139 | LeuArgLeuArgValSerGlyAlaValAlaThrAlaValLeuTrpValLeuAlaAlaLeu | 159 |
| 719 | CTGGCCATGCCTGTCATGGTGTTACGCACCACCGGGGACTTGGAGAACACCACTAAGGTG | 778 |
| 159 | LeuAlaMetProValMetValLeuArgThrThrGlyAspLeuGluAsnThrThrLysVal | 179 |
| 779 | CAGTGCTACATGGACTACTCCATGGTGGCCACTGTGAGCTCAGAGTGGGCCTGGGAGGTG | 838 |
| 179 | GlnCysTyrMetAspTyrSerMetValAlaThrValSerSerGluTrpAlaTrpGluVal | 199 |
| 839 | GGCCTTGGGGTCTCCGTCCACCGTGGGCTTTGTGGTGGTGCCCTTCACCATCATGCTGACC | 898 |
| 199 | GlyLeuGlyValSerThrThrValGlyPheValValProPheThrIleMetLeuThr | 219 |
| 899 | TGTTACTTCTTCATCGCCCAAACCATCGGGCTGGCCACTTCCGCAAGGAACGCATCGAGGGC | 958 |
| 219 | CysTyrPhePheIleAlaGlnThrIleAlaGlyHisPheArgLysGlyArgIleGluGly | 239 |
| 959 | CTGCGGAAGCGGCGCCGGCTGCTCAGCATCATCGTGGTGGTGACCTTTGCCCTG | 1018 |
| 239 | LeuArgLysArgArgArgLeuLeuSerIleIleValValValLeuValValThrPheAlaLeu | 259 |

FIG. 1B

```
1019  TGCTGGATGCCCTACCACCTGGTGAAGACGCTGTACATGCTGGGCAGCCTGCTGCACTGG  1078
 259  CysTrpMetProTyrHisLeuValLysThrLeuTyrMetLeuGlyLysSerLeuLeuHisTrp  279

1079  CCCTGTGACTTTGACCTTCTTCCTCATGAACATCTTCCCCTACTGCACTTGCATCAGCTAC  1138
 279  ProCysAspPheAspLeuLeuPheLeuMetAsnIlePheProTyrCysThrCysIleSerTyr  299

1139  GTCAACAGCTGCCTCAACCCCTTCCTCTTCCTATGCCTTTTTGACCCCCGCTTCCGCCAGGCC  1198
 299  ValAsnSerCysLeuAsnProPheLeuPheLeuTyrAlaPhePheAspProArgPheArgGlnAla  319

1199  TGCACCTCCATGCTCTGCTGTGCCCAGAGCAGGTGCGCAGGCACCTCCACAGCAGCAGT  1258
 319  CysThrSerMetLeuCysCysAlaGlnSerArgCysAlaGlyThrSerHisSerSerSer  339

1259  GGGGAGAAGTCAGCCAGCTACTCTTCGGGCACACAGCCAGGGCCCCCAACATGGGC  1318
 339  GlyGluLysSerAlaSerTyrSerSerGlyHisSerGlnGlyProGlyProAsnMetGly  359

1319  AAGGGTGGAGAACAGATGCACGAGAAATCCATCCCCTACAGCCAGGAGACCCTTGTGTT  1378
 359  LysGlyGlyGluGlnMetHisGluLysSerIleProTyrSerGlnGluThrLeuValVal  379

1379  GACTAGGGCTGGGAGCAGAGACAGAAGCCCTGCGGCCCTCCCCCGGCCCTTTGCCCTT  1438
 379  AspEnd***

1439  GCTTTCTGAAAATCAGGTAGTGTGGCTACTCCTGTCGTATGCACATCCTTAACTGTCC  1498
1499  CCTGATTCTGCCCCGCCCTGTCCTCCTACTGCTTTATTCTTTCTCAGAGTTTGTGGT  1558
1559  TTAGGGAAAGAGACTGGGCTCTACAGACCCTGCACAAGCCATTAATCTCACTC  1618
1619  AGCCTCAGTTTCTCCATTGGTATGGGGGAAATGCATATTGATCCTAAAATGTTGA  1678
1679  AGCCTGAGTCTGAACGCAGTAAAAGCTTGTTCCCTGCTTTCTTAGATCTGCAAT  1738
1739  CGTCTTTCCCCGGAATTC  1758
```

FIG. 1C

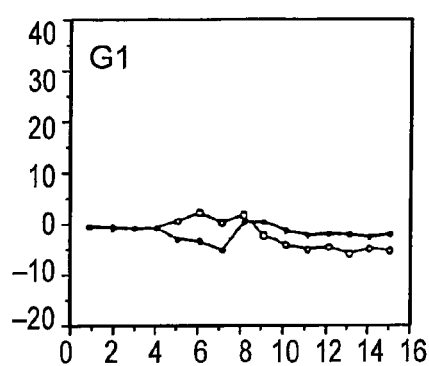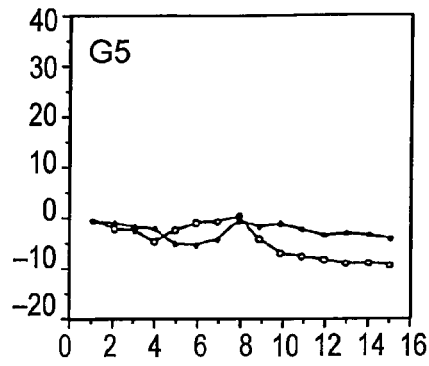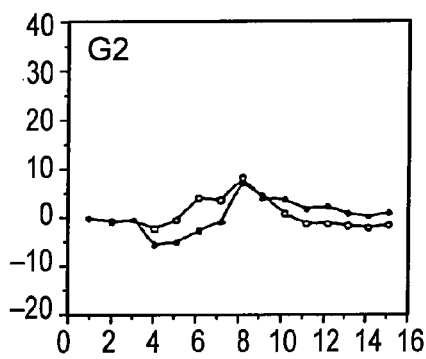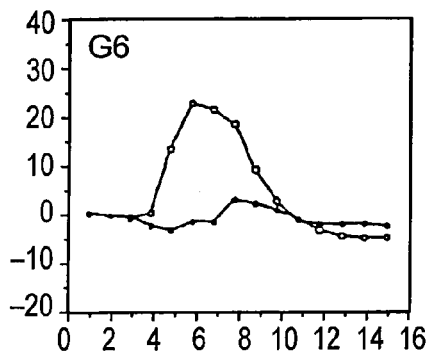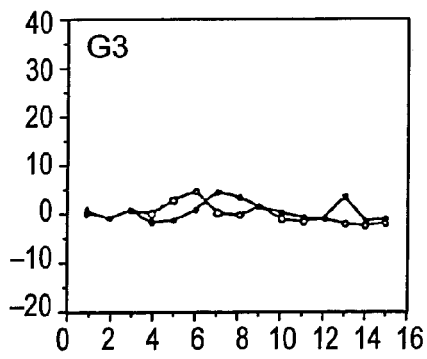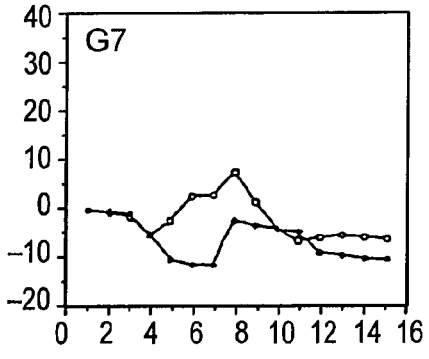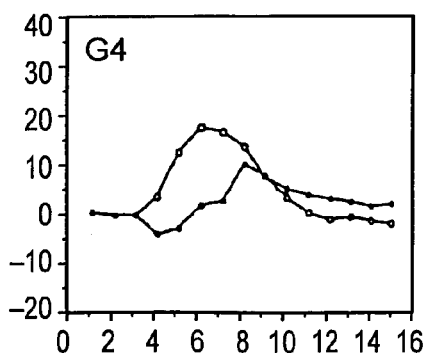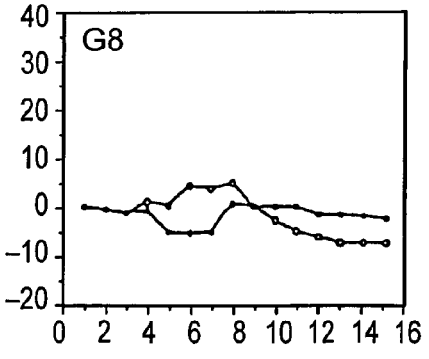
FIG. 5

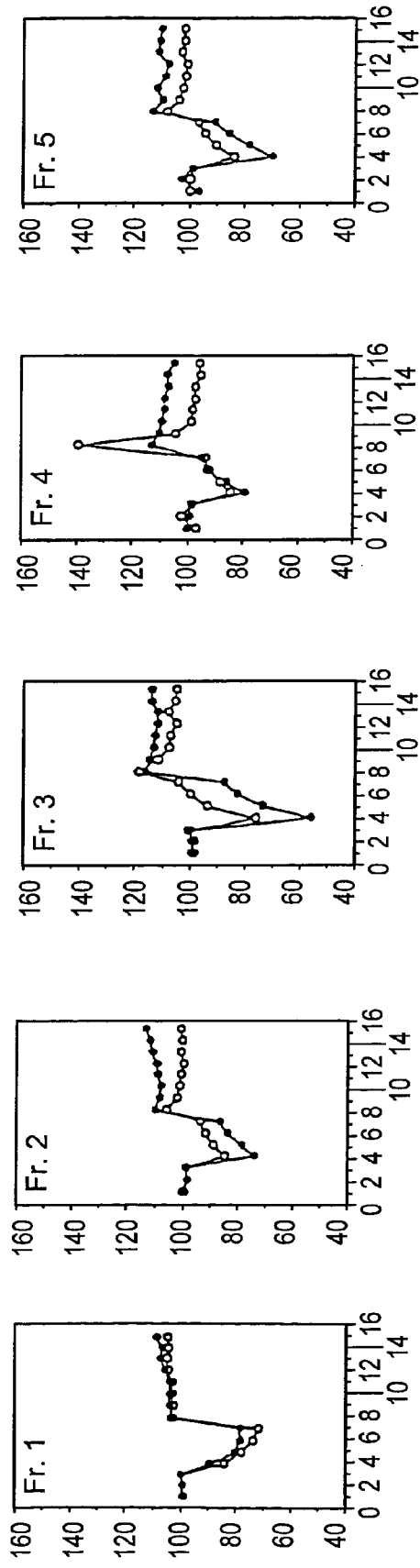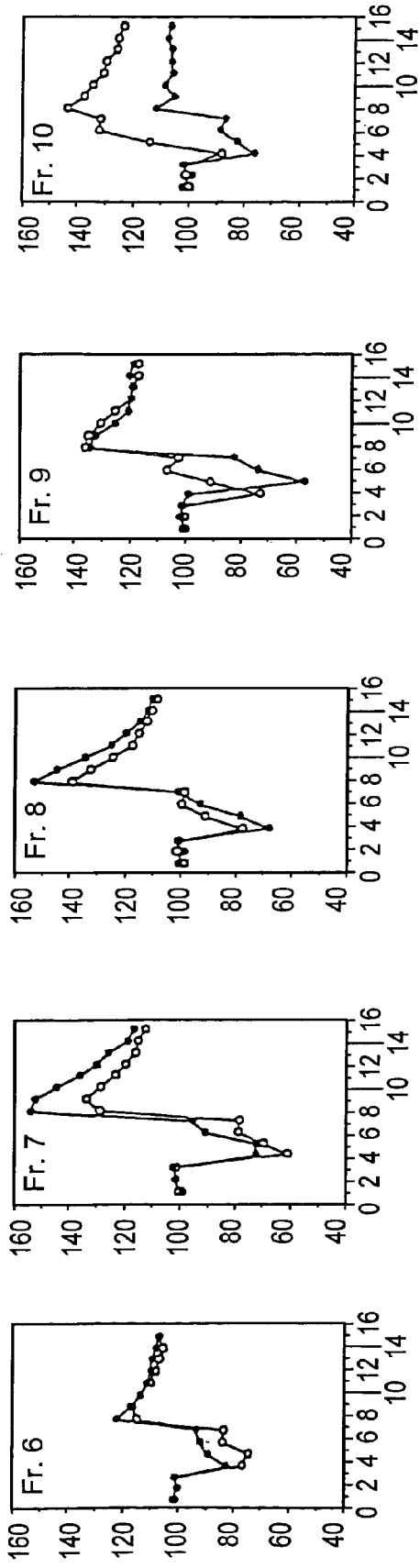
FIG. 6

Bovine | L V C P R G P R S G P P G P P W Q G G | G — Q — W — A — P — G — T | G R R K F R R Q R P R L
  1                                          17

Mouse EST    5'  GG ACT GGA CCA GGA GCC TGG CAG GGA GGC AGG AAA TTT CGC AGA CAG CGC CCC CGG CTC
                  1

S  H  K  G  P  M  P  F  *
             TCC CAT AAG GGC CCC ATG CCT TTC TAA AGC AGG ATT GAA GGG CTC GCC AAG TGC CCT CCC GGT

GCC GGT CTC TGT ACT CCA CAG ATG AAT TCT CTT C 3'
                                                         159

FIG. 14

| | | |
|---|---|---|
| 1 | CCACTTAGAGAGTTTTTGCCGCCGACCCGAAGCCACCAAGGCCAGCTTCGCGGCGCTGCC | 60 |
| 1 | | 1 |

| | | |
|---|---|---|
| 61 | CCGCGGCGGCAGAGAAGGCTGCACCAGAGCAGAGGCAGCGAGCAGGAGTGGGGCAGGCAG | 120 |
| 1 | | 1 |

| | | |
|---|---|---|
| 121 | CCAGCGGTGCGGCTGGGGCGCTCACCCTCCCGCGGTCCGGGAGCCACGCGAGCTCCGTGC | 180 |
| 1 | | 1 |

| | | |
|---|---|---|
| 181 | CCGCACGCGCCAGCCCCGGCTCGCGCCTTTCTTTGCGTCCGGGTGCCCTGCCTCTCCGCC | 240 |
| 1 | | 1 |

| | | |
|---|---|---|
| 241 | CACTCGCCGGCTCCTCTGGGCTGCCGCGGACCGAGTTGCAGCATGAATCTGAGGCTCTGC | 300 |
| 1 | MetAsnLeuArgLeuCys | 6 |

| | | |
|---|---|---|
| 301 | GTGCAGGCGCTGCTGCTGCTCTGGCTCTCCTTGACTGCAGTTTGTGGAGTGCCACTGATG | 360 |
| 7 | ValGlnAlaLeuLeuLeuLeuTrpLeuSerLeuThrAlaValCysGlyValProLeuMet | 26 |

| | | |
|---|---|---|
| 361 | TTGCCTCCAGATGGAACAGGACTAGAAGAAGGAAGCATGCGCTACCTGGTGAAGCCCAGA | 420 |
| 27 | LeuProProAspGlyThrGlyLeuGluGluGlySerMetArgTyrLeuValLysProArg | 46 |

| | | |
|---|---|---|
| 421 | ACTTCGAGGACTGGACCAGGAGCCTGGCAGGGAGGCAGGAGGAAATTTCGCAGACAGCGC | 480 |
| 47 | ThrSerArgThrGlyProGlyAlaTrpGlnGlyGlyArgArgLysPheArgArgGlnArg | 66 |

| | | |
|---|---|---|
| 481 | CCCCGGCTCTCCCATAAGGGCCCCATGCCTTTCTAAAGCAGGATTGAAGGGCTCGCCAAG | 540 |
| 67 | ProArgLeuSerHisLysGlyProMetProPhe*** | 78 |

| | | |
|---|---|---|
| 541 | TGCCCTCCCGGTGCCGGTCTCTCTACTCCACAGATGAATTCTCTTCTCTGGAACCCTCAC | 600 |
| 78 | | 78 |

| | | |
|---|---|---|
| 601 | ATCTATTTGGCTTTCATCTTGCACCTGTTCTAGCTGCTGATGGTCCCGGCTCTTCTCACC | 660 |
| 78 | | 78 |

| | | |
|---|---|---|
| 661 | CACCAAGTTCCTCTAATGGCGTG | 683 |
| 78 | | 78 |

FIG. 15

```
                       10               20            30             40            50
BOVINE PARTI    -41 .........  ..........  ..........  ..........  ..........  .LVQPRGPRS   9
MOUSE             1 MNLRLCVQAL  LLLWLSLTAV  CGVPLMLPPD  GTGLEEGSMR   YLVKPRTSRI  50

60              70            80            90            100
BOVINE PARTI     10 GPCPWQGG..  ..........  ..........  ..........  ..........  59
MOUSE            51 GPCAWQGGRR  KFRRQRPRLS  HKGPMPF*..  ..........  ..........  100
```

FIG. 16

```
  1 AGTCGACGCATGAATCTGAGTTTCTGCGTGCAGGCGCTGCTGCTGCTCTGGCTCTCCTTG  60
  1         MetAsnLeuSerPheCysValGlnAlaLeuLeuLeuLeuTrpLeuSerLeu  17

61 ACTGCCGTGTGTGGAGTGCCACTGATGCTGCCTCCAGATGGGAAAGGGCTAGAAGAAGGC 120
 18 ThrAlaValCysGlyValProLeuMetLeuProProAspGlyLysGlyLeuGluGluGly  37

121 AACATGCGCTACCTGGTGAAGCCCAGAACTTCCAGGACTGGACCAGGGGCCTGGCAGGGA 180
 38 AsnMetArgTyrLeuValLysProArgThrSerArgThrGlyProGlyAlaTrpGlnGly  57

181 GGCAGGAGGAAATTTCGCAGACAGCGGCCCCGTCTCTCCCATAAGGGACCCATGCCTTTC 240
 58 GlyArgArgLysPheArgArgGlnArgProArgLeuSerHisLysGlyProMetProPhe  77

241 TAAAGCTAGCTTGAAGGGCTC                                        261
 77 ***                                                           77
```

FIG. 17

```
  1     CCTCCCCCGCGCCGGCTCGCCGGGGCCGCGGCGGCCCAAGGAGCAGCATGAATCTGCGG  59
  1                                                      MetAsnLeuArg   4

60 CTCTGCGTGCAGGCGCTCCTGCTGCTCTGGCTCTCCTTGACCGCGGTGTGTGGAGGGTCC 119
  5 LeuCysValGlnAlaLeuLeuLeuLeuTrpLeuSerLeuThrAlaValCysGlyGlySer  24

120 CTGATGCCGCTTCCCGATGGGAATGGGCTGGAAGACGGCAATGTCCGCCACCTGGTGCAG 179
 25 LeuMetProLeuProAspGlyAsnGlyLeuGluAspGlyAsnValArgHisLeuValGln  44

180 CCCAGAGGGTCAAGGAATGGGCCAGGGCCCTGGCAGGGAGGTCGGAGGAAATTCCGCCGC 239
 45 ProArgGlySerArgAsnGlyProGlyProTrpGlnGlyGlyArgArgLysPheArgArg  64

240 CAGCGGCCCCGCCTCTCCCATAAGGGACCCATGCCTTTCTGAAGCAGGACTGAAGGGGCC 299
 65 GlnArgProArgLeuSerHisLysGlyProMetProPhe***                    77

| | | |
|---|---|---|
| 1 | ATGAATCTGCGGCGCTGCGTGCAGGCGCTCCTGCTGCTCTGGCTGTGCCTCTCTGCCGTG | 60 |
| 1 | M  N  L  R  R  C  V  Q  A  L  L  L  L  W  L  C  L  S  A  V | 20 |
| 61 | TGCGGAGGACCCCTGCTGCAGACTTCTGACGGGAAGGAGATGGAAGAAGGCACCATCCGA | 120 |
| 21 | C  G  G  P  L  L  Q  T  S  D  G  K  E  M  E  E  G  T  I  R | 40 |
| 121 | TACCTGGTGCAGCCCCGAGGCCCCAGGAGCGGGCCCCTGGCAGGGCCAGGTCGGGAGG | 180 |
| 41 | Y  L  V  Q  P  R  G  P  R  S  G  P  W  Q  G  G  R  R | 60 |
| 181 | AAGTTCCGGCGGCAGCGGCCACGCCGCCTCTCCCACAAGGGTCCCATGCCTTTCTGA | 234 |
| 61 | K  F  R  R  Q  R  P  R  L  S  H  K  G  P  M  P  F  * | 78 |

FIG. 19

```
BOVINE    1  MNLRRCVQAL LLLWLCISAV CGGSLLQTSD GKEMEEGTIR YLVQPRGPRS   50
MOUSE     1  MNLRLCVQAL LLLWLSLTAV CGVSLMLPPD GTGLEEGSMR YLVKPRTSRT   50
RAT       1  MNLSFCVQAL LLLWLSLTAV CGVSLMLPPD GKGLEEGNMR YLVKPRTSRT   50
HUMAN     1  MNLRLCVQAL LLLWLSLTAV CGGSLMPLPD GNGLECGNVR HLVQPRGSRN   50

BOVINE   51  GPGPWQGGRR KFRRQRPRLS HKGPMPF*..  ......... .........   100
MOUSE    51  GPGAWQGGRR KFRRQRPRLS HKGPMPF*..  ......... .........   100
RAT      51  GPGAWQGGRR KFRRQRPRLS HKGPMPF*..  ......... .........   100
HUMAN    51  GPGPWQGGRR KFRRQRPRLS HKGPMPF*..  ......... .........   100
```

FIG. 20

POLYPEPTIDES, THEIR PRODUCTION AND USE

CROSS-REFERENCE TO RELATED APPLICATIONS

The present application is a divisional of U.S. patent application Ser. No. 09/255,518, filed on Feb. 22, 1999, now U.S. Pat. No. 6,492,324, which is a continuation of International Application PCT/JP98/05805, filed on Dec. 22, 1998, which in turn claims priority to Japanese Application Nos.: 9-353955, filed on Dec. 24, 1997; 10-032577, filed on Feb. 16, 1998; 10-220853, filed on Aug. 4, 1998; and 10-271645, filed on Sep. 25, 1998, which are hereby incorporated by reference in their entireties.

TECHNICAL FIELD

The present invention relates to a novel ligand polypeptide for the G protein-coupled receptor protein, APJ and a DNA comprising a DNA encoding the ligand polypeptide.

BACKGROUND ART

Many hormones and neurotransmitters mediate biological functions through specific receptors present on the cell membrane. Many of these receptors engage themselves in the intracellular transduction of signals through activation of the coupled guanine nucleotide-binding protein (hereinafter sometimes referred to briefly as G protein) and have the common structure comprising 7 transmembrane domains. Therefore, these receptors are collectively referred to as G protein-coupled receptor or 7-transmembrane receptor.

Through the interaction of such hormones or neurotransmitters with G protein-coupled receptors, a variety of regulatory functions of vital importance, for example maintenance of homeostasis, reproduction, development, metabolism and growth, and regulation of the nervous system, circulatory system, immune system, gastrointestinal system and metabolic system are all discharged. While it is known, as mentioned above, that receptor proteins exist for various hormones or neurotransmitters and are playing important roles in the control of vital functions, it is still unknown in many respects whether unknown active substances (hormones or neurotransmitters) and their receptors ever exist or not.

In recent years, by taking advantage of the similarity of such G protein-coupled receptor proteins in partial amino acid sequence, searches for DNAs coding for novel receptor proteins have been undertaken by the polymerase chain reaction technique (abbreviated as PCR) and actually a large number of orphan G protein-coupled receptors, so called because their ligands are unknown, have been cloned to this day (Libert, F., et al., Science, 244, 569-572, 1989; Welch, S. K., et al., Biochem. Biophys. Res. Commun., 209, 606-613, 1995; Marchese, A., et al., Genomics, 23, 609-618, 1994; Marchese, A., Genomics, 29, 335-344, 1995). Furthermore, as the result of random sequencing of genomic DNAs and cDNAs, novel G protein-coupled receptor proteins have been discovered one after another (Nomura, N., et al., DNA Research, vol. 1, 27-35, 1994). The only general means so far available for determining the ligands to such orphan G protein-coupled receptor proteins is a mere estimation based on the similarity in primary structure among G protein-coupled receptor proteins. However, many orphan G protein-coupled receptor proteins have low homology with known receptors and it is, therefore, difficult to estimate their ligands based on the similarity in primary structure alone except in those cases where they are actually subtypes of receptors for known ligands. On the other hand, since many orphan G protein-coupled receptors have been discovered as the result of gene analysis, it is supposed that there still exist many unknown corresponding ligands. However, only in a few cases, ligands have actually been identified for such orphan G protein-coupled receptors.

Recently, investigation for novel opioid peptides by introducing a cDNA coding for a receptor protein which a ligand is unknown, i.e. an orphan G protein-coupled receptor protein, into animal cells have been reported (Reinsheid, R. K. et al., Science, 270, 792-794, 1995, Menular, J.-C., et al., Nature 377, 532-535, 1995). However, in view of similarities to known G protein-coupled receptor proteins and tissue distributions, it could be easily anticipated in these cases that the ligand would be belonging to the family of opioid peptides. The history of research and development in the realm of substances acting on the living body through the opioid receptor dates back to many years ago and various antagonists and agonists have been developed. Therefore, among the compounds artificially synthesized, an agonist of the receptor was picked out and, using it as a probe, expression of the receptor in the receptor cDNA-transfected cells was verified. Then, a search was made for an activator of the intracellular signal transduction which was similar to the agonist, the activator so found was purified, and the structure of the ligand was determined. However, when the homology of an orphan receptor to known G protein-coupled receptor proteins is low, it was very difficult to predict its ligand.

APJ is one of the orphan G protein-coupled receptors so far reported (O'Dowd, B. F., et al., Gene, 436, 355-359, 1993). APJ has low homology with an angiotensin receptor (AT1) but its ligand has remained unknown since no reaction was detected at all with angiotensin II despite the expression of APJ in CHO cells.

Ligands for APJ, which is an orphan G protein-coupled receptor expressed in the central nervous system, circulatory system, reproductive system, immune system, digestive organs and so forth, are expected to be useful as drugs but their structure and functions have not been elucidated as yet.

DISCLOSURE OF INVENSION

Employing a cell in which a cDNA coding for orphan G protein-coupled receptor protein (APJ) has been expressed by a suitable means and using measurement of a specific cell stimulation activity exemplified by a signal transduction activity as an indicator, the inventors of the present invention succeeded in screening for a polypeptide which said receptor protein recognizes as a ligand.

Furthermore, the inventors found that a compound can be screened which is capable of changing the binding activity of this ligand which is an activating factor to said receptor protein.

The present invention, therefore, relates to (1) a polypeptide capable of binding to a receptor protein which comprises an amino acid sequence represented by SEQ ID NO:3 or a substantial equivalent thereto, a precursor polypeptide thereof, its amide or ester, or a salt thereof, (2) a polypeptide as mentioned in the above (1), which comprises an amino acid sequence represented by SEQ ID NO:1 or a substantial equivalent thereto, (3) a polypeptide as mentioned in the above (1), which comprises a partial sequence of the amino acid sequence represented by SEQ ID NO:15, 38, 40 or 42, (4) a polypeptide as mentioned in the above item (1), which comprises
(a) a peptide comprising the 6th to 77th amino acid residues of the amino acid sequence represented by SEQ ID NO:15, 38, 40 or 42,
(b) a peptide comprising the 40th to 77th amino acid residues of the amino acid sequence represented by SEQ ID NO:15, 38, 40 or 42,
(c) a peptide comprising the 42nd to 77th amino acid residues of the amino acid sequence represented by SEQ ID NO:15, 38, 40 or 42,
(d) a peptide comprising the 47th to 77th amino acid residues of the amino acid sequence represented by SEQ ID NO:15, 38, 40 or 42,
(e) a peptide comprising the 61st to 77th amino acid residues of the amino acid sequence represented by SEQ ID NO:15, 38, 40 or 42,
(f) a peptide comprising the 65th to 77th amino acid residues of the amino acid sequence represented by SEQ ID NO:15, 38, 40 or 42, or a derivative thereof resulting from conversion of the N-terminal amino acid (Gln) to a pyroglutamic acid residue,
(g) a peptide comprising the 1st to 25th amino acid residues of the amino acid sequence represented by SEQ ID NO:15, 38, 40 or 42,
(h) a peptide comprising the 6th to 25th amino acid residues of the amino acid sequence represented by SEQ ID NO:15, 38, 40 or 42,
(i) a peptide comprising the 42nd to 64th amino acid residues of the amino acid sequence represented by SEQ ID NO:15, 38, 40 or 42,
(j) a peptide comprising the 61st to 64th amino acid residues of the amino acid sequence represented by SEQ ID NO:15, 38, 40 or 42,
(k) a peptide comprising the 43rd to 77th amino acid residues of the amino acid sequence represented by SEQ ID NO:15, 38, 40 or 42,
(l) a peptide comprising the 41st to 77th amino acid residues of the amino acid sequence represented by SEQ ID NO:15, 38, 40 or 42,
(m) a peptide comprising the 66th to 77th amino acid residues of the amino acid sequence represented by SEQ ID NO:15, 38, 40 or 42,
(n) a peptide comprising the 67th to 77th amino acid residues of the amino acid sequence represented by SEQ ID NO:15, 38, 40 or 42,
(o) a peptide comprising the 64th to 77th amino acid residues of the amino acid sequence represented by SEQ ID NO:15, 38, 40 or 42,
(p) a peptide comprising the 63rd to 77th amino acid residues of the amino acid sequence represented by SEQ ID NO:15, 38, 40 or 42,
(q) a peptide comprising the 65th to 76th amino acid residues of the amino acid sequence represented by SEQ ID NO:15, 38, 40 or 42,
(r) a peptide comprising the 65th to 75th amino acid residues of the amino acid sequence represented by SEQ ID NO:15, 38, 40 or 42, or
(s) a peptide comprising the 65th to 75th amino acid residues of the amino acid sequence represented by SEQ ID NO:15, 38, 40 or 42,
(5) a polypeptide as mentioned in the above (1) which comprises an amino acid sequence of from the 65th amino acid residue to the 77th amino acid residue of the amino acid sequence represented by SEQ ID NO:15, SEQ ID NO:38, SEQ ID NO:40 or SEQ ID NO:42,
(6) a polypeptide as mentioned in the above (1) which has the amino acid sequence: pGlu Arg Pro Arg Leu Ser His Lys Gly Pro Met Pro Phe,
(7) a polypeptide as mentioned in the above (1) which comprises an amino acid sequence of from the 42nd amino acid residue to the 77th amino acid residue of the amino acid sequence represented by SEQ ID NO:15, SEQ ID NO:38, SEQ ID NO:40 or SEQ ID NO:42,
(8) a polypeptide as mentioned in the above (1) which is a precursor polypeptide having an amino acid sequence represented by SEQ ID NO:15 or a substantial equivalent thereto,
(9) a polypeptide as mentioned in the above (1) which is a precursor polypeptide having an amino acid sequence represented by SEQ ID NO:38 or a substantial equivalent thereto,
(10) a polypeptide as mentioned in the above (1) which is a precursor polypeptide having an amino acid sequence represented by SEQ ID NO:40 or a substantial equivalent thereto,
(11) a polypeptide as mentioned in the above (1) which is a precursor polypeptide having an amino acid sequence represented by SEQ ID NO:42 or a substantial equivalent thereto,
(12) a DNA which comprises a DNA having a nucleotide sequence coding for a polypeptide capable of binding to a receptor protein which comprises an amino acid sequence represented by SEQ ID NO:3 or a substantial equivalent thereto, or a precursor polypeptide thereof,
(13) a DNA as mentioned in the above (12) wherein the polypeptide encoded thereby comprises an amino acid sequence represented by SEQ ID NO:1 or a substantial equivalent thereto,
(14) a DNA as mentioned in the above (12) wherein the polypeptide encoded thereby comprises an amino acid sequence of from the 65th amino acid residue to the 77th amino acid residue of the amino acid sequence represented by SEQ ID NO:15, SEQ ID NO:38, SEQ ID NO:40 or SEQ ID NO:42,
(15) a DNA as mentioned in the above (12) wherein the polypeptide encoded thereby comprises an amino acid sequence of from the 42nd amino acid residue to the 77th amino acid residue of the amino acid sequence represented by SEQ ID NO:15, SEQ ID NO:38, SEQ ID NO:40 or SEQ ID NO:42,
(16) a DNA as mentioned in the above (12) wherein the precursor polypeptide encoded thereby comprises an amino acid sequence represented by SEQ ID NO:15 or a substantial equivalent thereto,
(17) a DNA as mentioned in the above (12) wherein the precursor polypeptide encoded thereby comprises an amino acid sequence represented by SEQ ID NO:38 or a substantial equivalent thereto,
(18) a DNA as mentioned in the above (12) wherein the precursor polypeptide encoded thereby comprises an amino acid sequence represented by SEQ ID NO:40 or a substantial equivalent thereto,
(19) a DNA as mentioned in the above (12) wherein the precursor polypeptide encoded thereby comprises an amino acid sequence represented by SEQ ID NO:42 or a substantial equivalent thereto,
(20) a recombinant vector which comprises the DNA as mentioned in the above (12),
(21) a transformant carrying the DNA as mentioned in the above (12) or the recombinant vector as mentioned in the above (20),

(22) a method for producing a polypeptide, a precursor polypeptide thereof or a salt thereof which comprises cultivating the transformant as mentioned in the above (21),

(23) a pharmaceutical composition which comprises the polypeptide, the precursor polypeptide thereof, its amide or ester, or a salt thereof as mentioned in the above (1),

(24) a pharmaceutical composition which comprises the DNA as mentioned in the above (12),

(25) a pharmaceutical composition as mentioned in the above (23) or (24) which is a central nervous system function modulator, a circulatory function modulator, an immune function modulator, a gastrointestinal function modulator, a metabolic function modulator or a reproductive function modulator,

(26) an antibody against the polypeptide or the precursor polypeptide thereof as mentioned in the above (1),

(27) a diagonostic composition which comprises the antibody as mentioned in the above (26), and

(28) a method for screening for a compound changing binding activity of the polypeptide as mentioned in the above (1) to a receptor protein which comprises an amino acid sequence represented by SEQ ID NO:3, which comprises using the polypeptide as mentioned in the above (1) and said receptor protein, The present invention further provides:

(29) a polypeptide as mentioned in the above (1) which is of mammalian origin, and

(30) a pharmaceutical composition as mentioned in the above (23) or (24) which is an agent for the treatment and/or prevention of dementia, depression, hyperactive child syndrome (microencephalopathy), disturbance of consciousness, anxiety disorder, schizophrenia, phobia, growth hormone secretory disorder, hyperphagia, polyphagia, hypercholesterolemia, hyperglyceridemia, hyperlipemia, hyperprolactinemia, diabetes mellitus, cancer, pancreatitis, diseases of kidney, Turner's syndrome, neurosis, rheumatoid arthritis, spinal injury, transient brain ischemia, amyotrophic lateral sclerosis, acute myocardial infarction, spinocerebellar degeneration, bone fracture, wounds, atopic dermatitis, osteoporosis, asthma, epilepsy, sterility, arteriosclerosis, pulmonary emphysema, pulmonary edema, galactorrhea, AIDS, or the like.

In the practice of the present invention, the G protein-coupled receptor protein for the ligand polypeptide is specifically:

(31) a G protein-coupled receptor protein characterized by containing an amino acid sequence represented by SEQ ID NO:3, or a substantial equivalent thereto, or a salt thereof, or

(32) a G protein-coupled receptor protein as mentioned in the above (31) which comprises an amino acid sequence derived from the amino acid sequence represented by SEQ ID NO:3 by deletion of 1 to 30, preferably 1 to 10 amino acid residues therefrom, by addition (or insertion) of 1 to 30, preferably 1 to 10 amino acid residues thereto (or thereinto), or by substitution of 1 to 30, preferably 1 to 10 amino acid residues with a different amino acid residue or residues, or a salt thereof, for instance.

In the present specification, the term "substantial equivalent(s)" means that the activity of the protein, e.g., nature of the binding activity of the ligand and the receptor and physical characteristics are substantially the same. Substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

BRIEF DESCRIPTION OF THE DRAWINGS

FIG. 1 shows the nucleotide sequence (SEQ ID NO: 4) of the G protein-coupled receptor protein (APJ) cDNA and the amino acid sequence (SEQ ID NO: 3) encoded thereby.

Figure 2:
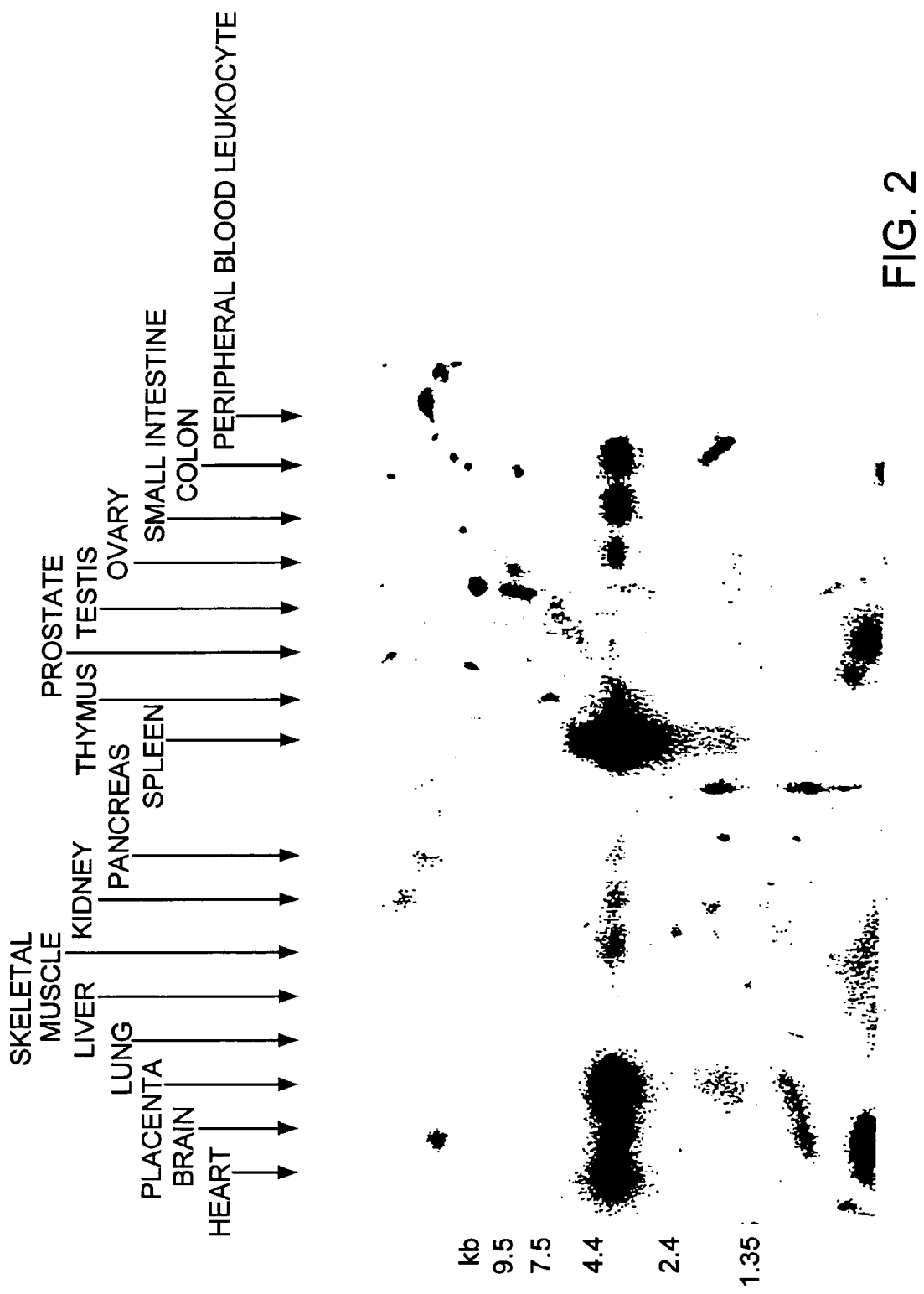
FIG. 2 shows the results of analysis for the tissue distribution of the G protein-coupled receptor protein (APJ) mRNA by Northern blotting.

Lanes 1 to 7 are for serial dilutions (1, 1/4, 1/16, 1/256, 1/1024, 1/4096) of the plasmid DNA (pAKKO-A10); lanes 8 to 11 are for serial dilutions (1, 1/10, 1/100, 1/1000) of the cDNA prepared from CHO-A10 cells; lane 12 is for the case in which no reverse transcriptase was added; lane 13 is for the case in which mRNA to serve as a template was not used; lane 14 is for the case in which control CHO cells were treated in the same manner; and lane 15 is for the case in which control CHO cells were treated in the same manner except that no reverse transcriptase was used. M stands for a DNA size marker; the left one is a StyI digest of the λ phage DNA and the right one is a HincII digest of the φχ174 DNA.

Figure 4:
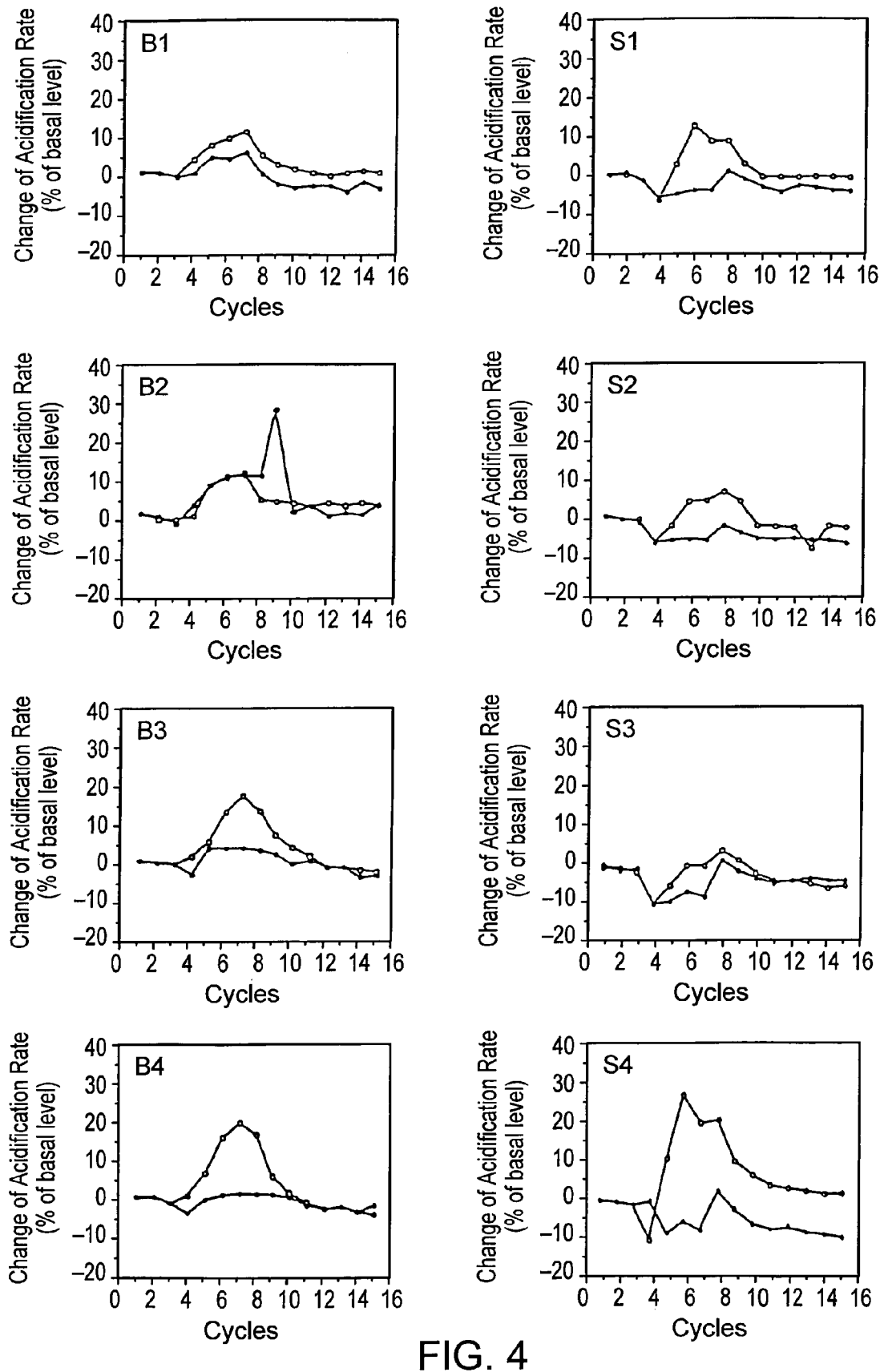

FIG. 4 shows the results of detection of the activity specifically stimulating CHO-A10 cells as contained in the swine brain or bovine stomach extract using Cytosensor.

B1 to B4 represent the measurement results obtained with the samples prepared from swine brain, and S1 to S4 the results obtained with the bovine stomach-derived samples. Each data represents the rate of change, relative to the basal level, in extracellular pH (acidification rate) in each measurement cycle between CHO-A10 cells (○) and control cells (●), as a function of time.

Cells were exposed to the sample during cycles 4 to 7.

FIG. 5 shows the results of detection of the activity specifically stimulating CHO-A10 cells as contained in the swine small intestine extract using the cytosensor (continued on FIG. 6).

G1 to G8 represent the measurement results obtained with the samples prepared from swine small intestine. Each data represents the rate of change, relative to the basal level, in extracellular pH (acidification rate) in each measurement cycle between CHO-A10 cells (○) and control cells (●), as a function of time.

Cells were exposed to the sample during cycles 4 to 7.

Figure 7:
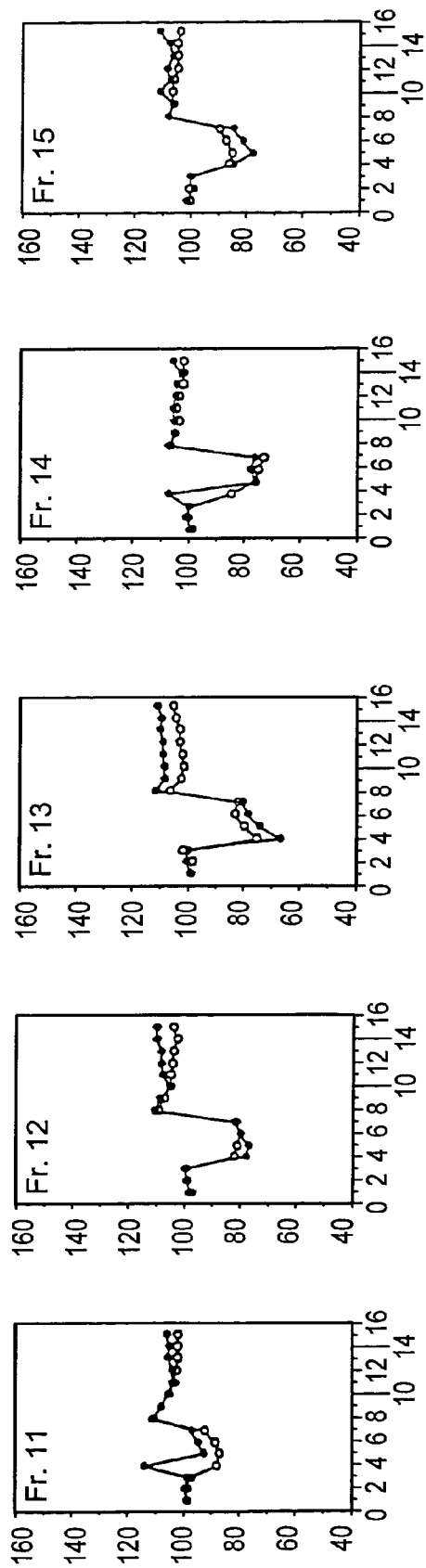

FIG. 6 shows the results of detection of the activity specifically stimulating CHO-A10 cells as contained in the bovine hypothalamus extract using Cytosensor (continued on FIG. 7).

F1 to F5 represent samples from a 10% acetonitrile eluate fraction from the C18 column, F6 to F10 samples from a 30% acetonitrile eluate fraction, and F11 to F15 samples from a 50% acetonitrile eluate fraction. Each of the fractions was further fractionated on a CM-Sepharose ion exchange column into the first effluent fraction (Fr. 1, 6, 11), a 100 mM ammonium acetate eluate fraction (Fr. 2, 7, 12), a 250 mM ammonium acetate eluate fraction (Fr. 3, 8, 13), a 500 mM ammonium acetate eluate fraction (Fr. 4, 9, 14) and a 1,000 mM ammonium acetate eluate fraction (Fr. 5, 10, 15) to give a total of 15 fractions, and the cell stimulating activity contained in each sample was measured.

Each data represents the rate of change, relative to the basal level, in extracellular pH as found when CHO-A10 cells (○) and control cells (●) were exposed to the sample during cycles 4 to 7, as a function of time.

The ordinate denotes the acidification rate (% of basal level) and the abscissa denotes the cycle.

FIG. 7 shows the results of detection of the activity specifically stimulating CHO-A10 cells as contained in the bovine hypothalamus extract using Cytosensor (continued from FIG. 6).

F1 to F5 represent samples from a 10% acetonitrile eluate fraction from the C18 column, F6 to F10 samples from a 30% acetonitrile eluate fraction, and F11 to F15 samples from a 50% acetonitrile eluate fraction. Each of the fractions was further fractionated on a CM-Sepharose ion exchange column into the first effluent fraction (Fr. 1, 6, 11), a 100 mM ammonium acetate eluate fraction (Fr. 2, 7, 12), a 250 mM ammonium acetate eluate fraction (Fr. 3, 8, 13), a 500 mM ammonium acetate eluate fraction (Fr. 4, 9, 14) and a 1,000 mM ammonium acetate eluate fraction (Fr. 5, 10, 15) to give a total of 15 fractions, and the cell stimulating activity contained in each sample was measured.

Each of the data represents the rate of change, relative to the basal level, in extracellular pH as found when CHO-A10 cells (○) and control cells (●) were exposed to the sample during cycles 4 to 7, as a function of time.

The ordinate denotes the acidification rate (% of basal level) and the abscissa denotes the cycle.

Figure 8:
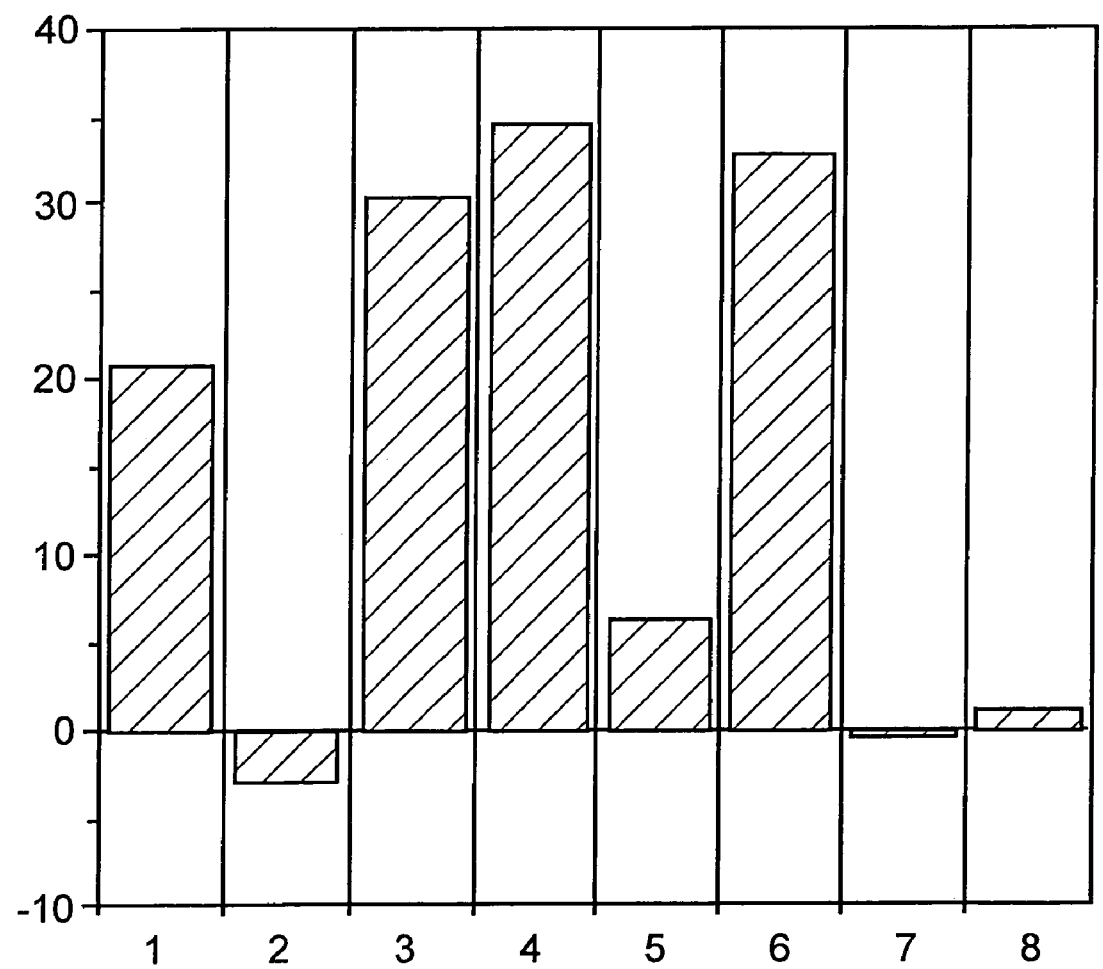

FIG. 8 illustrates the selection of high-level APJ receptor expression cells with the intensity of cell stimulating activity as an indicator Cells 1 to 8 cloned from CHO-A10 cells were exposed to the same sample and then the rate (%), relative to the basal level, of the extracellular pH change in the 4th cycle was determined and shown.

The ordinate denotes the change of acidification rate (% of basal level) and the abscissa denotes the reference number of cells cloned from CHO-A10 cells.

Figure 9:
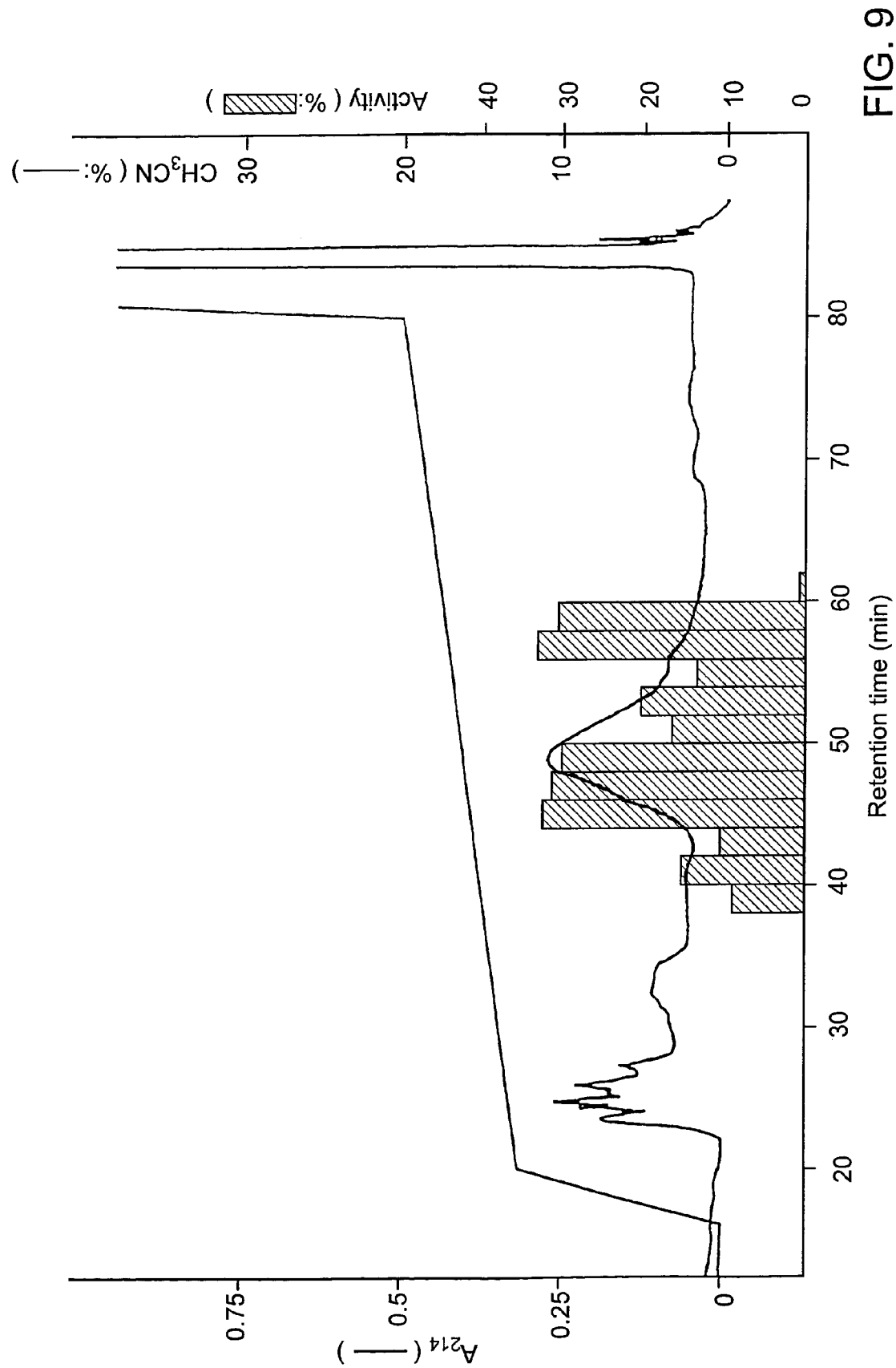

FIG. 9 shows the pattern of separation of the crude bovine stomach-derived peptide fraction in RESOURCE RPC and the detection of a CHO-A10-specific activity.

Figure 10:
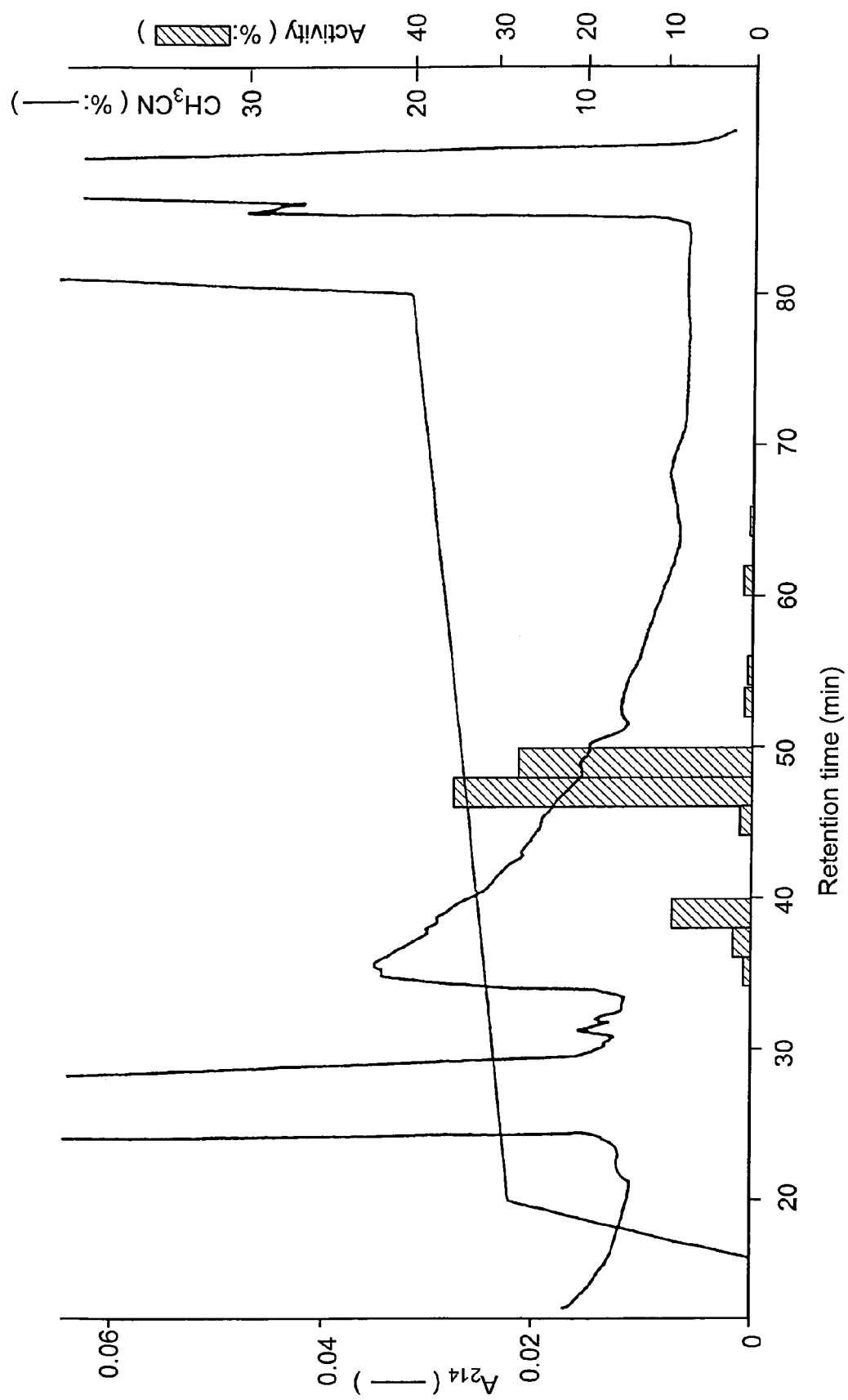

FIG. 10 shows the pattern of separation, on Vydac diphenyl 219TP5415, of the P-2 activity obtained in RESOURCE RPC and the detection of a CHO-A10-specific activity.

Figure 11:
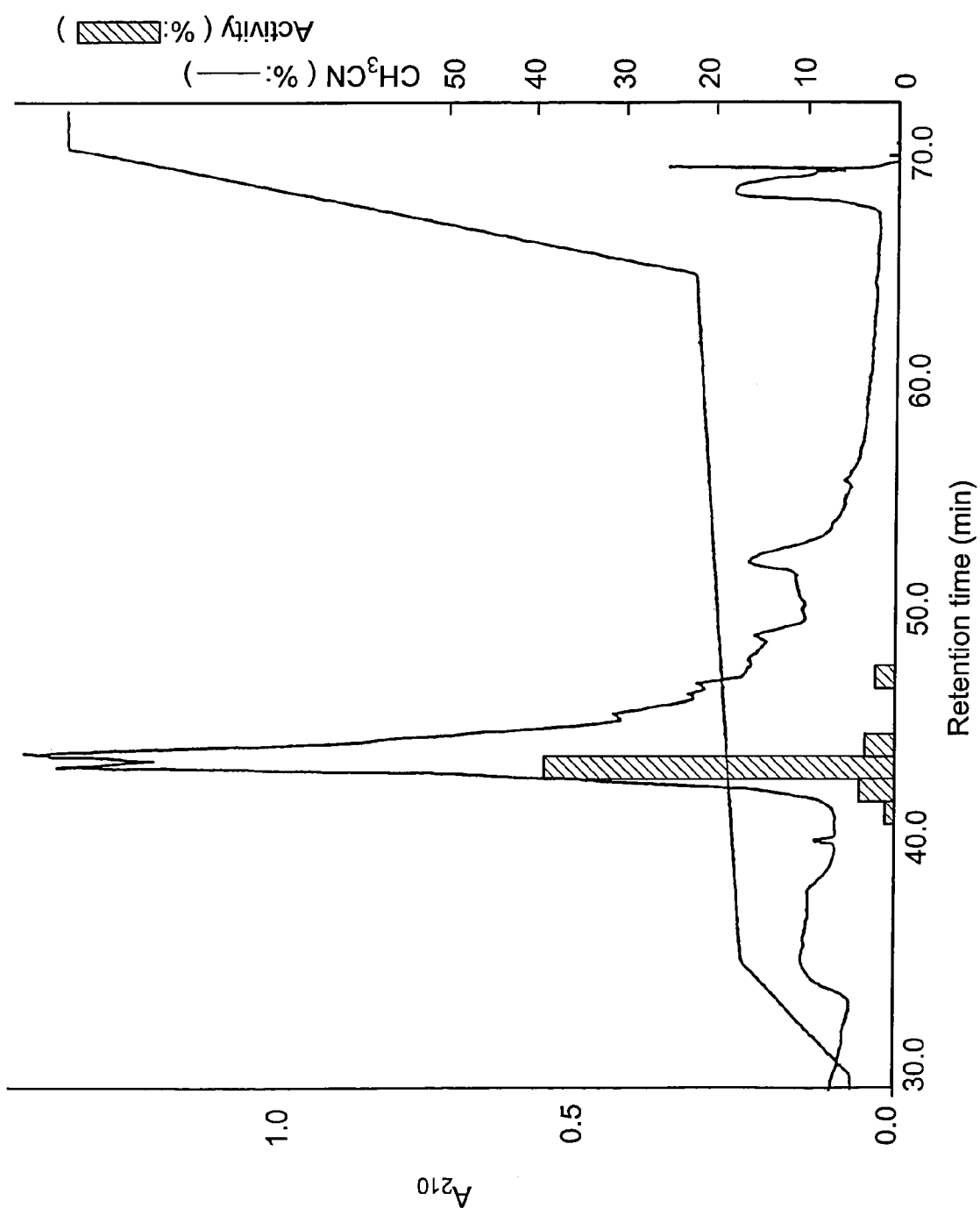

FIG. 11 shows the pattern of separation, on Sephasil C8 SC 2.1/10, of the P-2 activity obtained in RESOURCE RPC and the detection of a CHO-A10-specific activity.

Figure 12:
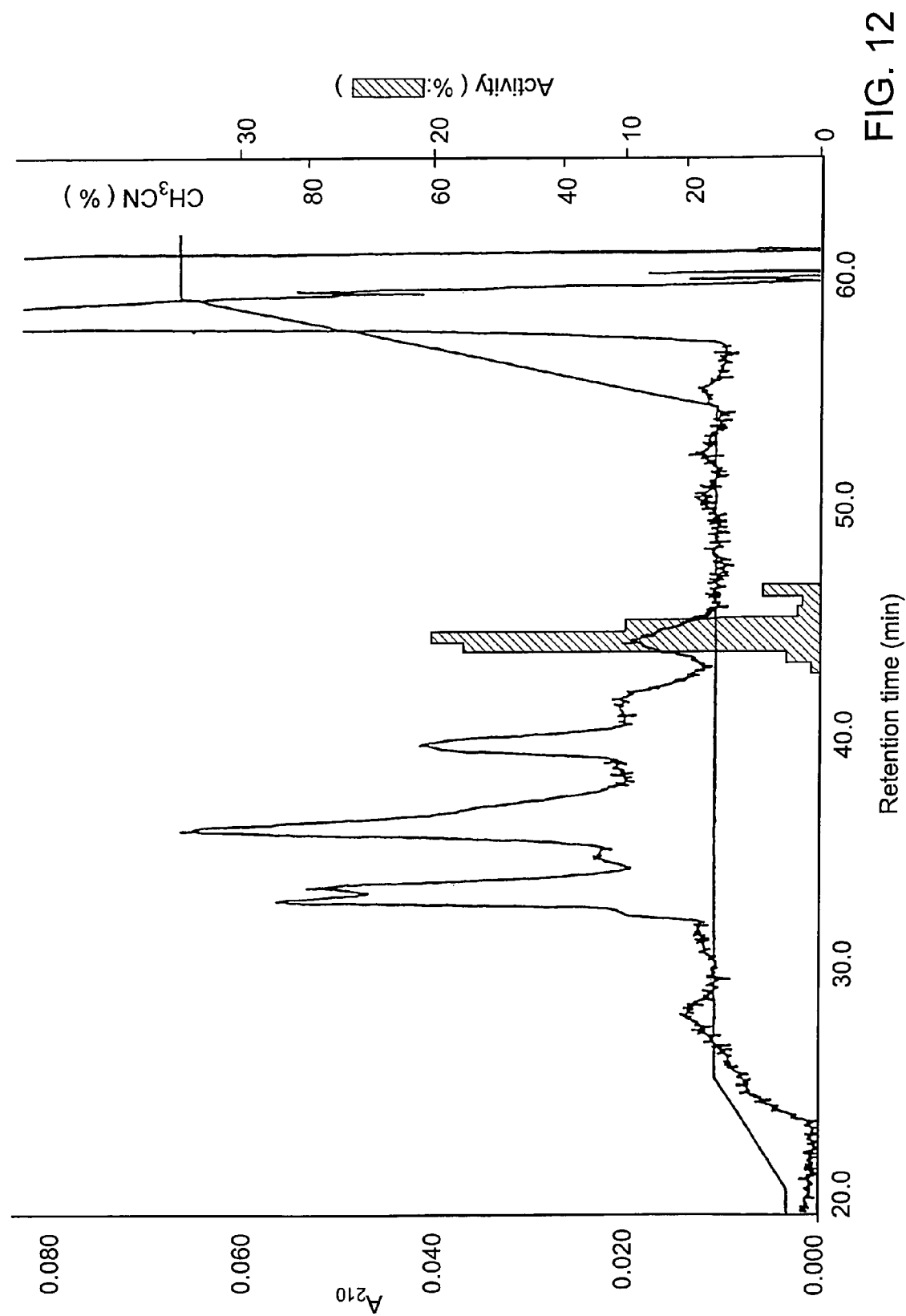

FIG. 12 shows the pattern of separation, on µ RPC C2/C18 SC 2.1/10, of the active fraction obtained on Vydac diphenyl 219TP5415 and the detection of a CHO-A10-specific activity.

Figure 13:
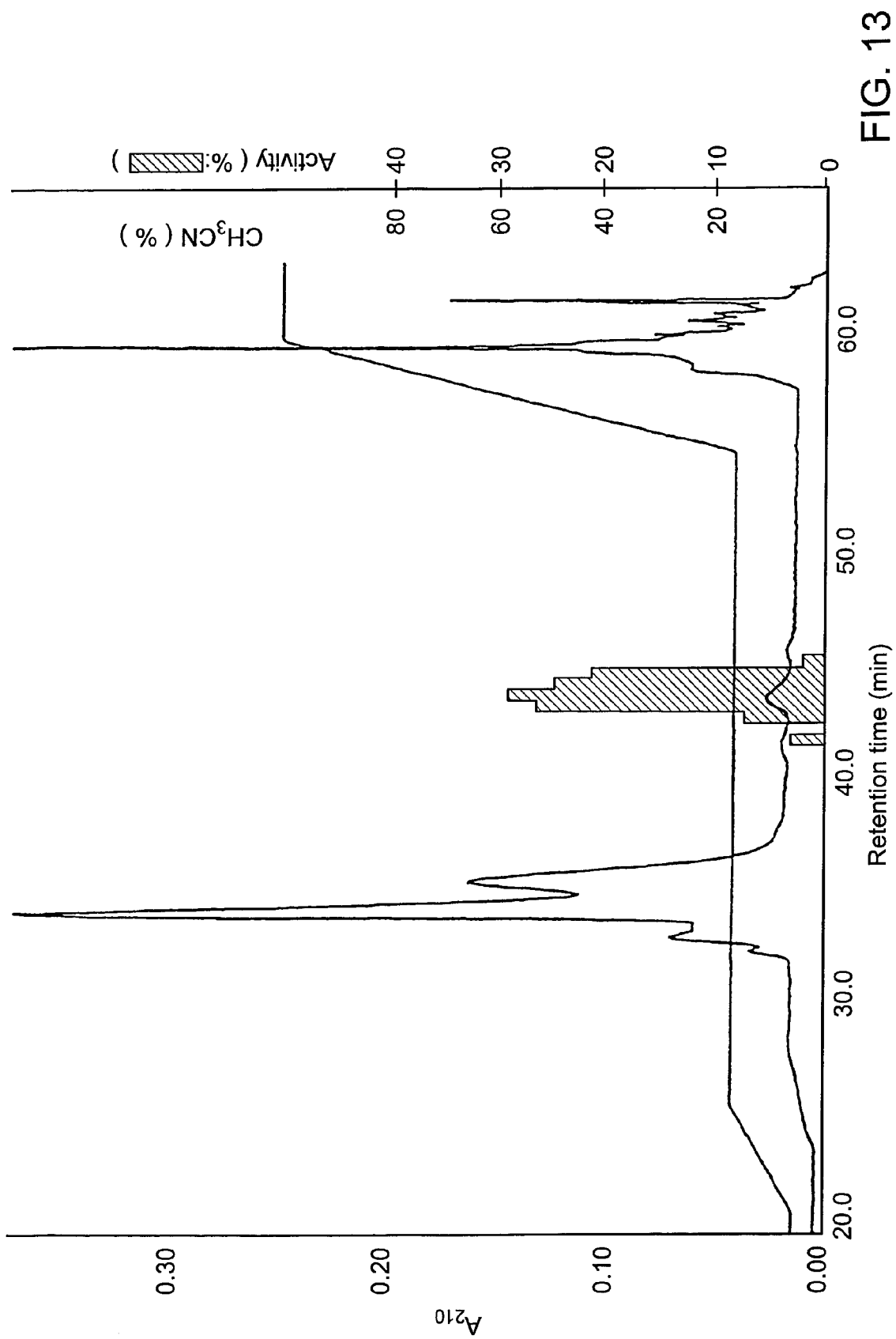

FIG. 13 shows the pattern of separation, on µ RPC C2/C18 SC 2.1/10, of the active fraction obtained on Sephasil C8 SC 2.1/10 and the detection of a CHO-A10-specific activity.

FIG. 14 shows the homology between the mouse-derived EST (Mouse EST) (pieces of SEQ ID NOS 15 & 16 respectively) and the bovine stomach-derived peptide fragment defined under SEQ ID NO:1 (Bovine).

FIG. 15 shows the nucleotide sequence (SEQ ID NO: 16) of the mouse type ligand polypeptide cDNA and the amino acid sequence (SEQ ID NO: 15) encoded thereby.

FIG. 16 shows the homology between the mouse type ligand polypeptide (SEQ ID NO: 15) (mouse) and the bovine stomach-derived peptide fragment defined under SEQ ID NO:1 (Bovine parti).

FIG. 17 shows the nucleotide sequence (SEQ ID NO: 39) of the rat type ligand polypeptide cDNA and the amino acid sequence (SEQ ID NO: 38) encoded thereby.

FIG. 18 shows the nucleotide sequence (SEQ ID NO: 41) of the human type ligand polypeptide cDNA and the amino acid sequence (SEQ ID NO: 40) encoded thereby.

FIG. 19 shows the nucleotide sequence (SEQ ID NO: 43) of the bovine type ligand polypeptide cDNA and the amino acid sequence (SEQ ID NO: 42) encoded thereby.

FIG. 20 comparatively shows the amino acid sequences (SEQ ID NOS: 42, 15, 38, 40 respectively, in order of appearance) encoded by the nucleotide sequences of the bovine, mouse, rat and human type ligand polypeptide cDNAs.

Figure 21:
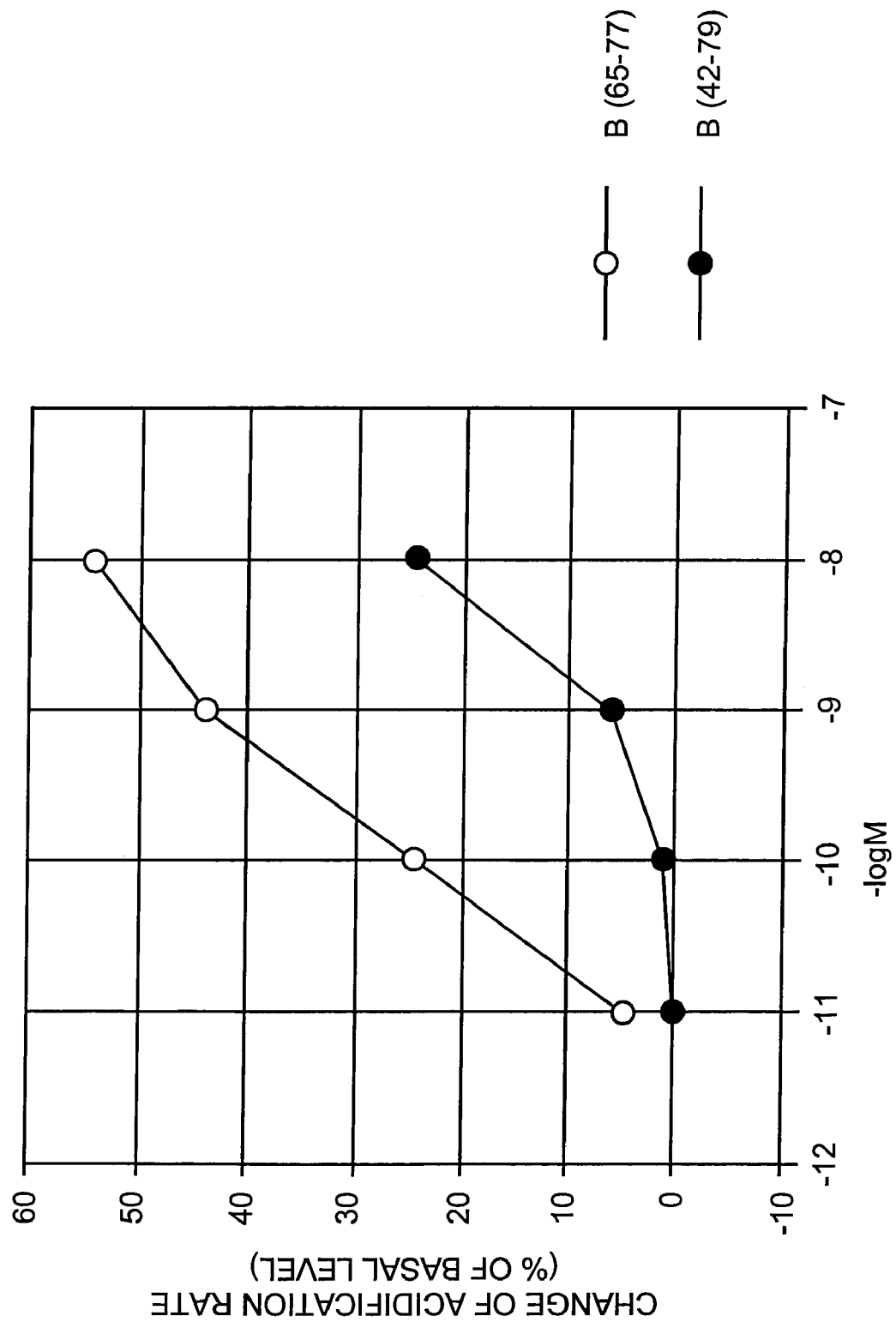

FIG. 21 graphically shows the changes in acidification rate caused by the peptide obtained in Example 16 and the peptide represented by the amino acid sequence from the 42nd to 77th amino acid residues of the sequence defined under SEQ ID NO:42.

In the figure, ○-○ represents the changes in acidification rate as caused by the peptide obtained in Example 6 while ●-● represents the changes in acidification rate as caused by the peptide represented by the amino acid sequence from the 42nd to 77th amino acid residues of the sequence defined under SEQ ID NO:42.

Figure 22:
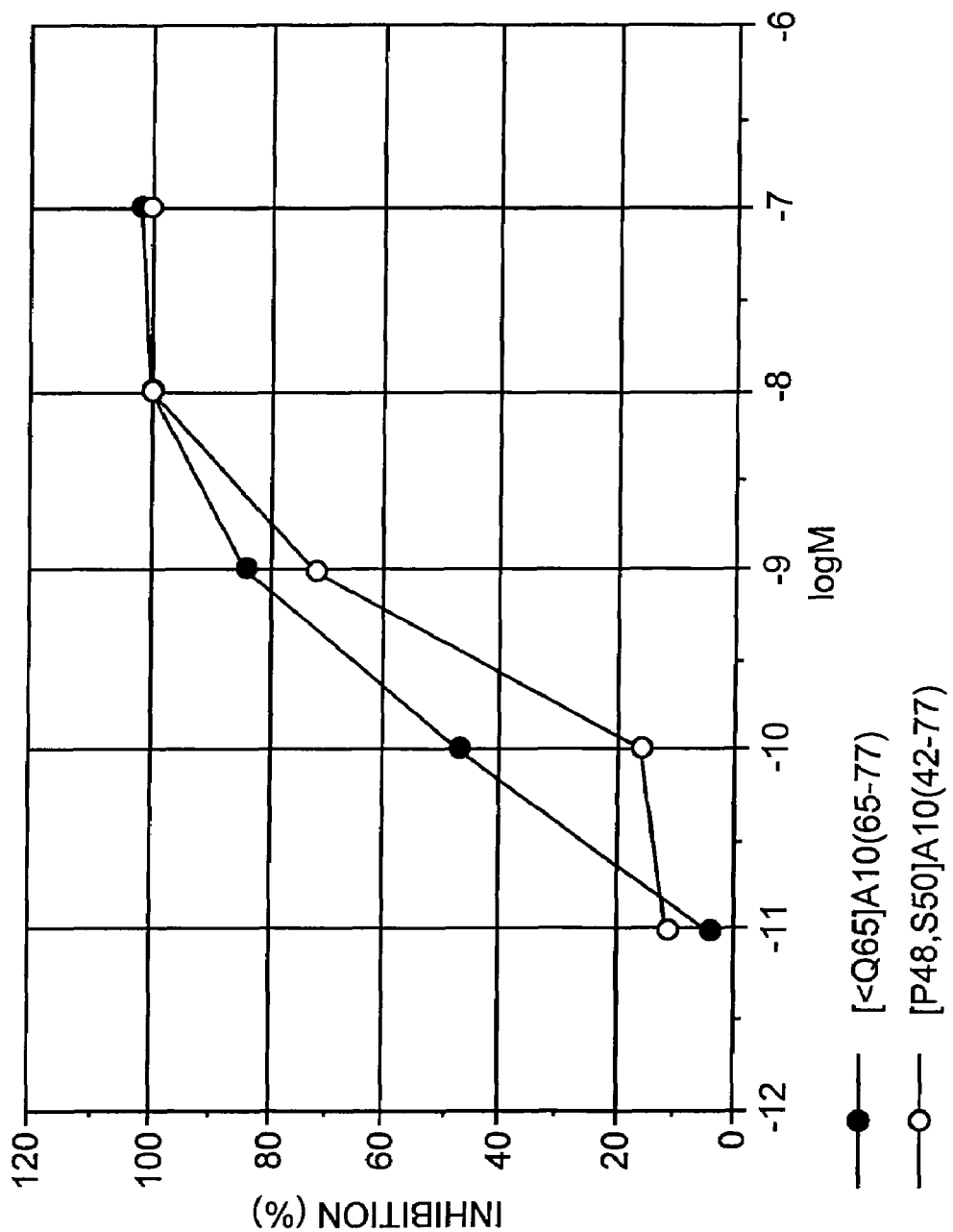

FIG. 22 graphically shows the result of the assaying of inhibitory activity against forskolin-stimulated cAMP production in Example 33.

In the figure, ○-○ represents the peptide represented by the amino acid sequence from the 42nd to 77th amino acid residues of the sequence defined under SEQ ID NO:42 while ●-● represents the peptide represented by the amino acid sequence from the 45th to 77th amino acid residues of the sequence defined under SEQ ID NO:40.

BEST MODES FOR CARRYING OUT THE INVENTION

The ligand polypeptide of the present invention includes any polypeptide capable of binding to the G protein-coupled receptor protein (APJ). Specifically, there may be mentioned polypeptides comprising ① a peptide comprising an amino acid sequence represented by SEQ ID NO:1 or a substantial equivalent thereto or a partial peptide thereof, ② a partial peptide derived from a precursor comprising an amino acid sequence represented by SEQ ID NO:15 or a substantial equivalent thereto, ③ a partial peptide derived from a precursor comprising an amino acid sequence represented by SEQ ID NO:38 or a substantial equivalent thereto, ④ a partial peptide derived from a precursor comprising an amino acid sequence represented by SEQ ID NO:40 or a substantial equivalent thereto, or ⑤ a partial peptide derived from a precursor comprising an amino acid sequence represented by SEQ ID NO:42 or a substantial equivalent thereto, among others.

The above ligand polypeptide, its amide or ester, or a salt thereof (hereinafter sometimes referred to briefly as the polypeptide), processes for their production, and uses for the polypeptide are now described in detail.

The above ligand polypeptide of the present invention includes any polypeptides derived from any tissues, e.g. pituitary gland, pancreas, brain, kidney, liver, gonad, thyroid gland, gall bladder, bone marrow, adrenal gland, skin, muscle, lung, digestive canal, blood vessel, heart, etc.; or cells of man and other warm-blooded animals, e.g. guinea pig, rat, mouse, swine, sheep, bovine, monkey, etc. and comprising ① a peptide comprising an amino acid sequence represented by SEQ ID NO:1 or a substantial equivalent thereto or a partial peptide thereof, ② a partial peptide derived from a precursor comprising an amino acid sequence represented by SEQ ID NO:15 or a substantial equivalent thereto, ③ a partial peptide derived from a precursor comprising an amino acid sequence represented by SEQ ID NO:38 or a substantial equivalent thereto, ④ a partial peptide derived from a precursor comprising an amino acid sequence represented by SEQ ID NO:40 or a substantial equivalent thereto, or ⑤ a partial peptide derived from a precursor comprising an amino acid sequence represented by SEQ ID NO:42 or a substantial equivalent thereto, among others. For example, in addition to the polypeptide comprising the amino acid sequence of SEQ ID NO:1, the ligand polypeptide of the present invention includes ① a polypeptide comprising an amino acid sequence having a homology of about 50-99.9%, preferably 70-99.9%, more preferably 80-99.9% and especially preferably 90-99.9% to the amino acid sequence of SEQ ID NO:1 and having qualitatively substantially equivalent activity to the polypeptide comprising the amino acid sequence of SEQ ID NO:73, ② a polypeptide having qualitatively substantially equivalent acitvity to the partial peptide of the precursor comprising the amino acid sequence of SEQ ID NO:15, ③ a polypeptide having qualitatively substantially equivalent acitvity to the partial peptide of the precursor comprising the amino acid sequence of SED ID NO:38, ④ a polypeptide having qualitatively substantially equivalent activity to the partial peptide of the precursor comprising the amino acid sequence of SED ID NO:40, or ⑤ a polypeptide having qualitatively substntially equivalent acitvity to the partial peptide of the precursor comprising the amino acid sequence of SED ID NO:42, etc. The term "substantially equivalent" means the nature of the receptor-binding activity, signal transduction activity and the like is equivalent. Thus, it is allowable that even differences among grades such as the strength of receptor binding activity and the molecular weight of the polypeptide are present.

As specific examples of the polypeptide of the present invention, there may be mentioned polypeptides derived from mouse brain, rat brain, swine brain, swine small intestine, bovine hypothalamus, bovine stomach, human hypothalamus or human lung and comprising an amino acid sequence represented by ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42, or the like.

Furthermore, polypeptides comprising amino acid sequences derived from a polypeptide comprising ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42, or a substantial equivalent thereto or the like, or a partial peptide thereof, by substitution, deletion, addition or insertion of one or more of amino acids may be mentioned as polypeptides containing an amino acid sequence substantial equivalent(s) in the above sense. Thus, for example, there may be mentioned polypeptides comprising (1) an amino acid sequence derived from ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, or ⑤ a partial sequence of the amino acid sequence represented by SEQ ID NO:42, by deletion of 1 to 7, preferably 1 to 5, more preferably 1 to 3 amino acids, (2) an amino acid sequence derived from ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, or ⑤ a partial sequence of the amino acid sequence represented by SEQ ID NO:42, by addition (or insertion) of 1 to 20, preferably 1 to 15, more preferably 1 to 10 amino acids, or (3) an amino acid sequence derived from ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, or ⑤ a partial sequence of the amino acid sequence represented by SEQ ID NO:42, by substitution of 1 to 7, preferably 1 to 5, more preferably 1 to 3 amino acids with other amino acids.

Furthermore, the polypeptide or the partial peptide of the present invention includes those derived by in vivo cleavage of the N terminus side of Gln, followed by conversion of said Gln to a pyroglutamic acid residue.

The precursor of the present invention may be any protein containing the ligand peptide of the invention as a partial sequence. Thus, it includes proteins containing the amino acid sequence represented by SEQ ID NO:15, 38, 40 or 42 (such a protein is hereinafter sometimes referred to, together with the ligand polypeptide mentioned above, as the polypeptide or ligand polypeptide of the invention).

The polypeptide of the invention has a molecular mass of about 1,000 to 10,000 daltons, preferably about 1,000 to about 5,000 daltons, more preferably about 1,000 to about 3,000 daltons.

In the present specification, the (poly)peptide is shown, according to established practice, with the N terminus (amino terminus) at left and the C terminus (carboxyl terminus) at right. Those polypeptides which comprises ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42 or the like generally has a carboxyl group (—COOH) or a carboxylate group (—COO⁻) at the C terminus. The C terminus may be an amide (—$CONH_2$) or an ester (—COOR) form, however. As R of the ester, there may be mentioned $C_{1-6}$ alkyl groups such as methyl, ethyl, n-propyl, isopropyl, n-butyl, etc., $C_{3-8}$ cycloalkyl groups such as cyclopentyl, cyclohexyl, etc., $C_{6-12}$ aryl groups such as phenyl, α-naphthyl, etc., $C_{7-14}$ aralkyl groups, for example phenyl-$C_{1-2}$ alkyl groups such as benzyl, phenethyl, benzhydryl, etc., and α-naphthyl-$C_{1-2}$ alkyl groups such as α-naphthylmethyl etc. Mention may also be made of pivaloyloxymethyl ester and the like, which are commonly used as esters for oral administration. When those polypeptides which comprises ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42 or the like have additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

The salt of the polypeptide of the invention is a physiologically acceptable salt with a base (e.g. alkali metal) or acid (organic acid, inorganic acid), preferably a physiologically acceptable acid addition salt. As such salt, use may be made of salts with inorganic acids (e.g. hydrochloric acid, phosphoric acid, hydrobromic acid, sulfuric acid) or organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The polypeptide of the invention can be produced by purifying a polypeptide from a human or warm-blooded animal tissue or cells, or according to the method of polypeptide synthesis mentioned later herein. It can also be produced by cultivating a transformant containing a DNA coding for the polypeptide, as mentioned later herein.

When it is produced from a human or warm-blooded animal tissue or cells, the human or warm-blooded animal tissue or cells are first homogenized and then extracted with an acid, for instance, and, for purification and isolation, the extract is subjected to salting out, dialysis, gel filtration, chromatography such as reversed phase chromatography, ion exchange chromatography or affinity chromatography, etc., in an appropriate combination.

As mentioned above, the polypeptide in the present invention can be produced by the per se known procedures for peptide synthesis. The methods for peptide synthesis may be any of a solid-phase synthesis and a liquid-phase synthesis. Thus, the objective peptide can be produced by condensing a partial peptide or amino acid capable of constituting the protein with the residual part thereof and, when the product has a protective group, the protective group is detached whereupon a desired peptide can be manufactured. The known methods for condensation and deprotection includes the procedures described in the following literature (1)-(5).
(1) M. Bodanszky and M. A. Ondetti, Peptide Synthesis, Interscience Publishers, New York, 1966
(2) Schroeder and Luebke, The Peptide, Academic Press, New York, 1965
(3) Nobuo Izumiya et al., Fundamentals and Experiments in Peptide Synthesis, Maruzen, 1975
(4) Haruaki Yajima and Shumpei Sakakibara, Biochemical Experiment Series 1, Protein Chemistry IV, 205, 1977
(5) Haruaki Yajima (ed.), Development of Drugs-Continued, 14, Peptide Synthesis, Hirokawa Shoten After the reaction, the protein can be purified and isolated by a combination of conventional purification techniques such as solvent extraction, column chromatography, liquid chromatography, and recrystallization. Where the protein isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl) phenoxy resin, 4-(2',4'-dimethoxyphenyl-Fmoc aminoethyl) phenoxy resin, and so on. Using such a resin, amino acids whose a-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, di-sulfide bonds are formed to obtain the objective polypeptide.

For the condensation of the above-mentioned protected amino acids, a variety of activating reagents for peptide synthesis can be used but a carbodiimide compound is particularly suitable. The carbodiimide includes DCC, N,N'-diisopropylcarbodiimide, and N-ethyl-N'-(3-dimethylaminoprolyl)carbodiimide. For activation with such a reagent, a racemization inhibitor additive, e.g. HOBt and the protected amino acid are directly added to the resin or the protected amino acid pre-activated as symmetric acid anhydride, HOBt ester, or HOOBt ester is added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned. The reaction temperature can be selected from the range hitherto-known to be useful for peptide bond formation and is usually selected from the range of about $-20°$ C.-$50°$ C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl-Z, Br-Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{7-14}$ aralkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl.

The protective group for the phenolic hydroxyl group of tyrosine includes Bzl, $Cl_2$-Bzl, 2-nitrobenzyl, Br-Z, and tertiary-butyl.

The protecting group of imidazole for histidine includes Tos, 4-methoxy-2,3,6-trimethylbenzenesulfonyl, DNP, benzyloxymethyl, Bum, Boc, Trt, and Fmoc.

The activated carboxyl group of the starting amino acid includes the corresponding acid anhydride, azide, and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C. -40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the α-carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide.

To obtain an ester of the polypeptide, the α-carboxyl group of the C-terminal amino acid is condensed with a desired alcohol to give an amino acid ester and then, the procedure described above for production of the amide is followed.

The polypeptide of the invention may be any peptide provided that it is substantially the same in activity (e.g. central nervous system function modulating activity, circulatory function modulating activity, immune function modulating activity, gastrointestinal function modulating activity, metabolic function modulating activity or reproductive function modulating activity) as a polypeptide comprising ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42, or the like. As such peptide, there may be mentioned peptides comprising an amino acid sequence derived from ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42, or the like by deletion of 1 or more amino acids. Specifically, preferred are (1) a peptide comprising the 1st to 12th amino acid residues of the amino acid sequence represented by SEQ ID NO:1, (2) a peptide comprising the 1st to 13th amino acid residues of the amino acid sequence represented by SEQ ID NO:1, (3) a peptide comprising the 1st to 14th amino acid residues of the amino acid sequence represented by SEQ ID NO:1, (4) a peptide comprising the 1st to 15th amino acid residues of the amino acid sequence represented by SEQ ID NO:1, (5) a peptide comprising the 1st to 16th amino acid residues of the amino acid sequence represented by SEQ ID NO:1, (6) a peptide comprising a partial sequence of the amino acid sequence represented by SEQ ID NO:15, 38, 40 or 42, and the like. Among them, a peptide comprising a partial sequence of the amino acid sequence represented by SEQ ID NO:15, 38, 40 or 42, is preferable.

As specific examples of the polypeptide comprising a partial sequence of the amino acid sequence represented by SEQ ID NO:15, 38, 40 or 42, there may be mentioned:

(a) a peptide comprising the 6th to 77th amino acid residues of the amino acid sequence represented by SEQ ID NO:15, 38, 40 or 42, (b) a peptide comprising the 40th to 77th amino acid residues of the amino acid sequence represented by SEQ ID NO:15, 38, 40 or 42, (c) a peptide comprising the 42nd to 77th amino acid residues of the amino acid sequence represented by SEQ ID NO:15, 38, 40 or 42, (d) a peptide comprising the 47th to 77th amino acid residues of the amino acid sequence represented by SEQ ID NO:15, 38, 40 or 42, (e) a peptide comprising the 61st to 77th amino acid residues of the amino acid sequence represented by SEQ ID NO:15, 38, 40 or 42, (f) a peptide comprising the 65th to 77th amino acid residues of the amino acid sequence represented by SEQ ID NO:15, 38, 40 or 42, or a derivative thereof resulting from conversion of the N-terminal amino acid (Gln) to a pyroglutamic acid residue, (g) a peptide comprising the 1st to 25th amino acid residues of the amino acid sequence represented by SEQ ID NO:15, 38, 40 or 42, (h) a peptide comprising the 6th to 25th amino acid residues of the amino acid sequence represented by SEQ ID NO:15, 38, 40 or 42, (i) a peptide comprising the 42nd to 64th amino acid residues of the amino acid sequence represented by SEQ ID NO:15, 38, 40 or 42, (j) a peptide comprising the 61st to 64th amino acid residues of the amino acid sequence represented by SEQ ID NO:15, 38, 40 or 42, (k) a peptide comprising the 43rd to 77th amino acid residues of the amino acid sequence represented by SEQ ID NO:15, 38, 40 or 42, (l) a peptide comprising the 41st to 77th amino acid residues of the amino acid sequence represented by SEQ ID NO:15, 38, 40 or 42, (m) a peptide comprising the 66th to 77th amino acid residues of the amino acid sequence represented by SEQ ID NO:15, 38, 40 or 42, (n) a peptide comprising the 67th to 77th amino acid residues of the amino acid sequence represented by SEQ ID NO:15, 38, 40 or 42, (o) a peptide comprising the 64th to 77th amino acid residues of the amino acid sequence represented by SEQ ID NO:15, 38, 40 or 42, (p) a peptide comprising the 63rd to 77th amino acid residues of the amino acid sequence represented by SEQ ID NO:15, 38, 40 or 42, (q) a peptide comprising the 65th to 76th amino acid residues of the amino acid sequence represented by SEQ ID NO:15, 38, 40 or 42, (r) a peptide comprising the 65th to 75th amino acid residues of the amino acid sequence represented by SEQ ID NO:15, 38, 40 or 42, (s) a peptide comprising the 65th to 75th amino acid residues of the amino acid sequence represented by SEQ ID NO:15, 38, 40 or 42, and so on. Preferred among these are a peptide comprising the 65th to 77th amino acid residues of the amino acid sequence represented by defined under SEQ ID NO:15, 38, 40 or 42, a derivative thereof resulting from conversion of the N-terminal amino acid (Gln) to a pyroglutamic acid residue or a peptide comprising the 42nd to 77th amino acid residens of the amino acid sequence represented by SEQ ID NO:15, 38, 40 or 42. Particularly preferred are the peptide comprising the 65th to the 77th amino acid residue of the amino acid sequence represented by SEQ ID NO:15, 38, 40 or 42 and the derivative thereof resulting from conversion of the N-terminal amino acid (Gln) to a pyroglutamic acid residue (pGlu Arg Pro Arg Leu Ser His Lys Gly Pro Met Pro Phe). In addition, a partial peptide of the peptide represented by the amino acid sequence: pGlu Arg Pro Arg Leu Ser His Lys Gly Pro Met Pro Phe, can also be used as a polypeptide (peptide) of the invention.

The polypeptide of the invention can further be used as an antigen for the production of anti-ligand polypeptide antibodies. In addition to the above-mentioned polypeptide of the invention, partial peptides, such as N-terminal peptides, C-terminal peptides and intermediate peptides, derived from the above-mentioned polypeptide of the invention, can also be used as the antigen.

The partial peptides which can be used may be peptides each containing only one domain or peptides each containing a plurality of domains.

The partial peptide in this specification may have a C terminus in the form of an amide (—CONH$_2$) or an ester (—COOR). As examples of the ester group, there may be mentioned those mentioned above for the polypeptide. When said fragment peptide has carboxyl or carboxylate groups in positions other than the C-terminus, those groups may be amidated or esterified, and such amides or esters are also subsumed in the concept of the fragment peptide of the invention. The ester groups mentioned above may be the same as the C-terminal ester groups mentioned above.

Furthermore, the polypeptide or partial peptide of the invention may be a fusion protein with a protein having a well-known function or characteristic.

As the salt of the fragment peptide of the polypeptide of the invention, salts of the same kinds as those mentioned above for the polypeptide can be used.

The partial peptide of the polypeptide of the invention or an amide or ester thereof, or a salt thereof, can be produced by the same synthetic method as mentioned above for the polypeptide, or by cleaving the polypeptide of the invention with an appropriate peptidase.

The DNA coding for the polypeptide of the invention may be any DNA provided that it contains a DNA moiety having a binding affinity for a receptor protein comprising an amino acid sequence represented by SEQ ID NO:3 or a substantial equivalent thereto. Specifically, it may be any DNA that comprises a nucleotide sequence coding for a polypeptide comprising an amino acid sequence represented by ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40 or ⑤ a partial sequence of the amino acid sequence represented by SEQ ID NO:42, or a substantial equivalent thereto. It may be a genomic DNA, a genomic DNA library, a cDNA derived from the above-mentioned tissue or cells, a cDNA library derived from the above-mentioned tissue or cells, or a synthetic DNA. The vector to be used for library construction may be a bacteriophage, plasmid, cosmid, phagemid, or the like. Amplification may also be effected directly by the reverse transcriptase polymerase chain reaction technique (hereinafter, RT-PCR) using an RNA fraction may be prepared from the above-mentioned tissue or cells.

More specifically, (1) DNAs containing a DNA comprising ① the nucleotide sequence represented by SEQ ID NO:2 or a partial sequence thereof, ② a partial sequence of the nucleotide sequence represented by SEQ ID NO:16, ③ a partial sequence of the nucleotide sequence represented by SEQ ID NO:39, ④ a partial sequence of the nucleotide sequence represented by SEQ ID NO:41 or ⑤ a partial sequence of the nucleotide sequence represented by SEQ ID NO:43, (2) mammalian DNAs capable of hybridizing, under stringent conditions, with one of the sequences defined in (1), (3) DNAs incapable of hybridizing with any of the sequences defined in (1) and (2) due to genetic code degeneracy but coding for a polypeptide having the same amino acid sequence, and the like are used as the DNAs coding for polypeptides derived from mouse whole brain, rat whole brain, bovine hypothalamus, bovine stomach, human hypothalamus or human lung and comprising ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40 or ⑤ a partial sequence of the amino acid sequence represented by SEQ ID NO:42. The hybridization can be carried out by a per se known method or a modification thereof. The stringent conditions mentioned above are, for example, as follows: 42° C., 50% formamide, 4×SSPE (1×SSPE=150 mM NaCl, 10 mM NaH$_2$PO$_4$—$^H$$_2$O, 1 mM EDTA, pH 7.4), 5× Denhardt' solution, 0.1% SDS.

In the above-mentioned nucleotide sequence defined under SEQ ID NO:2, Y stands for T or C; N for T, C, A or G; R for A or G; M for C or A; W for T or A; and S for C or G.

Among the DNAs coding for a polypeptide comprising ① the amino acid sequence represented by SEQ ID NO:1 or a partial sequence thereof, ② a partial sequence of the amino acid sequence represented by SEQ ID NO:15, ③ a partial sequence of the amino acid sequence represented by SEQ ID NO:38, ④ a partial sequence of the amino acid sequence represented by SEQ ID NO:40, ⑤ a partial sequence of the amino acid sequence represented by SEQ ID NO:42, or the like, DNA fragments containing a partial sequence comprising 6 to 51 (preferably 9 to 30, more preferably 12 to 30) nucleotides can also be used with advantage as probes for DNA detection.

The DNA coding for the polypeptide of the present invention can be produced by the following genetic engineering procedures.

The DNA fully encoding the polypeptide of the present invention can be cloned either by PCR amplification using synthetic DNA primers having a partial nucleotide sequence of the polypeptide by hybridization using the DNA inserted in a suitable vector and labeled with a DNA fragment comprising a part or full region of a human-derived polypeptide or a synthetic DNA. The hybridization can be carried out typically by the procedure described in Molecular Cloning (2nd ed., J. Sambrook et al., Cold Spring Harbor Lab. Press, 1989). When a commercial library is used, the instructions given in the accompanying manual can be followed.

The cloned DNA coding for the polypeptide can be used directly or after digestion with a restriction enzyme or addition of a linker depending on purposes. This DNA has ATG as the translation initiation codon at the 5' end and may have TAA, TGA, or TAG as the termination codon at the 3' end. The translation initiation and termination codons can be added by means of suitable DNA adapters.

An expression vector for the polypeptide or partial peptide can be produced by, for example (a) cutting out a target DNA fragment from the DNA for the polypeptide or partial peptide of the present invention and (b) ligating the target DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, etc.; bacteriophages such as ρ-phage, and animal virus such as retrovirus, vaccinia virus and baculovirus.

According to the present invention, any promoter can be used as long as it is compatible with the host cell which is used for expressing a gene. When the host is an animal cell, the promoters include SV40-derived promoters, retrovirus promoters, metallothionein promoters, heat shock promoters, cytomegalovirus (CMV) promoters, SRα promoters, etc. When the host for the transformation is *E. coli*, the promoters are preferably trp promoters, lac promoters, recA promoters, λ $P_L$ promoters, lpp promoters, etc. When the host for the transformation is *Bacillus*, the promoters are preferably SPO1 promoters, SPO2 promoters, penP promoters, etc. When the host is a yeast, the promoters are preferably PHO5 promoters, PGK promoters, GAP promoters, ADH promoters, etc. When the host is a insect cel, the promoters are preferably polyhedrin promoters, Pl0 promoters, etc.

In addition to the above, optionally, the expression vector may further contain enhancer, splicing signal, poly A adenylation signal, selection marker, SV40 replication origin (hereinafter sometimes abbreviated to SV40 ori), etc. Examples of the selection marker include dihydrofolate reductase (hereinafter sometimes abbreviated to dhfr) gene [methotrexate (MTX) resistance], ampicillin resistant gene (hereinafter sometimes abbreviated to Amp$^r$), neomycin resistant gene (hereinafter sometimes abbreviated to Neo, G418 resistance), etc. In particular, when CHO (dhfr$^-$) cell is used together with dhfr gene as a selection marker, selection can also be carried out by using a thymidine free medium.

If necessary, a signal sequence which matches with a host is added to the N-terminal side of the receptor protein, etc. of the present invention. As the signal sequence, there may be mentioned PhoA signal sequence, Ompa signal sequence etc. in case of using bacteria of the genus *Escherichia* as the host; α-amylase signal sequence, subtilisin signal sequence, etc. in case of using bacteria of the genus Bacillus as the host; MFα signal sequence, SUC2 signal sequence, etc. in case of using yeast as the host; insulin signal sequence, α-interferon signal sequence, antibody molecule signal sequence, etc. in case of using animal cells as the host, respectively.

The DNA encoding the receptor protein, etc. of the present invention thus constructed can be introduced into a host to produce a transformant.

A transformant or transfectant is produced by using the vector thus constructed, which carries the polypeptide or partial peptide-encoding DNA of the present invention. The host may be, for example, *Escherichia* microorganisms, *Bacillus* microorganisms, yeasts, insect cells, animal cells, etc. Examples of the *Escherichia* microorganisms include *Escherichia coli*K12.DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of molecular Biology, Vol, 41, 459 (1969)], C600 [Genetics, Vol. 39, 440 (1954)], etc. Examples of the *Bacillus* microorganism are, for example *Bacillus subtilis* MI114 [Gene, Vol. 24, 255 (1983)], 207-21 [Journal of Biochemistry, Vol. 95, 76 (1984)], etc. The yeast may be, for example, *Saccharomyces cerevisiae* AH22, AH22R$^-$, NA87-11A, DKD-5D, 20B-12, etc. The insect may include a silkworm (*Bombyx mori larva*), [Maeda et al, Nature, Vol. 315, 592 (1985)] etc.

Examples of insect cells include *Spodoptera frugiperda* cell (Sf cell), MG1 cell derived from mid-intestine of *trichoplusia ni*, High Five™ cell derived from egg of *Trichoplusia ni*, cells derived from *Mamestra brassice*, cells derived from *Estigmena acrea*, etc. for the virus, AcNPV; and *Bombyx mori* N cell (BmN cell), etc. for the virus, BmNPV. As the Sf cell, for example, Sf9 cell (ATCC CRL1711) and Sf21 cell described by Vaughn, J. L., in Vitro, 13, 213-217 (1977) can be used.

Examples of animal cells include monkey cell COS-7, Vero cell, Chinese hamster cell CHO (hereinafter abbreviated to CHO cell), dhfr gene deficient Chinese hamster cell CHO (hereinafter abbreviated to CHO(dhfr$^-$) cell), mouse L cell, mouse myeloma cell, rat GH3 cell, human FL cell, 293 cell, C127 cell, mouse cell, BALB3T3 cell, Sp-2/0 cell etc.

Transformation of *Escherichia* microorganisms can be carried out in accordance with methods as disclosed in, for example, Proc. Natl. Acad. Sci. USA, Vol. 69, 2110 (1972), Gene, Vol. 17, 107 (1982), etc. Transformation of *Bacillus* microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells or the insect can be transformed in accordance with methods as disclosed in, for example, Bio/Technology, 6, 47-55, 1988. The animal cells can be transformed by methods as disclosed in, for example, Virology, Vol. 52, 456, 1973, etc.

Introduction of the expression vector into cells can be carried out, for example, by lipofection method (Felgner, P. L. et al. Proceedings of the National Academy of Sciences of the United States of America, 84, 7413 (1987)), calcium phosphate method (Graham, F. L. and van der Eb, A. J., Virology 52, 456-467 (1973)), electroporation (Nuemann, E. et al., EMBO J., 1, 841-845 (1982)) or the like.

Thus, the transformant transformed with the expression vector containing the DNA encoding the receptor protein, etc. of the present invention can be obtained.

As a method for stable expression of the receptor protein, etc. of the present invention by using an animal cell, there may be mentioned clone selection for selecting an animal cell wherein the expression vector introduced is integrated in its chromosome. More specifically, trasformants are selected by utilizing the above selection marker as an indicator. Further, clone selection of thus-obtained animal cells by using the above selection marker can be carried out repeatedly to obtain a stable animal cell line highly expressing the receptor protein, etc. of the present invention. When using a dhfr gene as the selection marker, an animal cell line more highly expressing the receptor protein can be obtained by cultivating the cell with gradually increasing MTX concentration to select a resistant strain, thereby amplifying the DNA encoding the protein, etc. of the present invention together with dhfr gene in the cell.

The polypeptide of the present invention can be produced by cultivating the above-described trasformant under such conditions that the DNA encoding the receptor protein, etc. of the present invention can be expressed to form and accumulate the polypeptide of the present invention.

Cultivation of the transformant (transfectant) in which the host is *Escherichia* or *Bacillus* microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeast extract, vitamines, growth-promoting factors, etc. It is desired that the culture medium is pH from about 5 to about 8.

The *Escherichia* microorganism culture medium is preferably an M9 medium containing, for example, glucose and casamino acid (Miller, Journal of Experiments in Molecular Genetics), 431-433, Cold Spring Harbor Laboratory, New York, 1972. Depending on necessity, the medium may be supplemented with drugs such as 3β-indolyl acrylic acid in order to improve efficiency of the promoter. In the case of an *Escherichia* host, the cultivation is carried out usually at about 15 to 43° C. for about 3 to 24 hours. As required, aeration and stirring may be applied. In the case of *Bacillus* host, the cultivation is carried out usually at about 30 to 40° C. for about 6 to 24 hours. As required, aeration and stirring may be also applied. In the case of the transformant in which the host is a yeast, the culture medium used may include, for example, a Burkholder minimum medium [Bostian, K. L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that the pH of the culture medium is adjusted to be from about 5 to about 8. The cultivation is carried out usually at about 20 to 35° C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T. C. C., Nature, 195, 788 (1962)). It is preferable that the pH of the culture medium is adjusted to be about 6.2 to 6.4. The cultivation is usually carried out at about 27° C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society of the Biological Medicine, Vol. 73, 1 (1950)], etc. which are containing, for example, about 5 to 20% of fetal calf serum. It is preferable that the pH is from about 6 to about 8. The cultivation is usually carried out at about 30 to 40° C. for about 15 to 60 hours. As required, medium exchange, aeration and stirring may be applied.

In particular, when using CHO (dhfr⁻) cell and dhfr gene as a selection marker, it is preferred to use DMEM medium which contains dialyzed fetal bovine serum almost free from thymidine.

Separation and purification of the polypeptide or partial peptide from the above-mentioned cultures can be carried out according to methods described herein below.

To extract polypeptide or partial peptide from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the polypeptide or partial peptide is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "TM").

In the case where the polypeptide or partial peptide are secreted into culture media, supernatant liquids are separated from the microorganisms or cells after the cultivation is finished and the resulting supernatant liquid is collected by widely known methods. The culture supernatant liquid and extract containing the polypeptide or partial peptide can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reverse-phase high-performance liquid chromatography, and methods utilizing a difference in the isoelectric point such as isoelectric electrophoresis, or chromatofocusing, etc.

When the thus-obtained polypeptide of the invention is in the free form, it may be converted to a salt by a per se known method or a modification thereof. When, conversely, it is obtained in a salt form, the salt may be converted to the free form or another salt by a per se known method or a modification thereof.

The polypeptide of the invention as produced by a transformant may be treated, prior to or after purification, with an appropriate protein modifying enzyme for arbitrary modification or partial polypeptide removal. The protein modifying enzyme to be used is, for example, trypsin, chymotrypsin, arginine endopeptidase, protein kinase, or glycosidase.

The presence of the thus-formed polypeptide of the invention can be detected, for example, by enzyme immunoassay using a specific antibody.

The DNA coding for the polypeptide of the invention or the polypeptide of the invention can be used for ① synthesizing a part or the full length of a ligand for a G protein-coupled receptor protein, ② searching for a physiological activity of the polypeptide of the invention, ③ preparing a synthetic oligonucleotide probe or PCR primers, ④ obtaining a DNA coding for a ligand for a G protein-coupled receptor protein, or a precursor protein, ⑤ developing a receptor binding assay system using a recombinant receptor protein expression system and screening for candidate medicinal compounds, ⑥ obtaining antibodies and antisera, ⑦ developing diagnostic agents using DNAS, RNAs, antibodies or antisera, ⑧ developing central nervous system function modulators, circulatory function modulators, immune function modulators, gastrointestinal function modulators, metabolic function modulators or reproductive function modulators, for instance, ⑨ gene therapy, and so forth.

In particular, said DNA or polypeptide can be used in screening for human- or warm-blooded animal-specific G protein-coupled receptor agonists or antagonists using a receptor binding assay system in which the recombinant G protein-coupled receptor protein expression system mentioned later herein is used. Said agonists or antagonists can be used as an agent for preventing or treating various diseases.

Referring further to the above-mentioned use ⑧the polypeptide of the invention or the DNA coding therefor is recognized as a ligand by the G protein-coupled receptor protein expressed in the central nervous system, circulatory system, immune system, gastrointestinal system, metabolic system or reproductive system, for instance, and, therefore, is useful as a safe and low-toxicity medicament. The polypeptide of the invention or the DNA coding therefor is associated with the modulation of central nervous system function, circulatory function, immune function, gastrointestinal function, metabolic function, reproductive function, etc., and, therefore, can be used as a therapeutic and/or prophylactic agent for a variety of diseases, e.g. various types of dementia such as senile dementia, cerebrovascular dementia, dementia due to genealogical denaturation degenerative diseases (e.g. Alzheimer's disease, Parkinson's disease, Pick's disease, Huntington's disease, etc.), dementia resulting from infectious diseases (e.g. delayed virus infections such as Creutzfeldt-Jakob disease), dementia associated with endocrine diseases, metabolic diseases, or poisoning (e.g. hypothyroidism, vitamin B12 deficiency, alcoholism, poisoning caused by various drugs, metals, or organic compounds), dementia caused by tumors (e.g. brain tumor), and dementia due to traumatic diseases (e.g. chronic subdural hematoma), depression, hyperactive child syndrome (microencephalopathy), disturbance of consciousness, anxiety disorder, schizophrenia, phobia, growth hormone secretory disorder (e.g. gigantism, acromegaly, etc.), hyperphagia, polyphagia, hypercholesterolemia, hyperglyceridemia, hyperlipemia, hyperprolactinemia, diabetes mellitus (e.g. diabetic complications such as diabetic nephropathy, diabetic neuropathy, diabetic retinopathy, etc.), cancer (e.g. mammary cancer, lymphocytic leukemia, lung cancer, bladder cancer, ovary cancer, carcinoma of prostate, etc.), pancreatitis, diseases of kidney (e.g. chronic renal failure, nephritis, etc.), Turner's syndrome, neurosis, rheumatoid arthritis, spinal injury, transient brain ischemia, amyotrophic lateral sclerosis, acute myocardial infarction, spinocerebellar degeneration, bone fracture, wounds, atopic dermatitis, osteoporosis, asthma, epilepsy, sterility, arteriosclerosis, pulmonary emphysema, pulmonary edema, and galactorrhea. It can further be used as a postoperative nutritional status improving agent or as a vasopressor.

In addition, it can be used as drug for treating or preventing HIV infection or AIDS(acquired immune deficiency syndrome) or the like.

When the polypeptide of the invention or the DNA encoding therefor is used as a pharmaceutical composition as described above, it can be used by conventional methods. For example, it can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the polypeptide, a partial peptide thereof, or the DNA encoding either of them with physiologically acceptable carriers, flavoring agents, excipients, vehicles, antiseptics, stabilizers, binders etc. in unit dosage forms required for generally accepted manners of pharmaceutical making. Active ingredient contents in these preparations are set so that an appropriate dose within the specified range is obtained.

When the DNA of the invention is used, the DNA can be applied either as it is alone or as inserted into an appropriate vector, for example a retrovirus vector, adenovirus vector or adenovirus-associated virus vector.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical making such as by dissolving or suspending active ingredients, naturally occuring vegetable oils such as sesame oil and coconut oil, etc. in vehicles such as water for injection.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80 (TM) and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. The thus-prepared injectable liquid is normally filled in an appropriate ampule. Because the thus-obtained preparation is safe and of low toxicity, it can be administered to humans or warm-blooded mammals, e.g., mouse, rats, guinea pig, rabbits, chicken, sheep, pigs, bovines, cats, dogs, monkeys, baboons, chimpanzees, for instance.

The dose of said polypeptide, a partial peptide thereof, or the DNA encoding either of them is normally about 0.1-100 mg, preferably 1.0-50 mg, and more preferably 1.0-20 mg per day for an adult patient of pulmanary emphysema (weighing 60 kg) in oral administration, depending on symptoms etc. In non-oral administration, it is advantageous to administer the polypeptide, a partial peptide thereof, or the DNA encoding either of them in the form of injectable preparation at a daily dose of about 0.01-30 mg, preferably about 0.1-20 mg, and more preferably about 0.1-10 mg per administration by an intravenous injection for an adult patient of pulmonary emphysema(weighing 60 kg), depending on subject of administration, target organ, symptoms, method of administration etc. For other animal species, corresponding does as converted per 60 kg weight can be administered.

The G protein-coupled receptor protein for the polypeptide of the invention may be any protein provided that it is a G protein-coupled receptor protein derived from the tissue (e.g. hypophysis, pancreas, brain, kidney, liver, gonad, thyroid gland, gallbladder, bone marrow, adrenal gland, skin, muscle, lung, digestive tract, blood vessel, heart) or cells of a human or warm-blooded animal (e.g. warm-blooded mammal such as rabbit, sheep, goat, rat, mouse, guinea pig, cattle, horse, swine, etc.), avian species (e.g. poultry, pigeon, duck, goose, quail)) and comprising an amino acid sequence identical or substantially represented by SEQ ID NO:3 or a substanial equivalent thereto. Thus, as the G protein-coupled receptor protein, there may be mentioned not only proteins comprising the amino acid sequence represented by SEQ ID NO:3 but also proteins comprising an amino acid sequence having a homology of about 90 to 99.9% relative to the amino acid sequence represented by SEQ ID NO:3 and having an activity or activities of substantially equivalent nature as that or those of proteins comprising the amino acid sequence defined under SEQ ID NO:3, among others.

As the activities which these proteins exhibit, there may be mentioned, for example, ligand binding activity, signal transduction, and the like. The term "substantially equivalent" means the qualitative equivalence in ligand binding or other activity. Thus, there may be variations in quantitative factors such as the intensity of ligand bind activity and the molecular weight of the receptor protein.

Furthermore, the G protein-coupled receptor protein includes those in which the N-terminal Met is protected with a protective group (e.g. $C_{1-6}$ acyl such as formyl or acetyl), those resulting from in vivo cleavage of Gln on the N terminal side and conversion of said Gln to a pyroglutamic acid residue, those in which the side chain of an intramolecular amino acid is protected with an appropriate protective group (e.g. $C_{1-6}$ acyl group such as formyl or acetyl), and conjugated proteins such as the so-called glycoproteins resulting from binding with a sugar chain.

As the salt of the G protein-coupled receptor protein, there may be mentioned those salts mentioned hereinabove for the polypeptide.

The G protein-coupled receptor protein or a salt thereof, or a partial peptide derived therefrom, can be produced from human or warm-blooded animal tissues or cells by a per se known method of protein purification. It can also be produced in the same manner as the above-mentioned method comprising growing a transformant harboring a DNA coding for the polypeptide. It can further be produced by the above-mentioned method of peptide synthesis.

Referring to the above-mentioned partial peptide derived from the G protein-coupled receptor protein, the exofacial region of the G protein-coupled receptor protein molecule, which is exposed out of the cell membrane, can be used, for instance. Thus, it is a peptide containing that portion of the G protein-coupled receptor protein which is detected as an extracellular domain (hydrophilic site) in hydropathy analysis. Peptides comprising parts of the hydrophobic site can also be used. Peptides each comprising one of such domains as well as peptides comprising a plurality of such domains can be used.

As the salt of the fragment peptide derived from the G protein-coupled receptor protein, the same kinds of salts as mentioned above for the ligand polypeptide can be used.

The DNA coding for the G protein-coupled receptor protein may be any DNA provided that it comprises a nucleotide sequence coding for a G protein-coupled receptor protein comprising an amino acid sequence represente by SEQ ID NO:3 or a substantial equivalent thereto. It may be a genomic DNA, genomic DNA library, tissue- or cell-derived cDNA, tissue- or cell-derived cDNA library, or synthetic DNA. The vector to be used in library construction may be a bacteriophage, plasmid, cosmid, phagemid or the like. Amplification can also be carried out directly by the per se known RT-PCR technique using an RNA fraction prepared from a tissue or cells.

Particularly, a DNA comprising the nucleotide sequence represented by SEQ ID NO:4, for instance, is used as a DNA coding for a G protein-coupled receptor protein comprising the amino acid sequence defined under SEQ ID NO:3.

In the following, the uses for the polypeptide of the invention, the DNA coding for said polypeptide and the antibody against the same, among others, are illustrated specifically.

(1) Drugs for the Treatment or Prevention of Ligand Polypeptide Deficiency

The DNA coding for the polypeptide of the invention can be used also as a prophylactic or therapeutic agent for ligand polypeptide or G protein-coupled receptor protein (APJ) deficiency according to the activity or activities which the polypeptide of the invention has in relation to the G protein-coupled receptor protein (APJ).

Thus, for instance, where there is a patient presenting with a reduced in vivo level of the polypeptide of the invention or the G protein-coupled receptor protein (APJ) and, therefore, hardly expected to have the physiological activities (central nervous system function modulating activity, circulatory function modulating activity, immune function modulating activity, gastrointestinal function modulating activity, metabolic function modulating activity, reproductive function modulating activity, etc.) of the ligand therefor, sufficiently expressed, it is possible to cause said activities of the ligand polypeptide to be expressed to a sufficient extent by increasing the level of the ligand polypeptide in brain cells of said patient by (a) administering the DNA coding for the polypeptide of the invention or (b) inserting the DNA coding for the polypeptide of the invention into the brain cells, for instance, to thereby cause expression thereof and then transplanting the brain cells into the patient. Therefore, the DNA coding for the polypeptide of the invention can be used as a safe and low-toxicity prophylactic or therapeutic agent for ligand polypeptide deficiency syndrome.

In using the above-mentioned DNA as such a therapeutic agent, the same means as mentioned above for the use of the DNA coding for the polypeptide or partial peptide of the invention as a drug can be employed, using said DNA as it is alone or as inserted into an appropriate vector, for example a retrovirus vector, adenovirus vector or adenovirus-associated virus vector.

(2) Assaying of the G Protein-Coupled Receptor Protein (APJ) Against the Ligand Polypeptide The polypeptide of the invention is capable of binding to the G protein-coupled receptor protein (APJ) or a salt thereof or to a partial peptide or a salt thereof as derived from said receptor protein and therefore can be used in determining, with good sensitivity, the in vivo level of the G protein-coupled receptor protein (APJ) or a salt thereof or a fragment peptide derived from said receptor protein or a salt thereof.

This assay method can be used in combination with the competitive binding technique, for instance. Thus, the concentration of the G protein-coupled receptor protein (APJ) or a salt thereof or a partial peptide derived from the G protein-coupled receptor protein (APJ) or a salt thereof in a test sample can be determined by contacting the test sample with the polypeptide of the invention. Specifically, the assay can be performed, for example by the per se known method described in the reference ① or ② cited below or a modification thereof.

① Hiroshi Irie (ed.): "Radioimmunoassay" (published by Kodansha, 1974);

② Hiroshi Irie (ed.): "Radioimmunoassay, A Sequel" (published by Kodansha, 1979).

(3) Screening for Compounds Capable of Modifying the Binding Between the G Protein-Coupled Receptor Protein (APJ) and the Polypeptide of the Invention, an Amide or Ester Thereof, or a Salt Thereof (Hereinafter Sometimes Collectively Referred to as Ligand or Ligand Polypeptide for Short)

Compounds capable of modifying the binding of the ligand polypeptide to the G protein-coupled receptor protein (APJ) (e.g. peptides, proteins, nonpeptide compounds, synthetic compounds, fermentation products, etc.), inclusive of salts thereof, can be screened for by using the G protein-coupled receptor protein (APJ) or a salt thereof or said partial peptide or a salt thereof, or by constructing a recombinant receptor protein (APJ) expression system and using a receptor binding assay system in which said expression system is used. Such compounds include those compounds which are capable of exhibiting cell stimulating activities (e.g. promotor or inhibitor actions on arachidonic acid release, acetylcholine release, intracellular $Ca^{2+}$ release, intracellular cAMP production, intracellular cGMP production, inositol phosphate production, cell membrane potential change, intracellular protein phosphorylation, c-fos activation, pH depression) via the G protein-coupled receptor (APJ) (namely G protein-coupled receptor agonists) and those compounds having no cell stimulating activities (namely G protein-coupled receptor antagonists). The term "capable of modifying the binding to the ligand" covers both the case where the binding to the ligand is inhibited and the case where the binding to the ligand is promoted.

The present invention thus provides a method of screening for a compound, or a salt thereof, capable of modifying the binding of the polypeptide of the invention to the above-mentioned G protein-coupled receptor protein (APJ) which comprises, on the one hand, (i) bringing the ligand of the invention into contact with the G protein-coupled receptor protein (APJ) or a salt thereof or a partial peptide derived from said receptor protein or a salt thereof and, on the other hand, (ii) bringing the polypeptide of the invention and a test compound into contact with the above-mentioned G protein-coupled receptor protein (APJ) or a salt thereof or the partial peptide derived from said receptor protein or a salt thereof, and making a comparison between the two cases (i) and (ii).

In the screening method of the invention, (i) the polypeptide of the invention is contacted with the above-mentioned G protein-coupled receptor protein (APJ) or a partial peptide derived from said receptor protein and (ii) the polypeptide of the invention and a test compound are contacted with the above-mentioned G protein-coupled receptor protein (APJ) or the partial peptide derived from said receptor protein and the levels of binding of the ligand to said G protein-coupled receptor protein (APJ) or the partial peptide derived from said receptor protein or any of said cell stimulating activities, for instance, are determined in the cases (i) and (ii) and compared therebetween.

The screening method specifically includes:

① a method of screening for a compound, or a salt thereof, which is capable of modifying the binding of the polypeptide of the invention to the above-mentioned G protein-coupled receptor protein (APJ) which comprises, on the one hand, bringing a labeled form of the polypeptide of the invention into contact with the G protein-coupled receptor protein (APJ) or a salt thereof or a partial peptide derived from the G protein-coupled receptor protein or a salt thereof and, on the other hand, bringing the labeled polypeptide of the invention and a test compound into contact with the above-mentioned G protein-coupled receptor protein (APJ) or its salt or the partial peptide derived from said receptor protein or its salt, measuring the levels of binding of the labeled polypeptide of the invention to the G protein-coupled receptor protein (APJ) or its salt or the partial peptide derived from the G protein-coupled receptor protein (APJ) or its salt in both cases and making a comparison therebetween;

② a method of screening for a compound or a salt thereof, which is capable of modifying the binding of the polypeptide of the invention to the above-mentioned G protein-coupled receptor protein (APJ) which comprises, on the one hand, bringing a labeled form of the polypeptide of the invention into contact with cells containing the G protein-coupled receptor protein (APJ) or a membrane fraction of said cells and, on the other hand, bringing the labeled polypeptide of the invention and a test compound into contact with such G protein-coupled receptor protein (APJ)-containing cells or membrane fraction, measuring the binding of the labeled polypeptide of the invention to said cells or membrane fraction in both cases and making a comparison therebetween;

③ a method of screening for a compound or a salt thereof, which is capable of modifying the binding of the polypeptide of the invention to the above-mentioned G protein-coupled receptor protein (APJ) which comprises, on the one hand, bringing a labeled form of the polypeptide of the invention into contact with the G protein-coupled receptor protein (APJ) expressed on the cell membrane upon cultivation of a transformant harboring a DNA coding for the G protein-coupled receptor protein (APJ) and, on the other hand, bringing the labeled polypeptide of the invention and a test compound into contact with the G protein-coupled receptor protein (APJ) expressed on the cell membrane upon cultivation of the transformant harboring the DNA coding for the G protein-coupled receptor protein, measuring the binding of the labeled polypeptide of the invention to said G protein-coupled receptor protein in both cases and making a comparison therebetween;

④ a method of screening for a compound or a salt thereof, which is capable of modifying the binding of the polypeptide of the invention to the above-mentioned G protein-coupled receptor protein (APJ) which comprises, on the one hand, bringing a compound capable of activating the G protein-coupled receptor protein (APJ) (e.g. the polypeptide of the invention) into contact with cells containing the G protein-coupled receptor protein (APJ) and, on the other hand, bringing the compound capable of activating the G protein-coupled receptor protein (APJ) and a test compound into contact with such G protein-coupled receptor protein (APJ)-containing cells, measuring a G protein-coupled receptor protein (APJ)-mediated cell stimulating activity (e.g. a promotor or inhibitor action on arachidonic acid release, acetylcholine release, intracellular $Ca^{2+}$ release, intracellular cAMP production, intracellular cGMP production, inositol phosphate production, cell membrane potential change, intracellular protein phosphorylation, c-fos activation, pH depression) in both cases and making a comparison therebetween; and ⑤ a method of screening for a compound or a salt thereof, which is capable of modifying the binding of the polypeptide of the invention to the above-mentioned G protein-coupled receptor protein (APJ) which comprises, on the one hand, bringing a compound capable of activating the G protein-coupled receptor protein (APJ) (e.g. the polypeptide of the invention) into contact with the G protein-coupled receptor protein (APJ) expressed on the cell membrane upon cultivation of a transformant harboring a DNA coding for the G protein-coupled receptor protein (APJ) and, on the other hand, bringing the compound capable of activating the G protein-coupled receptor protein (APJ) and a test compound into contact with the G protein-coupled receptor protein (APJ) expressed on the cell membrane upon cultivation of the transformant harboring the DNA coding for the G protein-coupled receptor protein, measuring a G protein-coupled receptor protein (APJ)-mediated cell stimulating activity (e.g. a promotor or inhibitor action on arachidonic acid release, acetylcholine release, intracellular $Ca^{2+}$ release, intracellular cAMP production, intracellular cGMP produciton, inositol phosphate production, cell membrane potential change, intracellular protein phosphorylation, c-fos activation, pH depression) in both cases and making a comparison therebetween; among others.

The screening method of the invention is specifically illustrated in the following.

In the first place, the G protein-coupled receptor protein (APJ) to be used in the screening method of the invention may be of any origin provided that it comprises the above-mentioned G protein-coupled receptor protein or a partial peptide derived from the G protein-coupled receptor protein. Human or warm-blooded animal organ-derived membrane fractions are suitable. Since, however, human organs are very difficult to obtain, the G protein-coupled receptor protein (APJ) produced by high level expression using a recombinant, for instance, is preferred.

The G protein-coupled receptor protein (APJ) can be produced, for instance, by the method mentioned above.

When cells containing the G protein-coupled receptor protein or a membrane fraction of said cells is used in carrying out the screening method of the invention, the preparation procedure mentioned below may suitably be followed.

When cells containing the G protein-coupled receptor protein are used, the cells may be fixed with glutaraldehyde, formalin or the like. Fixation can be effected by a per se known method.

The G protein-coupled receptor protein-containing cells are host cells with the G protein-coupled receptor protein expressed therein. As said host cells, there may be mentioned the above-mentioned *Escherichia coli, Bacillus subtilis*, yeasts, insect cells, animal cells and so on.

The membrane fraction is a cell membrane-rich fraction obtained by disrupting cells and then following a per se known technique. As the method of disrupting, there may be mentioned, among others, the method of crushing cells using a Potter-Elvehjem type homogenizer, the disruption using a Waring Blendor or Polytron (Kinematica), the disruption with supersonic waves, and the disruption by spouting cells placed under pressure with a French press or the like through a narrow nozzle. For cell membrane fractionation, the fractionation by centrifugal force, for example fractional centrifugation or density gradient centrifugation, is mainly used. For instance, a cell disruption mixture is centrifuged at a low rotational speed (500 rpm to 3,000 rpm) for a short period (generally about 1 to 10 minutes) and the supernatant obtained is further centrifuged at a higher speed (15,000 rpm to 30,000 rpm) generally for 30 minutes to 2 hours; the pellet obtained is used as the membrane fraction. The G protein-coupled receptor protein expressed and other membrane components, such as cell-derived phospholipids and membrane proteins, are abundant in said membrane fraction.

The content of the G protein-coupled receptor protein in the G protein-coupled receptor protein-containing cells or membrane fraction is preferably $10^3$ to $10^8$ molecules per cell, more preferably $10^5$ to $10^7$ molecules per cell. When the level of expression is high, the membrane fraction has high ligand binding activity (specific activity), hence it is possible not only to construct a high sensitivity screening system but also to assay a large number of samples using one and the same lot.

In carrying out the above-mentioned versions ①  to ③ of the method for screening for a compound capable of modifying the binding of the polypeptide of the invention to the G protein-coupled receptor protein, an appropriate G protein-coupled receptor fraction and the polypeptide of the invention in a labeled form are used. Desirable as the G protein-coupled receptor fraction is a native G protein-coupled receptor fraction, a recombinant G protein-coupled receptor fraction equivalent in activity to said natural fraction, or the like. The term "equivalent in activity" refers to equivalence in ligand binding activity, for instance. The labeled ligand includes not only a labeled ligand but also a labeled ligand analog and so on. For example, the ligand labeled with $[^3H], [^{125}I], [^{14}C]$ or $[^{35}S]$ may be used.

Specifically, in screening for a compound capable of modifying the binding of the polypeptide of the invention to the G protein-coupled receptor protein, a receptor standard is first prepared by suspending cells containing the G protein-coupled receptor protein (APJ) or a membrane fraction of said cells in a buffer suited for the screening. The buffer may be phosphate buffer or Tris-hydrochloride buffer or any other buffer incapable of inhibiting ligand-receptor binding and having a pH of 4 to 10 (desirably 6 to 8). For the purpose of reducing non-specific binding, a surfactant such as CHAPS, Tween-80™ (Kao-Atlas), digitonin or deoxycholate may be added to the buffer. For preventing the receptor or the polypeptide of the invention from being decomposed with proteases, a protease inhibitor, such as PMSF, leupeptin, E-64 (Peptide Institute) or pepstatin, may further be added. To 0.01 ml to 10 ml of said receptor solution is added a predetermined amount (5,000 cpm to 500,000 cpm) of the labeled polypeptide of the invention and, at the same time, a test compound is caused to coexist at $10^{-4}$ to $10^{-1}$ µM. To ascertain the non-specific binding (NSB), reaction tubes with a large excess of the unlabeled polypeptide of the invention added are also prepared. The reaction is carried out at 0° C. to 50° C., preferably 4° C. to 37 ° C., for 20 minutes to 24 hours, preferably 30 minutes to 3 hours. After the reaction, each reaction mixture is filtered through glass fiber filter paper or the like and, after washing with an appropriate amount of the same buffer, the radioactivity remaining on the glass fiber filter paper is measured using a liquid scintillation counter or γ-counter. When the count ($B_0$) in the case of absence of any antagonizing substance minus the non-specific binding (NSB), namely the count ($B_0$–NSB), is taken as 100%, a test compound showing a specific binding (B–NSB) which is not more than 50%, for instance, of the count ($B_0$–NSB) can be selected as a candidate substance possibly having antagonizing or inhibiting activity.

In carrying out the above-mentioned method ④ or ⑤ for screening for a compound capable of modifying the binding of the polypeptide of the invention to the G protein-coupled receptor protein (APJ), the G protein-coupled receptor protein-mediated cell stimulating activity (e.g. a promotor or inhibitor action on arachidonic acid release, acetylcholine release, intracellular $Ca^{2+}$ release, intracellular cAMP production, intracellular cGMP production, inositol phosphate production, cell membrane potential change, intracellular protein phosphorylation, c-fos activation, pH depression) can be measured using a per se known method or a commercially available assay kit. Specifically, cells containing the G protein-coupled receptor protein are first cultured on multiwell plates or the like. Prior to carrying out the screening, the medium is replaced with a fresh medium or an appropriate buffer showing no toxicity against the cells. The test compound etc. are then added and, after a predetermined period of incubation, the cells are extracted or the supernatant is recovered, and the product or products formed are assayed by the respective methods. If the formation of a substance (e.g. arachidonic acid) employed as the indicator of cell stimulating activity is difficult to detect due to a decomposing enzyme contained in the cells, the assay may be carried out in the presence of an inhibitor, added beforehand, against said decomposing enzyme. As regards the cAMP production inhibiting activity or the like, said activity can be detected in terms of production inhibiting activity against cells in which the basal production has been increased with forskolin or the like.

For the screening based on the measurement of a cell stimulating activity, appropriate cells with the G protein-coupled receptor protein expressed therein are required. Desirable as the cells with the G protein-coupled receptor protein expressed therein which are to be used according to the invention are cells of the above-mentioned recombinant G protein-coupled receptor protein (APJ) expression cell line, among others.

As the test compound, there may be mentioned, for example, peptides, proteins, nonpeptide compounds, synthetic compounds, fermentation products, cell extracts, plant extracts, animal tissue extracts, etc. These compounds may be novel compounds or known ones.

The screening kit for a compound or a salt thereof, which is capable of modifying the binding of the polypeptide of the invention to the G protein-coupled receptor protein (APJ) comprises the G protein-coupled receptor protein or a salt thereof, a partial peptide derived from the G protein-coupled receptor protein or a salt thereof, cells containing the G protein-coupled receptor protein or a membrane fraction of cells containing the G protein-coupled receptor protein, together with the polypeptide of the invention.

As examples of the screening kit of the invention, there may be mentioned the following:

1. Reagents for Screening

① Assay Buffer and Wash Buffer

Hank's balanced salt solution (Gibco) supplemented with 0.05% bovine serum albumin (Sigma).

This is sterilized by filtration through a filter with a pore size of 0.45 μm and stored at 4° C. It may be prepared extemporaneously.

② G Protein-Coupled Receptor (APJ) Standard

CHO cells with the G protein-coupled receptor protein (APJ) expressed therein are subcultured on 12-well plates at $5 \times 10^5$ cells/well and incubated under the conditions of 37° C. and 5% $CO_2$ plus 95% air for 2 days.

③ Labeled Ligand

The ligand labeled with [$^3$H], [$^{125}$I], [$^{14}$C], [$^{35}$S] or the like.

It is dissolved in an appropriate solvent or buffer, stored at 4° C. or −20° C. and extemporaneously diluted to 1 μM with assay buffer.

④ Standard Ligand Solution

The polypeptide of the invention is dissolved in PBS containing 0.1% bovine serum albumin (Sigma) to a concentration of 1 mM and stored at −20° C.

2. Assay Method

① Cells caused to express the G protein-coupled receptor protein by cultivating on 12-well tissue culture plates are washed with two 1 ml portions of assay buffer and, then, 490 μl of assay buffer is added to each well ② 5 μl of a $10^{-3}$ to $10^{-10}$ M solution of the test compound is added, then 5 μl of the polypeptide of the invention in a labeled form is added, and the reaction is allowed to proceed at room temperature for 1 hour. To ascertain the non-specific binding, 5 μl of a $10^{-3}$ M solution of the ligand is added in lieu of the test compound.

③ The reaction solution is removed and each well is washed with three 1 ml portions of wash buffer. The cell-bound labeled ligand is dissolved using 0.2 N NaOH-1% SDS and the solution is mixed with 4 ml of liquid scintillator A (Wako Pure Chemical Industries).

④ The radioactivity is measured using a liquid scintillation counter (Beckman) and expressed in terms of percent maximum binding (PMB) according to the formula shown below.

$$PMB = [(B-NSB)/(B_0-NSB)] \times 100 \qquad \text{[Formula 1]}$$

where PMB: percent maximum binding;
 B: value when the test compound is added;
 NSB: non-specific binding;
 $B_0$: maximum binding.

The compound, inclusive of its salt, obtained by using the screening method or screening kit of the invention is a compound capable of modifying (inhibiting or promoting) the binding of the polypeptide of the invention to the G protein-coupled receptor (APJ) and, more particularly, a compound, or a salt thereof, showing G protein-coupled receptor-mediated cell stimulating activity (the so-called G protein-coupled receptor agonist) or a compound having no such cell stimulating activity (the so-called G protein-coupled receptor antagonist). As said compound, there may be mentioned peptides, proteins, nonpeptide compounds, synthetic compounds, fermentation product compounds and so on. These compounds may be novel compounds or known ones.

The evaluation of the compound in question as to whether it is the above-mentioned G protein-coupled receptor agonist or antagonist can be embodied as mentioned below under (i) or (ii).

(i) After a compound capable of modifying (in particular inhibiting) the binding of the polypeptide of the invention to the G protein-coupled receptor is obtained by performing the binding assay indicated above under ① to ③, said compound is tested as to whether it has said G protein-coupled receptor-mediated cell stimulating activity. A compound, or a salt thereof, which has such cell stimulating activity is a G protein-coupled receptor agonist, while a compound, or a salt thereof, which has no such activity is a G protein-coupled receptor antagonist.

(ii) (a) The test compound is contacted with cells containing the G protein-coupled receptor protein and measured for the above-mentioned G protein-coupled receptor-mediated cell stimulating activity. A compound, or a salt thereof, which has such cell stimulating activity is a G protein-coupled receptor agonist.

(b) A compound capable of activating the G protein-coupled receptor (e.g. the polypeptide of the invention or a G protein-coupled receptor agonist) is contacted with cells containing the G protein-coupled receptor protein. On the other hand, the compound capable of activating the G protein-coupled receptor and the test compound are contacted with cells containing the G protein-coupled receptor protein. In both cases, the G protein-coupled receptor-mediated cell stimulating activity levels are measured and compared with each other. A compound, or a salt thereof, which lowers the cell stimulating activity of the compound capable of activating the G protein-coupled receptor is a G protein-coupled receptor antagonist.

Said G protein-coupled receptor agonist has the same physiological activities as those which the polypeptide of the invention has with respect to the G protein-coupled receptor protein and, therefore, it can be used as a safe and low-toxicity drug in the same manner as the polypeptide of the invention.

Conversely, the G protein-coupled receptor antagonist inhibits the physiological activities which the polypeptide of the invention has with respect to the G protein-coupled receptor protein and, therefore, it is useful as a safe and low-toxicity drug inhibiting said receptor activities.

Since the polypeptide of the invention is involved in the modulation of central nervous system function, circulatory function, immune function, gastrointestinal function, metabolic function, reproductive function, etc., the above-mentioned agonist or antagonist can be used as a drug for treating or preventing a variety of diseases, e.g. various types of dementia such as senile dementia, cerebrovascular dementia, dementia due to genealogical denaturation degeneration diseases (e.g. Alzheimer's disease, Parkinson's disease, Pick's disease, Huntington's disease, etc.), dementia caused by infectious diseases (e.g. delayed virus infections such as Creutzfeldt-Jakob disease), dementia associated with endocrine diseases, metabolic diseases, or poisoning (e.g. hypothyroidism, vitamin B12 deficiency, alcoholism, poisoning caused by various drugs, metals, or organic compounds), dementia caused by tumors (e.g. brain tumor), and dementia due to traumatic diseases (e.g. chronic subdural hematoma), depression, hyperactive child syndrome (microencephaopathy), disturbance of consciousness, anxiety disorder, schizophrenia, phobia, growth hormone secretory disorder (e.g. gigantism, acromegaly, etc.), hyperphagia, polyphagia, hypercholesterolemia, hyperglyceridemia, hyperlipemia, hyperprolactinemia, hypoglycemia, hypopituitarism, pituitary dwarfism, diabetes mellitus (e.g. diabetic complications such as diabetic nephropathy, diabetic neuropathy, diabetic retinopathy, etc.), cancer (e.g. mammary cancer, lymphocytic leukemia, lung cancer, bladder cancer, ovary cancer, carcinoma of prostate, etc.), pancreatitis, diseases of kidney (e.g. chronic renal failure, nephritis, etc.), Turner's syndrome, neurosis, rheumatoid arthritis, spinal injury, transient brain ischemia, amyotrophic lateral sclerosis, acute myocardial infarction, spinocerebellar degeneration, bone fracture, wounds, atopic dermatitis, osteoporosis, asthma, epilepsy, sterility, arteriosclerosis, pulmonary emphysema, pulmonary edema, and agalactorrhea. It can further be used as a hypnotic sedative, a postoperative nutritional status improving agent, a vasopressor, a hypotensive agent or the like.

In addition, it can be used as drug for treating or preventing HIV infection or AIDS (acquired immune deficiency syndrome) or the like.

Usable as the salt of the compound obtained by using the above-mentioned screening method or screening kit are, for example, pharmaceutically acceptable salts. As examples, there may be mentioned salts with inorganic bases, salts with organic bases, salts with inorganic acids, salts with organic acids, and salts with basic or acidic amino acids.

As suitable examples of the salts with inorganic bases, there may be mentioned alkali metal salts such as sodium salt and potassium salt, alkaline earth metal salts such as calcium salt and magnesium salt, aluminum salt and ammonium salt.

As suitable examples of the salts with organic bases, there may be mentioned salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

As suitable examples of the salts with inorganic acids, there may be mentioned salts with hydrochloric acid, hydrobromic acid, sulfuric acid, phosphoric acid and the like.

As suitable examples of the salts with organic acids, there may be mentioned salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid and the like.

As suitable examples of the salts with basic amino acids, there may be mentioned salts with arginine, lysine, ornithine and the like. As suitable examples of the salts with acidic amino acids, there may be mentioned salts with aspartic acid, glutamic acid and the like.

The use, as the drug mentioned above, of the compound or salt obtained by using the screening method or screening kit of the invention can be made in the same manner as in the case of applying the polypeptide of the invention as a drug.

(5) Manufacture of Antibody or Antiserum Against the Polypeptide or the Invention Antibodies, e.g. polyclonal antibody, monoclonal antibody, and antisera against the polypeptide of the invention may be manufactured by antibody- or antiserum-manufacturing methods per se known to those of skill in the art or methods similar thereto, using the polypeptide of the invention as antigen. For example, polyclonal antibodies can be manufactured by the method as given below.

[Preparation of a Polyclonal Antibody]

A polyclonal antibody against the receptor protein, etc. of the present invention can be prepared by a per se known method or its modification. For example, an immunogen (an antigen against the receptor protein, etc.) itself or a complex thereof with a carrier protein is prepared and a mammal is immunized according to the same manner as that described with respect to the above monoclonal antibody preparation. A material containing the antibody against the receptor protein, etc. of the present invention is recovered from the immunized animal and the antibody is separated and purified.

As to the complex of the immunogen and the carrier protein to be used for immunization of a mammal, any carrier protein and any mixing proportion of the carrier and a hapten can be employed in so far as an antibody against the hapten, which is crosslinked on the carrier and used for immunization, is produced efficiently. For example, bovine serum albumin, bovine cycloglobulin, keyhole limpet hemocyanin, etc. can be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, there may be mentioned glutaraldehyde, carbodiimide, maleimide activated ester, activated ester reagents containing thiol group or dithiopyridyl group, and the like.

The condensation product as such or together with a suitable carrier or diluent is administered to a site of a mammal which permits the antibody production. For enhancing the antibody productivity, complete Freund's adjuvant or incomplete Freund's adjuvant may be administered. Normally, the protein, etc. is administered once evey 2 weeks to 6 weeks, in total, about 3 times to about 10 times.

The polyclonal antibody is recovered from blood, ascites and the like, preferably blood of an animal immunized by the above method.

The antibody titer of the polyclonal antibody in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The monoclonal antibody can be produced by the following method.

[Preparation of Monoclonal Antibody]

(a) Preparation of Monoclonal Antibody-Producing Cells

The polypeptide of the invention is aministered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens and the use of mice and rats is preferred.

In the preparation of the cells which produce monoclonal antibodies, an animal wherein the antibody titer is noted is selected from warm-blooded animals (e.g. mice) immunized with antigens, then spleen or lymph node is collected after two to five days from the final immunization and antibody-producing cells contained therein are fused with myeloma cells to give monoclonal antibody-producing hybridomas. Measurement of the antibody titer in antisera may, for example, be carried out by reacting a labeled ligand polypeptide or a labeled G protein-coupled receptor protein (which will be mentioned later) with the antiserum followed by measuring the binding activity of the labeling agent with the antibody. The operation for fusing may be carried out, for example, by a method of Koehler and Milstein (Nature, 256, 495, 1975), Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10-80% followed by incubating at 20-40° C.(preferably, at 30-37° C.) for one to ten minutes, an efficient cell fusion can be carried out.

Various methods may be applied for screening a hybridoma which produces anti-ligand polypeptide antibody or anti-G protein-coupled receptor antibody. For example, a supernatant liquid of hybridoma culture is added to a solid phase (e.g. microplate) to which the ligand polypeptide antigen or the G protein-coupled receptor protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then anti-ligand polypeptide monoclonal antibodies or anti-G protein-coupled receptor monoclonal antibodies bound on the solid phase are detected; or a supernatant liquid of the hybridoma culture is added to the solid phase to which anti-immunoglobulin or protein A is adsorbed, then the polypeptide of the invention labeled with a radioactive substance or an enzyme is added and anti-polypeptide or monoclonal antibodies bonded with the solid phase is detected.

Selection and cloning of the anti-polypeptide monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1-20% (preferably 10-20%) of fetal calf serum (FCS), a GIT medium (Wako Pure Chemical, Japan) containing 1-20% of fetal calf serum and a serum-free medium for hybridoma culturing (SFM-101; Nissui Seiyaku, Japan). The culturing temperature is usually 20-40° C. and, preferably, about 37° C. The culturing time is usually from five days to three weeks and, preferably, one to two weeks. The culturing is usually carried out in 5% carbon dioxide gas. The antibody titer of the supernatant liquid of the hybridoma culture may be measured by the same manner as in the above-mentioned measurement of the antibody titer of the anti-polypeptide in the antiserum.

(b) Purification of the Monoclonal Antibody

Like in the separation/purification of conventional polyclonal antibodies, the separation/purification of the anti-polypeptide monoclonal antibody may be carried out by methods for separating/purifying immunoglobulin such as salting-out, precipitation with an alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

The polypeptide antibody which is manufactured by the aforementioned method (a) or (b) is capable of specifically recognizing the polypeptide and, accordingly, it can be used for a quantitative determination of the polypeptide in test liquid samples and particularly for a quantitative determination by sandwich immunoassays.

Thus, the present invention provides, for example, the following methods:

(i) a quantitative determination of a polypeptide of the invention in a test liquid sample, which comprises
  (a) competitively reacting the test liquid sample and a labeled polypeptide of the invention with an antibody which reacts with the ligand polypeptide or the G protein-coupled receptor, and
  (b) measuring the ratio of the labeled polypeptide of the invention binding with said antibody; and (ii) a quantitative determination of a polypeptide of the invention in a test liquid sample, which comprises
  (a) reacting the test liquid sample with an antibody immobilized on an insoluble carrier and a labeled antibody simultaneously or continuously, and
  (b) measuring the activity of the labeling agent on the insoluble carrier wherein one antibody is capable of recognizing the N-terminal region of the polypeptide of the invention while another antibody is capable of recognizing the C-terminal region of the polypeptide of the invention.

When the monoclonal antibody of the present invention recognizing a polypeptide of the invention is used, the polypeptide of the invention can be measued and, moreover, can be detected by means of a tissue staining, etc. as well. For such an object, antibody molecules per se may be used or F(ab')$_2$' Fab' or Fab fractions of the antibody molecule may be used too. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of polypeptide of the invention, etc. in the liquid sample to be measured, is detected by a chemical or a physical means and then calculated using a standard curve prepared by a standard solution containing the known amount of antigen. For exmaple, nephrometry, competitive method, immunometric method and sanwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are [$^{125}$I], [$^{131}$I], [$^{3}$H] and [$^{14}$C]; preferred examples of the enzyme are those which are stable and with big specific activity, such as β-galactosidase, β-glucosidase, alkali phosphatase, peroxidase and malate dehydrogenase; examples of the fluorescent substance are fluorescamine, fluorescein isothiocyanate, etc.; and examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized anti-polypeptide antibody (the first reaction), then it is made to react with a labeled anti-polypeptide antibody (the second reaction) and the activity of the labeling agent on the insoluble carrier is measued whereupon the amount of the polypeptide of the invention receptor in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring polypeptide of the invention by the sandwich method of the present invention, the preferred anti-polypeptide antibodies used for the first and the second reactions are antibodies wherein their sites binding to the polypeptide of the invention are different each other. Thus, the antibodies used in the first and the second reactions are those wherein, when the antibody used in the second reaction recognizes the C-terminal region of the polypeptide of the invention, then the antibody recognizing the site other than C-terminal regions, e.g. recognizing the N-terminal region, is preferably used in the first reaction.

The anti-polypeptide antibody of the present invention may be used in a measuring system other than the sandwich method such as a competitive method, an immunometric method and a naphrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a competitive reaction with a certain amount of a labeled antibody followed by separating into solid and liquid phases; or the antigen in the test solution and an excess amount of labeled antibody are made to react, then a immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the polypeptide of the invention may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

As such, the amount of the polypeptide of the invention proteins can now be determined with a high precision using the anti-polypeptide antibody of the present invention.

Therefore, the antibody of the present invention can be used for diagnosis of diseases such as, dementia, depression, hyperactive child syndrome (microencephalopathy), disturbance of consciousness, anxiety disorder, schizophrenia, phobia, growth hormone secretory disorder, hyperphagia, polyphagia, hypercholesterolemia, hyperglyceridemia, hyperlipemia, hyperprolactinemia, diabetes mellitus, cancer, pancreatitis, diseases of kidney, Turner's syndrome, neurosis, rheumatoid arthritis, spinal injury, transient brain ischemia, amyotrophic lateral sclerosis, acute myocardial infarction, spinocerebellar degeneration, bone fracture, wounds, atopic dermatitis, osteoporosis, asthma, epilepsy, sterility, arteriosclerosis, pulmonary emphysema, pulmonary edema, galactorrhea, AIDS, and so on.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

| | |
|---|---|
| DNA | Deoxyribonucleic acid |
| cDNA | Complementary deoxyribonucleic acid |
| A | Adenine |
| T | Thymine |
| G | Guanine |
| C | Cytosine |
| Y | Thymine or Cytosine |
| N | Thymine, Cytosine, Adenine or Guanine |
| R | Adenine or Guanine |
| M | Cytosine or Adenine |
| W | Thymine or Adenine |
| S | Cytosine or Guanine |
| RNA | Ribonucleic acid |
| mRNA | Messenger ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| EDTA | Ethylenediamine tetraacetic acid |
| SDS | Sodium dodecyl sulfate |
| EIA | Enzyme Immunoassay |
| G, Gly | Glycine (or Glycyl) |
| A, Ala | Alanine (or Alanyl) |
| V, Val | Valine (or Valyl) |
| L, Leu | Leucine (or Leucyl) |
| I, Ile | Isoleucine (or Isoleucyl) |
| S, Ser | Serine (or Seryl) |
| T, Thr | Threonine (or Threonyl) |
| C, Cys | Cysteine (or Cysteinyl) |
| M, Met | Methionine (or Methionyl) |
| E, Glu | Glutamic acid (or Glutamyl) |
| D, Asp | Aspartic acid (or Aspartyl) |
| K, Lys | Lysine (or Lysyl) |
| R, Arg | Arginine (or Arginyl) |
| H, His | Histidine (or Histidyl) |
| F, Phe | Phenylalamine (or Phenylalanyl) |
| Y, Tyr | Tyrossine (or Tyrosyl) |
| W, Trp | Tryptophan (or Tryptophanyl) |
| P, Pro | Proline (or Prolyl) |
| N, Asn | Asparagine (or Asparaginyl) |
| Q, Gln | Glutamine (or Glutaminyl) |
| pGlu | Pyroglutamic acid (or Pyroglutamyl) |
| Me | Methyl |
| Et | Ethyl |
| Bu | Butyl |
| Ph | Phenyl |
| TC | Thiazolidinyl-4 (R)-carboxamide |
| Bom | Benzyloxymethyl |
| NMP | N-methyl pyrrolidone |
| PAM | Phenylacetoamidomethyl |

In this specification, substitutions, protective groups and reagents commonly used are indicated by the following abbreviations:

| | |
|---|---|
| Tos | p-toluenesulfonyl |
| HONB | N-hydroxy-5-norbornene-2,3-dicarboxyimide |
| OcHex | cyclohexyl ester |
| Bzl | benzyl |
| Z | benzyloxycarbonyl |
| Br-Z | 2-bromobenzyloxycarbonyl |
| Cl-Z | 2-chlorobenzyloxycarbonyl |
| Boc | t-butoxycarbonyl |
| HOBt | 1-hydroxybenztriazole |
| DCC | N,N'-dicyclohexylcarbodiimide |
| TFA | trifluoro acetic acid |
| Fmoc | N-9-fluorenylmethoxycarbonyl |
| DNP | dinitrophenyl |
| Bum | t-butoxymethyl |
| Trt | trityl |
| MeBzl | 4-methylbenzyl |

Each SEQ ID NO set forth in the SEQUENCE LISTING of the specification refers to the following sequence:

[SEQ ID NO:1] is an amino acid sequence of the bovine ligand polypeptide (17 amino acids from the N-terminus).

[SEQ ID NO:2] is an entire nucleotide sequence encoding the polypeptide comprising the amino acid sequence represented by SEQ ID NO:1.

[SEQ ID NO:3] is an entire amino acid sequence of the G protein-coupled receptor protein (APJ) encoded by the cDNA of the G protein-coupled receptor protein (APJ).

[SEQ ID NO:4] is an entire nucleotide sequence of the G protein-coupled receptor protein (APJ) cDNA.

[SEQ ID NO:5] is a synthetic DNA primer for screening of cDNA coding for the G protein-coupled receptor protein.

[SEQ ID NO:6] is a synthetic DNA primer for screening of cDNA coding for the G protein-coupled receptor protein.

[SEQ ID NO:7] is a synthetic DNA primer for screening of cDNA coding for the G protein-coupled receptor protein.

[SEQ ID NO:8] is a synthetic DNA primer for screening of cDNA coding for the G protein-coupled receptor protein.

[SEQ ID NO:9] is a synthetic DNA primer for screening of cDNA coding for the mouse ligand polypeptide.

[SEQ ID NO:10] is a synthetic DNA primer for screening of cDNA coding for the mouse ligand polypeptide.

[SEQ ID NO:11] is a synthetic DNA primer for screening of cDNA coding for the mouse ligand polypeptide.

[SEQ ID NO:12] is a synthetic DNA primer for screening of cDNA coding for the mouse ligand polypeptide.

[SEQ ID NO:13] is a synthetic DNA primer for screening of cDNA coding for the mouse ligand polypeptide.

[SEQ ID NO:14] is a synthetic DNA primer for screening of cDNA coding for the mouse ligand polypeptide.

[SEQ ID NO:15] is an amino acid sequence encoded by the cDNA of the mouse ligand polypeptide.

[SEQ ID NO:16] is a nucleotide sequence coding for the cDNA of the mouse ligand polypeptide.

[SEQ ID NO:17] is a synthetic DNA primer for screening of cDNA coding for the bovine ligand polypeptide.

[SEQ ID NO:18] is a synthetic DNA primer for screening of cDNA coding for the bovine ligand polypeptide.

[SEQ ID NO:19] is a synthetic DNA primer for screening of cDNA coding for the rat ligand polypeptide.

[SEQ ID NO:20] is a synthetic DNA primer for screening of cDNA coding for the rat ligand polypeptide.

[SEQ ID NO:21] is a synthetic DNA primer for screening of cDNA coding for the rat ligand polypeptide.

[SEQ ID NO:22] is a synthetic DNA primer for screening of cDNA coding for the rat ligand polypeptide.
[SEQ ID NO:23] is a synthetic DNA primer for screening of cDNA coding for the human ligand polypeptide.
[SEQ ID NO:24] is a synthetic DNA primer for screening of cDNA coding for the human ligand polypeptide.
[SEQ ID NO:25] is a synthetic DNA primer for screening of cDNA coding for the human ligand polypeptide.
[SEQ ID NO:26] is a synthetic DNA primer for screening of cDNA coding for the human ligand polypeptide.
[SEQ ID NO:27] is a synthetic DNA primer for screening of cDNA coding for the human ligand polypeptide.
[SEQ ID NO:28] is a synthetic DNA primer for screening of cDNA coding for the human ligand polypeptide.
[SEQ ID NO:29] is a synthetic DNA primer for screening of cDNA coding for the human ligand polypeptide.
[SEQ ID NO:30] is a synthetic DNA primer for screening of cDNA coding for the human ligand polypeptide.
[SEQ ID NO:31] is a synthetic DNA primer for screening of cDNA coding for the bovine ligand polypeptide.
[SEQ ID NO:32] is a synthetic DNA primer for screening of cDNA coding for the bovine ligand polypeptide.
[SEQ ID NO:33] is a synthetic DNA primer for screening of cDNA coding for the bovine ligand polypeptide.
[SEQ ID NO:34] is a synthetic DNA primer for screening of cDNA coding for the bovine ligand polypeptide.
[SEQ ID NO:35] is a synthetic DNA primer for screening of cDNA coding for the bovine ligand polypeptide.
[SEQ ID NO:36] is a synthetic DNA primer for screening of cDNA coding for the bovine ligand polypeptide.
[SEQ ID NO:37] is a synthetic DNA primer for screening of cDNA coding for the bovine ligand polypeptide.
[SEQ ID NO:38] is an amino acid sequence encoded by the cDNA of the rat ligand polypeptide.
[SEQ ID NO:39] is a nucleotide sequence coding for the cDNA of the rat ligand polypeptide.
[SEQ ID NO:40] is an amino acid sequence encoded by the cDNA of the human ligand polypeptide.
[SEQ ID NO:41] is a nucleotide sequence coding for the cDNA of the human ligand polypeptide.
[SEQ ID NO:42] is an amino acid sequence encoded by the cDNA of the bovine ligand polypeptide.
[SEQ ID NO:43] is a nucleotide sequence coding for the cDNA of the bovine ligand polypeptide.

The transformant *Escherichia coli*, designated JM109/pmA10L-13, which is obtained in the Example 11 mentioned herein below, is on deposit under the terms of the Budapest Treaty from Dec. 22, 1997, with the National Institute of Bioscience and Human-Technology (NIBH), Agency of Industrial Science and Technology, Ministry of International Trade and Industry, Japan and has been assigned the Accession Number FERM BP-6214.

The transformant *Escherichia coli*, designated JM109/prSHe-1, which is obtained in the Example 13 mentioned herein below, is on deposit under the terms of the Budapest Treaty from Jan. 20, 1998, with NIBH and has been assigned the Accession Number FERM BP-6228.

The transformant *Escherichia coli*, designated JM109/phSuN-4, which is obtained in the Example 14 mentioned herein below, is on deposit under the terms of the Budapest Treaty from Jan. 20, 1998, with NIBH and has been assigned the Accession Number FERM BP-6229.

The transformant *Escherichia coli*, designated JM109/pBovA10prec24, which is obtained in the Example 15 mentioned herein below, is on deposit under the terms of the Budapest Treaty from Jan. 20, 1998, with NIBH and has been assigned the Accession Number FERM BP-6230.

The transformant *Escherichia coli*, designated BL21 (DE3)/pTB960-13, which is obtained in the Example 35 mentioned herein below, is on deposit under the terms of the Budapest Treaty from Dec. 2, 1998, with NIBH and has been assigned the Accession Number FERM BP-6590 and with the Fermentation Institute, Osaka as of Nov. 11, 1998 under the accession number IFO 16220.

BEST MODE FOR CARRYING OUT THE PRESENT INVENTION

The following examples are intended to describe the present invention in further detail and should by no means be interpretated as defining the scope of the present invention.

REFERENCE EXAMPLE 1

Production of Synthetic DNA Primers for Amplifying a DNA Coding for the G Protein-Coupled Receptor Protein The nucleotide sequences of the cDNAs respectively coding for amino acid sequences in the vicinity of the first transmembrane domain of known human-derived TRH receptor protein (HTRHR), human-derived RANTES receptor protein (L10918, HUMRANTES), human Burkitt's lymphoma-derived unknown-ligand receptor protein (X68149, HSBL-RIA), human-derived somatostatin receptor protein (L14856, HUMSOMAT), rat-derived μ-opioid receptor protein (U02083, RNU02083), rat-derived κ-opioid receptor protein (U00442, U00442), human-derived neuromedin B receptor protein (M73482, HUMNMBR), human-derived muscarinergic acetylcholine receptor protein (X15266, HSHM4), rat-derived adrenaline α 1B receptor protein (L08609, RATAA-DRE01), human-derived somatostatin 3 receptor protein (M96738, HUMSSTR3X), human-derived C5a receptor protein (HUMC5AAR), human-derived unknown-ligand receptor protein (HUMRDC1A), human-derived unknown-ligand receptor protein (M84605, HUMOPIODRE), and rat-derived adrenaline α 2B receptor protein (M91466, RATA2BAR) were compared with one another, and a segment with high similarity was found out.

Separately, the nucleotide sequences of the cDNAs respectively coding for amino acid sequences in the vicinity of the sixth transmembrane domain of known mouse-derived unknown-ligand receptor protein (M80481, MUSGIR), human-derived bombesin receptor protein (L08893, HUMBOMB3S), human-derived adenosine A2 receptor protein (S46950, S46950), mouse-derived unknown-ligand receptor protein (D21061, MUSGPCR), mouse-derived TRH receptor protein (S43387, S43387), rat-derived neuromedin K receptor protein (J05189, RATNEURA), rat-derived adenosine A1 receptor protein (M69045, RATA1ARA), human-derived neurokinin A receptor protein (M57414, HUMNEKAR), rat-derived adenosine 3A receptor protein (M94152, RATADENREC), human-derived somatostatin 1 receptor protein (M81829, HUMSRI1A), human-derived neurokinin 3 receptor protein (S86390, S86371S4), rat-derived unknown-ligand receptor protein (X61496, RNCG-PCR), human-derived somatostatin 4 receptor protein (L07061, HUMSSTR4Z) and rat-derived GnRH receptor protein (M31670, RATGNRHA) were compared with one another, and a segment with high similarity was found out.

The codes or abbreviations given above in the parentheses are serial numbers shown upon protein searching in the GenBank/EMBL Data Bank using the DNASIS Gene/Protein sequence data base (CD019, Hitachi Software Engineering)

and in general called accession number and entry name, respectively, except for HTRHR, which refers to the sequence described in Japanese Kokai Tokkyo Koho H07-304797.

Particularly, a plan was made for introducing mixed nucleotides using the nucleotide sequence common to cDNAs coding for many receptor proteins as the base and seeking for an increased homology to as many receptor cDNAs as possible in the remainders of their sequences as well. Accordingly, two synthetic DNAs having sequences complementary to the common nucleotide sequence, namely the sequences defined under SEQ ID NO:5 and SEQ ID NO:6, were synthesized.

[Synthetic DNAs]

(SEQ ID NO:5)
5'-CGTGG(G or C)C(A or C)T(G or C) (G or C) TGGGCAAC(A, G, C or T) (C or T) CCTG-3'

(SEQ ID NO:6)
5'-GT(A, G, C or T)G(A or T) (A or G) (A or G) GGCA(A, G, C or T)CCAGCAGA(G or T)GGCAAA-3'

On the occasion of synthesis, the plurality of nucleotides given in the parentheses are used in admixture in the corresponding step of synthesis.

EXAMPLE 1

Amplification of G Protein-Coupled Receptor Protein cDNA by PCR Using Human Amygdala-Derived cDNA Using human amygdala-derived cDNA (QuickClone, Clontech) as the template, amplification was carried out by the PCR technique using the DNA primers synthesized in Reference Example 1. The composition of the reaction mixture was as follows: synthetic DNA primers (sequences: 5' primer sequence and 3' primer sequence) 1 µM each, template cDNA 1 ng, 0.25 mM dNTPs, Taq DNA polymerase 1 µl and buffer attached to the enzyme, the total reaction mixture volume being 100 µl. Amplification was carried out using Thermal Cycler (Perkin Elmer) in 30 cycles each comprising 30 seconds at 96° C., 1 minute at 45° C., and 3 minutes at 60° C. Prior to addition of Taq DNA polymerase, the remaining components of the reaction mixture were mixed up and heated at 95° C. for 5 minutes and at 65° C. for 5 minutes. Amplification product confirmation was performed by 1.2% agarose gel electrophoresis and ethidium bromide staining.

Using a portion (1 µl) of the reaction product after PCR, the DNA amplified was subcloned into the plasmid vector pCR™II (TM refers to registered trademark) according to the prescription for the TA cloning kit (Invitrogen). The subcloning product was introduced into *Escherichia coli* INV α F' competent cells (Invitrogen) for transformation. Clones with the insert cDNA fragment were selected on LB agar medium containing ampicillin and X-gal, and only those clones showing a white color which is an indicator of a transformant were isolated with sterilized toothpicks. A number of transformants were thus obtained. Each clone was cultured overnight on ampicillin-containing LB medium and the plasmid DNA was prepared using an automated plasmid extractor (Kurabo). A portion of the thus-prepared DNA was cleaved with EcoRI for confirming the size of the insert cDNA. A portion of the remaining DNA was further concentrated by subjecting it to RNase treatment, phenol-chloroform extraction and ethanol precipitation. The reaction for determining the nucleotide sequence was carried out using a DyeDeoxy Terminator Cycle Sequencing Kit (ABI), interpretation was effected using an automated fluorescent sequencer, and the nucleotide sequence information obtained was processed using DNASIS (Hitachi System Engineering).

Based on the results of nucleotide sequence analysis, a clone, *E. coli* INV α F'/pA10, with a PCR product cDNA corresponding to the 1st to 6th transmembrane domains of the APJ receptor, one of the G protein-coupled receptors, as inserted therein, was found out from among a number of transformants.

The nucleotide sequence corresponds to the segment from the 318th to 993rd nucleotide of the nucleotide sequence of the APJ receptor gene as reported by O'Dowd, B. F. et al. (Gene, vol. 136, pp. 355-360, 1993). Since, however, it is a PCR product obtained by using modified primers, the sequences of the primer portions are different from the corresponding sequences of APJ and, in addition, it is deficient in N and C termini.

EXAMPLE 2

Cloning of a cDNA Containing the Full-Length Coding Region of the Receptor Protein from a Human Amygdala-Derived cDNA Library For obtaining a DNA coding for the full-length APJ receptor, a human amygdala-derived cDNA library was screened using the APJ receptor cDNA fragment obtained in Example 1 as a probe. The human amygdala-derived cDNA library used was Clontech's library (Clontech, CLHL30086) in which the λ gt11 phage vector is used. An amount of the human amygdala cDNA library corresponding to $2 \times 10^6$ pfu (plaque-forming units) was admixed with magnesium sulfate-treated *Escherichia coli* Y1090⁻. After 15 minutes of incubation at 37° C., 0.5% agarose (Pharmacia) LB was added, and 1.5% agar (Wako Pure Chemical) LB plates (containing 50 µg/ml ampicillin) were seeded with the resulting mixture. After overnight culture at 42° C., a nitrocellulose filter was placed on each plate with plaques formed thereon, for plaque transfer onto the filter. This filter was subjected to alkali treatment for denaturation and, then, DNA fixation was effected by heating at 80° C. for 3 hours.

This filter was incubated overnight at 42° C. with the probe mentioned below in a buffer containing 50% formamide, 4×SSPE, 5× Denhardt's solution, 0.1% SDS and 100 µg/ml salmon sperm DNA, for hybridization. The probe used was prepared by cleaving the DNA fragment inserted into the plasmid pA10 obtained in Example 1 with EcoRI and, after recovering, causing [$^{32}$P]dCTP (du Pont) to be taken up using a random prime DNA labeling kit (Amersham). Washing was performed with 2× SSC plus 0.1% SDS at 55° C. for 1 hour and then autoradiography was carried out at −80° C. for detecting hybridizing plaques.

As a result of the above screening, four independent phage clones showed a hybridization signal. DNA was prepared from each of these four clones, digested with EcoRI and, after agarose gel electrophoresis, analyzed by Southern blotting using the same probe as used in the screening. The clones gave hybridizing bands corresponding to about 1.2 kb, 1.2 kb, 1.3 kb and 1.6 kb, respectively. Among them, the clone that gave a band of about 1.6 kb was selected (λ34). The phage DNA of λ34 was prepared and an EcoRI fragment thereof with a hybridizing size was subcloned into the plasmid pUC118 at the EcoRI site. This plasmid was used to transform *Escherichia coli* JM109 to give a transformant, *E. coli* JM109/pUC118-λ34. The nucleotide sequence of this plasmid was determined by the same method as shown in Example 1, whereby it was found that said plasmid contains a DNA coding for the full length of the G protein-coupled receptor protein (APJ). The amino acid sequence encoded was identical with that reported by O'Dowd, B. F. et al. (Gene, vol. 136, pp. 355-360, 1993). (GenBank accession number: U03642) The DNA sequence and amino acid sequence are shown in FIG. 1.

EXAMPLE 3

Detection, by Northern Hybridization, of Expression and Distribution of the APJ Receptor mRNA in Human Tissues For detecting the expression, on the mRNA level, of APJ encoded by the plasmid pUC118-λ34 obtained in Example 2 in human tissues, Northern blotting was carried out. The filters used for Northern blot were Human MTN Blot I and II (CL7760-1, CL7759-1), and the probe used was the same one as used in Example 1. Hybridization was effected by incubating the above-mentioned filters and probe overnight at 42° C. in a buffer containing 50% formamide, 5×SSPE, 10× Denhardt's solution, 2% SDS and 100 µg/ml salmon sperm DNA. The filters were washed with 0.1×SSC plus 0.1% SDS at 50° C. and, after air drying, X ray films (XAR5, Kodak) were exposed thereto at −80° C. for 3 days. The results are shown in FIG. 2. From FIG. 2, it was revealed that the receptor gene encoded by pUC118-λ34 is expressed in human heart, brain, placenta, liver, skeletal muscle, kidney, pancreas, spleen, thymus, prostate gland, ovary, small intestine and large intestine. In particular, it is strongly expressed in spleen, heart and placenta.

EXAMPLE 4

Production of CHO Cells for APJ Receptor Expression

The cDNA fragment encoded in pUC118-λ34 had a 5' untranslated region of about 0.2 kb, hence it was considered advisable that, for increasing the expression efficiency, said portion be removed as far as possible. It was also necessary to add restriction enzyme sites corresponding to the cloning site of the expression vector to both ends of the cDNA portion. Therefore, two cDNA fragments (5' side and 3' side) were separately treated as mentioned below and inserted into the animal cell expression vector pAKKO-111H at a site downstream from the SRα promoter to construct pAKKO-A10. Thus, pUC118-λ34 was cleaved at the two BstXI sites each uniquely occurring in the 5' untranslated region and the coding region, the termini were repaired using T4 DNA polymerase, and a SalI linker was added thereto by ligation. After SalI-SacI double digestion, a fragment of about 0.6 kb was separated by electrophoresis and recovered. Then, the cDNA portion inserted in pUC118-λ34 was cleaved at both ends thereof by EcoRI digestion, the termini were repaired using T4 DNA polymerase, and a ClaI linker was added thereto by ligation. For distinguishing from the fragment corresponding to the 5'-terminal portion, EcoRV digestion was carried out and ClaI-SacI double digestion was further performed, and a fragment of about 0.8 kb was recovered by electrophoresis. Furthermore, the expression vector pAKKO-111H for use in animal cells was digested at the SalI and ClaI restriction enzyme sites, which are multicloning sites and then electrophoresed, and the vector portion was recovered. The 5' side and 3' side fragments of the APJ receptor cDNA and the expression vector, each prepared as mentioned above, were joined together by ligation, and the ligation mixture was used to transform *Escherichia coli* DH5 to give *E. coli* DH5/pAKKO-A10.

The transformant *E. coli* DH5/pAKKO-A10 was cultured and the DNA of the plasmid pAKKO-A10 as prepared in large amounts.

A 20-µg portion of said plasmid DNA was dissolved in 1 ml of physiological saline (PBS), the solution was poured into a Gene Transfer (Wako Pure Chemical) vial and violently stirred using a vortex mixer, whereby a DNA-containing liposome phase was formed. Cell culture dishes with a diameter of 35 mm were seeded with 1 to 2×10$^6$ CHO dhfr$^-$ cells and, after 20 hours of cultivation, the medium was exchanged for a fresh portion. An amount (25 µl) corresponding to 0.5 µg of DNA of the liposome phase was added dropwise to each dish and introduction of the plasmid DNA was effected by 16 hours of incubation. After further medium exchange for a fresh portion, cultivation was carried out for 1 day, then the medium was exchanged for a selection medium, and cultivation was continued for 3 days. Finally, the cells were dispersed by trypsinization and sown, at a low density, into a selection medium (deoxyribonucleoside- and ribonucleoside-free minimum essential medium, alpha medium supplemented with 10% dialyzed fetal bovine serum), and transformant selection was carried out. Transformants alone can grow in the selection medium. Selection was repeated by repeating subculture, and a cell line, CHO-A10, was established.

EXAMPLE 5

Confirmation, on the Transcription Level, of the Expression of the Full-Length Receptor Protein in the Cell Line CHO-A10

Using a Fast Track kit (Invitrogen), poly(A)$^+$ RNA was prepared from CHO-A10 cells and from CHO cells (control cells) according to the prescription for the kit. Using 0.02 µg of this poly(A)$^+$ RNA, together with an RNA PCR kit (Takara Shuzo), cDNA synthesis was carried out. The primers used were random nonamers and the total volume of the reaction mixture was 40 µl. As a negative control for the cDNA synthesis, a reaction mixture was also prepared without adding reverse transcriptase. First, the reaction was allowed to proceed until a certain extent of elongation from the primers by 10 minutes of incubation at 30° C. Then, the reverse transcription reaction was allowed to proceed to a sufficient extent by 30 minutes of incubation at 42° C., the enzyme was then inactivated by 5 minutes of heating at 99° C., and the mixture was further cooled at 5° C. for 5 minutes.

After completion of the reverse transcription reaction, a part of the reaction mixture was recovered, diluted with distilled water and subjected to phenol/chloroform extraction and diethyl ether extraction. The precipitate obtained upon ethanol precipitation was dissolved in a predetermined amount of distilled water and the solution was used as the cDNA sample. Serial dilutions of this cDNA solution and of the plasmid DNA (pAKKO-A10) were prepared and subjected to PCR, which was carried out using primers specific to the full-length receptor protein. The primers prepared based on the nucleotide sequence of the coding region for the full-length receptor protein had the following sequences, respectively:

```
5'-CAGACAACCAGTCTGAGTGTGAGT-3'    (SEQ ID NO:7)

5'-ATGGATTTCTCGTGCATCTGTTCT-3'    (SEQ ID NO:8)
```

Figure 3:
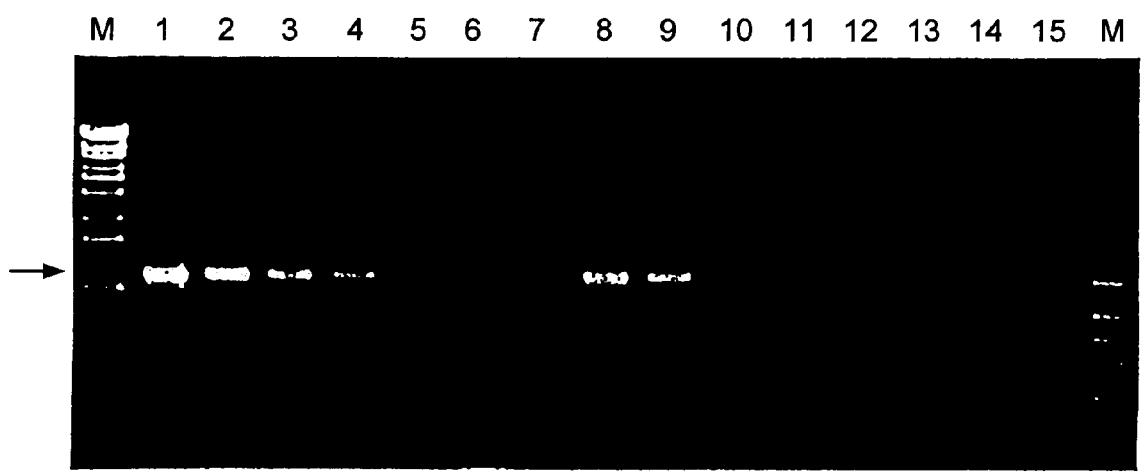
FIG. 3 shows the confirmed expression, on the transcription level, of the full-length receptor protein in the cell line CHO-A10.

The PCR reaction was carried out using 1 μM each primer, 0.5 μl of Taq DNA polymerase (Takara Shuzo), the reaction buffer and dNTPs attached to the enzyme, and 10 μl of the template DNA (cDNA or plasmid solution); the total volume was 100 μl. Initially, the template DNA was sufficiently denatured by 2 minutes of heat treatment at 94° C. and then the reaction was carried out in 25 cycles each comprising 30 seconds at 95° C., 30 seconds at 65° C. and 60 seconds at 72° C. After completion of the reaction, 10 μl of the reaction mixture was subjected to agarose gel electrophoresis, for detection of amplification products and quantitative comparison thereof. As a result, a PCR product having a size (about 1.1 kb) estimated from the sequence of the cDNA coding for the full-length receptor protein was detected (FIG. 3). No specific band was detected in the lane for the PCR reaction mixture in which the reverse transcription product obtained without adding reverse transcriptase was used as the template; this fact excluded the possibility of the product in question being a PCR product derived from the genomic DNA of the CHO cells. Further, no specific band appeared in the lane for the control cells, whereby it was confirmed that the product in question was not derived from the mRNA originally expressed in CHO cells (FIG. 3).

EXAMPLE 6

Detection, by Means of a Cytosenser, of an Activity Contained in Tissue Extracts and Specifically Stimulating CHO-A10 Cells Extracts were prepared from bovine stomach, swine small intestine and swine brain essentially as described below, frozen stored and used as samples for screening for a cell stimulating activity.

Each tissue, boiled and disrupted, was extracted with 0.5 M acetic acid, and the extract was filtered and allowed to be adsorbed on arginic acid, followed by elution with 0.2 M hydrochloric acid. The substance contained in the eluate fraction was collected by salting out, washed with methanol and dried under vacuum. This was again dissolved in distilled water and, after adjustment of pH to 7.2, two volumes of ethanol was added, and the resulting precipitate was collected by filtration. This was again dissolved in distilled water, the pH was adjusted to 4.2, the resulting precipitate was removed, and the filtrate was lyophilized. This lyophylizate was dissolved in 0.2 M acetic acid and subjected to gel filtration on a Sephadex G-25 column for fractionation. Each fraction was lyophilized.

Separately, bovine hypothalamus was boiled and disrupted, and extracted with 1 M acetic acid. The extract was centrifuged, 0.05% TFA was added to the supernatant, and the mixture was passed through a C18 column for adsorption, followed by stepwise elution with 10%, 30% and 50% acetonitrile. Each eluate was adjusted to 20 mM ammonium acetate-10% acetonitrile (pH 4.5) and applied to a CM Sepharose cation exchange column (HiPrep CM Sepharose FF, Pharmacia) for adsorption. Eluate fractions obtained by using 100 mM, 250 mM, 500 mM and 1,000 mM ammonium acetate as well as the effluent fraction were concentrated and desalted using a Sep-Pak C18 column and then lyophilized. The lyophilizates thus obtained were used as samples for cell stimulating activity screening.

The cell stimulating activity was measured using a Cytosensor (Molecular Devices) with the change in extracellular pH as an indicator. CHO-A10 cells or control cells were dispersed by trypsinization and cell suspensions containing $3 \times 10^5$ cells/ml were prepared. These were distributed in 0.9-ml portions into capsules for the Cytosensor and cultured overnight. Each cell-containing capsule was transferred to the sensor chamber, which was further set in the work station of the Cytosensor. Using the built-in pump of the Cytosensor, the states of pump ON (1 minute and 20 seconds) and pump OFF (40 seconds) were repeated alternately and the change in extracellular pH between 8 seconds after pump OFF and 38 seconds after pump OFF (in 30 seconds) was measured for the calculation of the rate of pH change in each cycle. After acclimatization of the cells until stabilization of the rate of pH change (about 2 hours), the sample dissolved in the medium for the Cytosensor was set in one of the two channels. By channel changing, the cells were exposed to the sample-containing medium for 7 minutes and 2 seconds and the change in rate of extracellular pH change was measured.

Distilled water (1 ml) was added to 10 mg of each of the purified and lyophilized tissue extracts prepared from bovine stomach, swine small intestine and swine brain by the method mentioned above. The insoluble matter was removed by centrifugation, and the supernatant was added, in a 1/40 volume ratio, to low-buffered RPMI 1640 medium for the Cytosensor as supplemented with 0.1% bovine serum albumin (Sigma, A-2153, fraction V), to give a sample for measurement (final concentration 0.25 mg/ml). Considering the possibility of some samples markedly changing the pH of the medium, pH adjustment was carried out with the color of phenol red contained in the medium as an indicator. This sample was administered to CHO-A10 cells and to control cells and, with the difference in cell reaction as an indicator, screening was performed for samples containing a cell stimulating activity. As regards the samples separated and purified by chromatography, each sample was dissolved in a small amount of DMSO and then dissolved in low buffered RPMI 1640 medium for the Cytosensor as supplemented with 0.1% bovine serum albumin (Sigma, A-2153, fraction V), for attaining improved dissolution efficiency. In this case, the same amount (0.2%) of DMSO was also added beforehand to the sample-free medium, for cell acclimatization thereto.

As a result of cell stimulating activity measurements with the samples prepared form bovine stomach, swine small intestine and swine brain as mentioned above, with the change in the rate of extracellular pH change as an indicator, samples (B3, B4, S1, S2, S3, S4, G4, G6) capable of specifically activating (increasing the rate of extracellular pH change) CHO cells with the APJ receptor introduced therein (CHO-A10) as compared with the control cells, as shown in FIG. 4 and FIG. 5, were found out. As a result of the same measurements with samples prepared from bovine hypothalamus, a specific cell stimulating activity (extracellular pH change rate enhancing activity) was detected in Fr. 10 (fraction obtained by adsorption of the 30% acetonitrile eluate fraction on the C18 column, followed by elution with 1,000 mM ammonium acetate), as shown in FIG. 6 and FIG. 7.

EXAMPLE 7

Selection of High-Level APJ Receptor Expression Cells with the Intensity of Cell Stimulating Activity as an Indicator CHO-A10 is a cell line established by repeating subculture, in a selection medium, of transformant cells obtained by introduction of the expression vector pAKKO-A10. Therefore, the copy number of the introduced cDNA may vary among individual cells, hence it is possible that the number of APJ receptors expressed on the cell might be different. If a cell line capable of high expression of the functional receptor is established from among such a population, assay results will expectedly be obtained with high sensitivity and stability. For that reason, a portion of the active fraction prepared from bovine hypothalamus in the same manner as in the case of bovine stomach mentioned in Example 8 after reversed phase chromatography on RESOURCE RPC was collected and used as a standard sample. Using this, high amount of APJ receptor expressing cells were selected with the cell stimulating activity measured by a Cytosensor as an indicator. Eight independent clones were assayed for cell stimulating activity and remarkable cell stimulating activity was detected with clones 1, 3, 4 and 6, as shown in FIG. 8. From among these clones, No. 6 clone (CHO-A10, clone 6) was further cultured for use in the subsequent cell stimulating activity measurements.

EXAMPLE 8

Purification, from Bovine Stomach, of an Active Substance (Peptide) Capable of Specifically Enhancing the Rate of Change in Extracellular pH in the Cell Line CHO-A10

A typical example of the purification of an active substance capable of specifically enhancing the rate of change in extracellular pH in the cell line CHO-A10 from bovine rumen and reticulum is specifically mentioned in the following.

Bovine rumen (1.0 kg) and reticulum (1.0 kg) were cut to pieces and boiled in 4.0 L of distilled water for 20 minutes. After rapid cooling on ice, 280 ml of acetic acid was added to a final concentration of 1.0 M and the tissue pieces were homogenized with Polytron (12,000 rpm, 12 min.). The homogenate was stirred overnight and then centrifuged (9,500 rpm, 20 min.) to give a supernatant. The sediment was suspended in 2.0 L of 1.0 M acetic acid, homogenized with Polytron and centrifuged again to give a supernatant. Both supernatants were combined, TFA was added to a final concentration of 0.05%, and the resulting mixture was applied to a reversed phase C18 column (Prep C18 125 Å, 100 ml; Millipore). After application, the column was washed with 200 ml of 0.05% TFA/dH$_2$O (dH$_2$O hereinafter refers to distilled water) and then elution was carried out in 3 steps with 10%, 30% and 50% CH$_3$CN/0.05% TFA/dH$_2$O. Two volumes of 20 mM CH$_3$COONH$_4$/dH$_2$O was added to the 30% CH$_3$CN/0.05% TFA/dH$_2$O eluate fraction and the mixture was applied to a cation exchange column (HiPrep CM-Sepharose FF, 20 ml; Pharmacia). The column was washed with 20 mM CH$_3$COONH$_4$/10% CH$_3$CN/dH$_2$O and elution was then carried out in 4 steps with 100 mM, 200 mM, 500 mM and 1,000 mM CH$_3$COONH$_4$/10% CH$_3$CN/dH$_2$O. The 1,000 mM CH$_3$COONH$_4$ eluate fraction showed an activity which specifically enhanced the rate of change in extracellular pH in the cell line CHO-A10, hence 3 volumes of acetone was added to this eluate fraction and deproteinization and concentration by evaporation were conducted. TFA (final concentration 0.1%) was added to the concentrated fraction and the mixture was applied to a reversed phase column (RESOURCE RPC, 1 ml; Pharmacia). Concentration gradient elution was performed with 12.5%-20.0% CH$_3$CN. Two fractions eluted with 15.5%-16.5% and 17.0%-17.5% CH$_3$CN (active fractions P-1 and P-2, respectively) showed an activity which specifically enhanced the rate of change in extracellular pH in the cell line CHO-A10 (FIG. 9). Of the two active fractions separated, the 17.0%-17.5% CH$_3$CN eluate fraction (P-2) was lyophilized, then dissolved in DMSO and suspended in 0.1% TFA/dH$_2$O and applied to a reversed phase column (diphenyl 219TP5415; Vydac; or Sephasil C8 SC 2.1/10; Pharmacia).

In the case of diphenyl 219TP5415, concentration gradient elution was carried out with 14.0%-20.0% CH$_3$CN and an activity which specifically enhanced the rate of change in extracellular pH in the cell line CHO-A10 was detected in the 17.0% CH$_3$CN fraction (FIG. 10). In the case of Sephasil C8 SC 2.1/10, concentration gradient elution was carried out with 18.0%-24.0% CH$_3$CN and an activity which specifically enhanced the rate of change in extracellular pH in the cell line CHO-A10 was detected in the 19.5% CH$_3$CN fraction (FIG. 11). The active fractions from diphenyl 219TP5415 and Sephasil C8 SC 2.1/10 were respectively lyophilized, then dissolved in DMSO and suspended in 0.1% TFA/dH$_2$O and applied to a reversed phase column (µ RPC C2/C18 SC 2.1/10; Pharmacia). In the case of the diphenyl 219TP5415-derived active fraction, one peak eluted during the period of 19.0 to 20.5 minutes by uniform concentration elution with 16.0% CH$_3$CN and, in the case of the Sephasil C8 SC 2.1/10-derived active fraction, one peak eluted during the period of 18.0 to 20.0 minutes by uniform concentration elution with 16.0% CH$_3$CN had an activity detected which specifically enhanced the rate of change in extracellular pH in the cell line CHO-A10 (FIG. 12 and FIG. 13).

EXAMPLE 9

Amino Acid Sequence Determination of the Bovine Stomach-Derived Active Substance (Peptide) Capable of Specifically Enhancing the Rate of Change in Extracellular pH in the Cell Line CHO-A10

The amino acid sequence of the active peptide (P-2) purified in Example 8 and capable of specifically enhancing the rate of change in extracellular pH in the cell line CHO-A10 was determined. The two peak fractions derived from the reversed column p RPC C2/C18 SC 2.1/10 and identical in activity were lyophilized and subjected to amino acid sequence analysis on a peptide sequencer (ABI model 492). As a result, both peaks gave one and the same amino acid sequence (17 residues from the N terminus) (SEQ ID NO:1).

EXAMPLE 10

Identification of the Gene Fragment Coding for a Mouse-Derived Counterpart of the Bovine Stomach-Derived Peptide Fragment The bovine stomach-derived peptide fragment composed of 17 amino acid residues as obtained by the N-terminal amino acid analysis of the purification product of Example 9 was translated into a nucleotide sequence (SEQ ID NO:2) and homology searching was carried out in the Expressed Sequence Tag (EST) data base registered with the GenBank/EMBL using the gene sequence analysis software Gene Bright (Hitachi Software). As a result, a part of the sequence shown under SEQ ID NO:1 showed high homology to the amino acid sequence translated from a mouse-derived EST of unknown function registered under the accession number W33327 and it was found that said EST codes for the latter half downstream mouse type counterpart of the bovine stomach-derived 17-amino-acid peptide fragment (FIG. 14).

EXAMPLE 11

Full-Length Cloning of the Ligand Gene Coding for the Mouse Type Counterpart of the Bovine Stomach-Derived 17-Amino-Acid Peptide Fragment Obtained by N-Terminal Amino Acid Analysis in Example 9

Based on the sequence of EST obtained in Example 10, W33-F1 (5'-CTGGCAGGGAGGCAGGAGGAA-3') (SE ID NO:9), W33-F2 (5'-GCAGGAGGAAATTTCGCAGA-CAGC-3') (SEQ ID NO:10), W33-R1 (5'-GAAGAGAAT-TCATCTGTGGAGTA-3') (SEQ ID NO:11) and W33-R2 (5'-ACCGGCACCGGGAGGGCACTT-3') (SEQ ID NO:12) were respectively synthesized. Separately, total RNA was prepared from whole brain of BALB/C mouse using Isogen (Nippon Gene) and then poly(A)+ RNA was prepared therefrom using an oligo(dT) cellulose column (mRNA Purification Kit; Pharmacia), following the respective manuals. From 1 µg of the poly(A)+RNA prepared, double-stranded cDNA for use in rapid amplification of cDNA ends (RACE) was synthesized according to the manual for Marathon cDNA Amplification Kit (Clontech), and dissolved in 10 µl of distilled water. This was further diluted 50 times with TE buffer and, using the dilution as the template, the PCR was carried out. The reaction mixture was prepared by using EX Taq (Takara) as DNA polymerase, combining 2.5 µl of 10×EX Taq buffer attached, 1 µl of dNTP mixture (each 2.5 mM) and 0.5 µl of Ex Taq in admixture with an equal volume of TaqStart Antibody (Clontech), adding 0.5 µl of the adapter primer AP1 or AP2 (each 10 µM) attached to the Marathon cDNA Amplification Kit, 0.5 µl of the gene-specific primer W33-F1, W33-F2, W33-R1 or W33-R2 (each 10 µM) and the template cDNA, and making the volume 25 µl with distilled water. In the first RACE, 2.5 µl of the template cDNA solution was added to the reaction mixture, and W33-F1 and AP1 were combined for 3' RACE and W33-R1 and AP1 for 5' RACE. After 2 minutes of heat treatment at 94° C., the PCR was carried out in 5 cycles each comprising 10 seconds at 98° C. and 2 minutes at 72° C., then in 5 cycles each comprising 10 seconds at 98° C. and 2 minutes at 70° C. and further in 25 cycles each comprising 10 seconds at 98° C. and 2 minutes at 68° C. 2.5 µl of this first PCR product was used as the template for the second PCR. On that occasion, the primer combinations were changed, namely W33-F2 and AP2 were combined for 3' RACE and W33-R2 and AP2 for 5' RACE. After 2 minutes of heat treatment at 94° C., the PCR reaction was carried out in 5 cycles each comprising 10 seconds at 98° C. and 2 minutes at 72° C., then in 5 cycles each comprising 10 seconds at 98° C. and 2 minutes at 70° C. and in 30 cycles each comprising 10 seconds at 98° C. and 2 minutes at 68° C. The PCR product was subjected to 1.2% agarose electrophoresis and ethidium bromide staining. A band of about 300 bp (in the case of 3' RACE) or a band of about 600 bp (in the case of 5' RACE) was excised with a razor and subjected to centrifugal filtration using a filter (UltraFree; Millipore) and a DNA fragment was recovered by phenol extraction and ethanol precipitation. The fragments thus obtained were reacted on the Dye Terminator Cycle Sequencing Kit (ABI) according to the manual, followed by nucleotide sequence analysis on the DNA sequencer Prism 377 (ABI), whereby a full-length sequence was obtained. For obtaining a DNA fragment containing this full-length sequence as a single fragment, two primers, mF (5'-GAGAGTCGCGGGCAGAGCAGCGT-CAG-3') (SEQ ID NO:13) and mR (5'-GAAATCATC-CAAGTGAGGGGCGAGAC-3') (SEQ ID NO:14), were respectively synthesized based on the sequence information obtained from the 3' RACE and 5' RACE. The template used was the cDNA synthesized from 80 ng of the previously prepared mouse whole brain poly(A)+ RNA using an RNA PCR kit (Takara) in the following manner. The random primer (9mer) or oligo(dT) 20-M4 adapter primer attached to the kit was used at a final concentration of 2.5 µM, MgCl$_2$ was added to a final concentration of 5 mM, 2 µl of 10×RNA PCR buffer, 8 µl of dNTP mixture (each 2.5 mM), 20 U of RNase inhibitor and 5 U of AMV reverse transcriptase were added, and the total volume was made 20 µl with distilled water. After 10 minutes of treatment of these at 30° C. (only when the random primer was used), the cDNA synthesis was conducted at 42° C. for 30 minutes and the reaction mixtures were respectively dissolved in 5 µl of distilled water and then mixed together, and the mixed solution was used as the template. The PCR reaction mixture was prepared by using EX Taq as the DNA polymerase, adding 2.5 µl of the attached 10×EX Taq buffer, 1 µl of dNTP mixture (each 2.5 mM), 0.5 µl of EX Taq in admixture with an equal volume of TaqStart Antibody (Clontech), 0.5 µl each of primers mF and mR (10 µM each) and 1 µl of the template cDNA solution and making the total volume 25 µl with distilled water.

After 2 minutes of heat treatment at 94° C., the PCR reaction was carried out in 30 cycles each comprising 10 seconds at 98° C. and 30 seconds at 68° C. The PCR product was subjected to 2% agarose gel electrophoresis, and a band of about 750 bp was recovered in the same manner as mentioned hereinabove and subcloned into the plasmid vector pCR2.1 (Invitrogen), followed by further introduction into *E. coli* JM109, to give *E. coli* JM109/pmA10L-13. The cDNA fragment inserted into the transformant obtained was sequenced and, as a result, it was confirmed that this cDNA fragment is a fragment containing the whole coding region of the ligand polypeptide cDNA. The gene sequence is shown in FIG. 15. From the comparison (FIG. 16) with the bovine stomach-derived peptide fragment shown under SEQ ID NO:1, it was considered that this mouse-derived amino acid sequence should be a mouse type counterpart of the bovine type fragment.

EXAMPLE 12

Obtaining of a cDNA Fragment Coding for the Bovine Type Peptide

According to the prescription of RNA PCR Kit (AMV) Ver. 2 (Takara Shuzo), 5 tubes of reaction mixture were respectively prepared using 0.35 µg of a bovine hypothalamus-derived poly(A)+ RNA fraction as the template, with the random 9mer and oligo dT primer. The reverse transcription reaction was carried out at 30° C. for 10 minutes and then at 42° C. for 30 minutes and terminated by heating at 99° C. for 5 minutes. The reaction mixtures were combined and subjected to ethanol precipitation. The cDNA synthesized was recovered from the reaction mixture and dissolved in 40 µl of distilled water. Using 2 µl of this cDNA solution as the template, a reaction mixture (25 µl) was prepared using 0.5 µl each of 10 µM aqueous solutions of synthetic DNA primers having the sequences 5'-GAATCTGAGTTTCTGCGTG-CAGGC-3' (SEQ ID NO:17) and 5'-TTAGAAAG-GCATGGGGCCCTTATG-3' (SEQ ID NO:18), 1 µl of dNTP mixture (each 2.5 mM), 1.25 units of TaKaRa EX Taq (Takara Shuzo) and the reaction buffer attached to the kit. This reaction mixture was heated at 95° C. for 2 minutes, the cycle comprising 10 seconds at 98° C., 20 seconds at 62° C. and 10 seconds at 72° C. was repeated 40 times and, after 30 seconds of incubation at 72° C., the reaction mixture was cooled to 4°

C. The reaction mixture was analyzed by agarose gel electrophoresis, upon which a cDNA band with a size of about 230 bp was detected by ethidium bromide staining. The DNA contained in this portion was recovered from the gel and, with this, the PCR (25 cycles) was again conducted using the same primer set. The amplification product was separated by agarose gel electrophoresis, the DNA was recovered from the gel and, using the respective primers, the sequencing reaction was conducted with the ABI PRISM DyeTerminator Cycle Sequencing Ready Reaction Kit (Perkin Elmer-Applied Biosystems). Upon analysis of the sequence of this cDNA using the ABI PRISM 377 DNA Sequencer, a portion coding for the same sequence as the amino acid sequence determined in Example 9, namely LVQPRGPRSGPGPWQGG, was found out therein.

EXAMPLE 13

Obtaining of a cDNA Coding for the Rat Type Peptide

Total RNA was prepared from whole brain of Wistar rat using Isogen (Nippon Gene) and then poly(A)$^+$ RNA was prepared therefrom using an oligo(dT) cellulose column (mRNA Purification Kit; Pharmacia), following the respective manuals. From 1 μg of the poly(A)$^+$ RNA prepared, cDNA was synthesized according to the manual for Marathon cDNA Amplification Kit (Clontech) and dissolved in 10 μl of distilled water. This was further diluted 50 times with TE buffer and, using the dilution as the template, the PCR was carried out in the same manner as the RACE performed in Example 11 (the example of mouse-derived full-length cloning), except for the primer sets. In the case of 3' RACE, W33-F1 and AP1 were used in the first PCR and W33-F2 and AP1 in the second PCR, and a band of about 800 bp was recovered. In the case of 5' RACE, W33-R1 and AP1 were used in the first PCR and W33-R2 and AP1 in the second PCR, and a band of about 600 bp was recovered. These fragments recovered were sequenced in the same manner as in Example 11 and a full-length sequence of about 1,300 bp was revealed.

For obtaining, as a single fragment, a DNA fragment containing only that region of the sequence revealed which was considered to be translated into amino acids, two primers, rFA10 (5'-GTAGTTGGGAGTCGCGGGCAGAGCAC-3') (SEQ ID NO:19) and rRA10 (5'-TAGAACCATGTCAGGATCAGCACTTT-3') (SEQ ID NO:20), were respectively synthesized based on the sequence information obtained from the 3' RACE and 5' RACE. The template used was the cDNA synthesized from 160 g of the previously prepared rat whole brain poly(A)$^+$ RNA using an RNA PCR kit (Takara) in the following manner. Thus, the random primer (9mer) attached to the kit was used at a final concentration of 2.5 μM, MgCl$_2$ was added to a final concentration of 5 mM, 4 μl of 10×RNA PCR buffer, 16 μl of dNTP mixture (each 2.5 mM), 40 units of RNase inhibitor and 10 units of AMV reverse transcriptase were added, and the total volume was made 40 μl with distilled water. After 10 minutes of these treatment at 30° C., the cDNA synthesis was conducted at 42° C. for 30 minutes and the reaction mixture was dissolved in 40 μl of distilled water. The PCR reaction mixture was prepared by using EX Taq as the DNA polymerase, adding 2.5 μl of the attached 10×EX Taq buffer, 1 μl of dNTP mixture (each 2.5 mM), 0.5 μl of EX Taq in admixture with an equal volume of TaqStart Antibody (Clontech), 0.5 μl each of primers rFA10 and rRA10 (10 μM each) and 1 μl of the template cDNA solution and making the total volume 25 μl with distilled water. After 2 minutes of heat treatment at 94° C., the PCR was carried out in 30 cycles each comprising 10 seconds at 98° C. and 45 seconds at 68° C. The PCR product was subjected to 1.2% agarose gel electrophoresis, and a band was recovered in the same manner as mentioned above. The band DNA was subcloned into the plasmid vector pCR2.1-TOPO (Invitrogen) and further into *E. coli* JM109. The sequence of the insert cDNA fragment was analyzed and a nucleotide sequence of about 1,270 bp, including the primers, was definitely determined.

Furthermore, two primers respectively containing the initiation codon and termination codon, namely the primer rFSal (5'-A<u>GTCGAC</u>GCATAAATCTAGTTCTG-3') (SEQ ID NO:21) and the primer rRNhe (5'-GAGCCCTTCAA<u>GCTAGC</u>TTTAGAAAG-3') (SEQ ID NO:22), were synthesized. The underlined portions are sequences recognized by the restriction enzymes SalI and NheI, respectively. Using these primers, together with about 20 ng of the plasmid (as the template) prepared from the transformant containing the fragment obtained above by amplification using rFA10 and rRA10, and using EX Taq as the DNA polymerase in the same manner as described previously, the PCR was carried out, after 2 minutes of heat treatment at 94° C., by repeating 24 times the cycle comprising 10 seconds at 98° C. and 30 seconds at 68° C. The thus-obtained band of about 260 bp was recovered and the DNA recovered therefrom was subcloned into the plasmid vector pCR2.1-TOPO (Invitrogen) and further introduced into *E. coli* JM109 to give *E. coli* JM109/prSHe-1. The sequence of the cDNA fragment inserted in the transformant obtained was analyzed and it was confirmed that this cDNA fragment contained the whole coding region of the rat type peptide (FIG. 17).

EXAMPLE 14

Obtaining of a cDNA Coding for the Human Type Peptide

For a region well conserved between the mouse and rat type sequences obtained in Examples 11 and 13, primers, AF2 (5'-GTGCCACTGATGCTGCCTCCAGATGG-3') (SEQ ID NO:23) and AR1 (5'-TTAGAAAGGCATGGGTCCCTTATG-3') (SEQ ID NO:24), were synthesized. Separately, cDNA was synthesized from 5 μg of human lung poly(A)$^+$ RNA purchased from Clontech by adding a random primer (9mer, GIBCO BRL) as the primer and using Moloney murine leukemia virus-derived reverse transcriptase (GIBCO BRL) and the buffer attached thereto and carrying out the reaction at 42° C. for 1 hour. The cDNA synthesized was dissolved in 30 μl of TE buffer. Using 1 μl of this cDNA solution as the template, the PCR was carried out. The PCR reaction mixture was prepared using EX Taq as the DNA polymerase as in Example 11, together with the primers AF2 and AR1. After 2 minutes at 94° C., the cycle comprising 10 seconds at 98° C., 20 seconds at 62° C. and 5 seconds at 72° C. was repeated 35 times. The thus-obtained band of about 150 bp was recovered and subjected to analysis for the nucleotide sequence. As a result, it was revealed that this fragment codes for a human type peptide fragment.

Based on this sequence, h3R1 (5'-ACGGCAATGTCCGCCACCTGGTGC-3') (SEQ ID NO:25) and h3R2 (5'-CCCTGGCAGGGAGGTCGGAGGAAA-3') (SEQ ID NO:26) were synthesized for 3' RACE, and h5R1 (5'-GGGCCGCTGGCGGCGGAATTTCCT-3') (SEQ ID NO:27) and h5R2 (5'-GCTGCACCAGGTGGCGGACATTGC-3') (SEQ ID NO:28) for 5' RACE. Separately, cDNAs were synthesized from 1 μg each of human subthalamic nucleus- and lung-derived poly(A)$^+$ RNAs purchased from Clontech according to the manual for the Marathon cDNA Amplification Kit (Clontech). Template cDNA solutions for RACE were prepared by dissolving the cDNAs each in 10 µl of distilled water and further diluting 50 times with TE buffer. Combining the primers h3R1 and AP1 for 3' RACE, and h5R1 and AP1 for 5' RACE, the reaction mixtures were prepared in the same manner as in Example 11 and, after 2 minutes of heat treatment at 94° C., the PCR was carried out by repeating the cycle comprising 10 seconds at 98° C. and 45 seconds at 72° C. five times, then repeating the cycle comprising 10 seconds at 98° C. and 45 seconds at 70° C. five times and further repeating the cycle comprising 10 seconds at 98° C. and 45 seconds at 68° C. 25 times. The reaction mixtures were each diluted 50 times with TE buffer and 2.5 µl of each dilution was used as the template for the second PCR. The primer combinations were changed, namely h3R2 and AP1 or AP2 were used for 3' RACE, and h5R2 and AP1 for 5' RACE. After 2 minutes of heat treatment at 94° C., the reaction was carried out by repeating the cycle comprising 10 seconds at 98° C. and 45 seconds at 72° C. five times, then repeating the cycle comprising 10 seconds at 98° C. and 45 seconds at 70° C. five times and further repeating the cycle comprising 10 seconds at 98° C. and 45 seconds at 68° C. 35 times. As a result, the band of about 500 bp derived from subthalamic nucleus by 5' RACE and the band of about 200 bp derived from lung by 3' RACE were respectively recovered and the nucleotide sequence of about 570 bp was analyzed, and it was found that the cDNA codes for the human type peptide.

Further, for amplifying the expected whole coding region as a single cDNA, primers, hFA10 (5'-TTGGCCTC-CGGGCGCCCGACCTCT-3') (SEQ ID NO:29) and hRA10 (5'-GACATAACCGCAGGGGGTGGGCACTTG-3') (SEQ ID NO:30), were synthesized for both ends of the coding region. The same subthalamic nucleus-derived cDNA as used in RACE was used as the template cDNA. The PCR reaction mixture was prepared by using KlenTaq (Clontech) as the DNA polymerase, adding 2.5 µl of the attached 10× KlenTaq buffer, 1 µl of dNTP mixture (each 2.5 mM), 0.5 µl of Klen-Taq, 0.5 µl each of the primers hFA10 and hRA10 (each 10 µM) and 1 µl of the template cDNA solution, and adding distilled water to a total volume of 25 µl. After 2 minutes of heat treatment at 94° C., the PCR was carried out by repeating the cycle comprising 10 seconds at 98° C. and 30 seconds at 68° C. 30 times. The PCR product was subjected to 2% agarose electrophoresis, the expected band was recovered and subcloned into the plasmid vector pCR2.1-TOPO (Invitrogen) and further introduced into E. coli JM109, whereby E. coli JM109/phSuN-4 was obtained. As a result of sequence analysis of the cDNA fragment inserted in the transformant obtained, it was confirmed that this cDNA fragment contains the whole coding region for the human type peptide. The gene sequence thereof is shown in FIG. 18.

EXAMPLE 15

Obtaining of a cDNA Coding for the Bovine Type Peptide

Several specific primers were prepared for 5' RACE and for 3' RACE, respectively, based on the nucleotide sequence of the PCR product obtained in Example 12. Separately, using 1 µg of bovine lung-derived poly(A)+ RNA, cDNA was synthesized according to the manual for the Marathon cDNA Amplification Kit (Clontech) and the cDNA solution obtained after adapter addition in the final step was diluted 50 times with distilled water. Reaction mixtures (each 25 µl) were prepared using 2.5 µl of that 50-fold dilution, 0.5 µl of each specific primer (10 µM) shown below under SEQ ID NO:31 to 34 etc., 0.5 µl of AP1 primer (attached to the enzyme, 10 µM), 0.5 µl of EX Taq DNA polymerase (Takara Shuzo) in admixture with an equal volume of TaqStart Antibody (Clontech), 2.5 µl of ×10 EX Taq buffer and 1 µl of dNTPs (each attached to the enzyme) and, after 2 minutes of heat treatment at 95° C., the cycle comprising 10 seconds at 98° C. and 1 minute at 72° C. was repeated 5 times, then the cycle comprising 10 seconds at 98° C. and 1 minute at 70° C. was repeated 5 times and further the cycle comprising 10 seconds at 98° C. and 1 minute at 68° C. was repeated 25 times, further followed by 1 minute of heating at 68° C. Using 1 µl of this reaction mixture, reaction mixtures were prepared changing the primer combination, and the second PCR was carried out under the same conditions (except that the number of repetitions of the last amplification cycle was increased from 25 times to 35 times).

Among the PCR products obtained using various primer combinations, those main PCR products that were obtained by performing the first PCR using the combination of FF1 (5'-CCTGCTGCTCTGGCTCTGCCTGAG-3') (SEQ ID NO:31) with AP1 (5'-CCATCCTAATACGACTCACTAT-AGGGC-3') (SEQ ID NO:32) and performing the second PCR using 1 µl of the first reaction mixture with the primer combination of FF2 (5'-GCGGTGTGCGGAGGACCCCT-GCTG-3') (SEQ ID NO:33) with AP2 (5'-ACTCACTAT-AGGGCTCGAGCGGC-3') (SEQ ID NO:34) and separated by agarose gel electrophoresis were recovered from the gel and their sequences were determined. By comparing with the mouse cDNA obtained in Example 11, it was found that the 3' RACE product analyzed was a cDNA fragment having a sequence further downstream from the translation termination codon. Based on the sequence of the bovine type peptide cDNA revealed by this 3' RACE, a primer corresponding to the 3' untranslated region part was synthesized. Separately, a primer was synthesized based on the sequence of the 5' untranslated region of cDNA already revealed in other animal species. A reaction mixture (25 µl) was prepared using cDNA corresponding to 150 ng of bovine hypothalamus poly(A)+ RNA as the template and adding 0.5 µl of each primer (10 µM), 0.5 µl of EX Taq DNA polymerase (Takara Shuzo) in admixture with an equal volume of TaqStart Antibody (Clontech), 2.5 µl of ×10 EX Taq buffer and 1 µl of dNTPs (each attached to the enzyme) and, after 2 minutes of heat treatment at 95° C., the cycle comprising 10 seconds at 98° C., 20 seconds at 62° C. and 30 seconds at 72° C. was repeated 40 times, followed further by 30 seconds of incubation at 72° C. The reaction products were separated by agarose gel electrophoresis. The main PCR products were recovered from the gel and analyzed for their nucleotide sequences. Nucleotide sequence analysis of the main PCR products obtained by using the primer combination of NCR4 (5'-GGCCGCG-GCGGCCCAAGGAGCAGC-3') (SEQ ID NO:35) with RV1 (5'-GCGTGTGGTGGCCCCTTCGGTCCT-3') (SEQ ID NO:36) or RV2 (5'-AATCACAGGGGGTGGGCGT-GTGGT-3') (SEQ ID NO:37) revealed that a cDNA having the full-length translated region had been amplified. Therefore, the cDNA was subcloned into the plasmid vector pCR2.1 using the Original TA Cloning Kit (Invitrogen), followed by further introduction into E. coli JM109, whereby E. coli JM109/pBovA10prec24 was obtained. As a result of sequence analysis of the cDNA fragment inserted in the transformant obtained, it was confirmed that this cDNA fragment contains the whole coding region for the bovine type peptide (FIG. 19).

The amino acid sequences of the mouse, rat, human and bovine type peptides as revealed in Examples 11, 13, 14 and 15 are comparatively shown in FIG. 20.

EXAMPLE 16

Production of a Peptide Acting on the APJ Receptor, Namely (SEQ ID NO: 44) pGlu-Arg-Pro-Arg-Leu-Ser-His-Lys-Gly-Pro-Met-Pro-Phe The reaction vessel of the peptide synthesizer ABI 430A was charged with an amount, corresponding to 0.5 millimole, of a commercial Boc-Phe-OCH$_2$-PAM resin (0.72 mmole/g resin) and, according to the per se known Boc-strategy (NMP-HOBt) peptide synthesis technique, Boc-Pro, Boc-Met, Boc-Pro, Boc-Gly, Boc-Lys(Cl-Z), Boc-His(Bom), Boc-Ser(Bzl), Boc-Leu, Boc-Arg(Tos), Boc-Pro, Boc-Arg(Tos), Boc-Gln were introduced in that order, whereby the desired protected peptide-resin was obtained. A 0.22-g portion of this resin was stirred, together with 0.43 g of p-cresol, in 5 ml of anhydrous hydrogen fluoride at 0° C. for 60 minutes, the hydrogen fluoride was then distilled off under reduced pressure, acetic acid-water was added to the residue and the peptide was extracted with acetic acid-water. The extract was concentrated to a sufficient extent, distilled water and diethyl ether were added and extraction and phase separation were conducted. The aqueous layer collected was lyophilized, the lyophilizate was dissolved in a small amount of 50% acetic acid-water and applied to a Sephadex (registered trademark) G-25 column (2.0×80 cm) packed with the same solvent. After development with the same solvent, main fractions were combined and lyophilized to give about 50 mg of a white powder. This was dissolved in 50 ml of 50% acetic acid-water and maintained on a water bath at 60° C. for 1 hour. After it was confirmed by HPLC that the main peak at 13.9 minutes had disappeared and wholly converted to a peak at about 15.6 minutes, the mixture was returned to room temperature and applied to a reversed phase chromatography column (2.6×60 cm) packed with LiChroprep (registered trademark) RP-18. The column was washed with 200 ml of 0.1% TFA-water and then linear gradient elution was performed using 300 ml of 0.1% TFA-water and 300 ml of 0.1% TFA-containing 33% acetonitrile-water. Fractions of acetonitrile concentrations of about 20% were combined and lyophilized to give 28 mg of a white powder.

Mass analysis (M+H)$^+$: 1533.953 (calculated value 1533.811) HPLC elution time: 15.7 min.

Column Conditions:

Column: Wakosil 5C18T, 4.6×100 mm

Eluent: solvent A -0.1% TFA-water, solvent B -0.1% TFA-containing acetonitrile; linear concentration gradient elution from A/B=95/5 to A/B=45/55 (25 minutes)

Flow rate: 1.0 ml/min.

EXAMPLE 17

Measurement of the Ligand Activity of the Peptide (SEQ ID NO: 44) pGlu-Arg-Pro-Arg-Leu-Ser-His-Lys-Gly-Pro-Met-Pro-Phe for the APJ Receptor The peptide obtained in Example 16 and the peptide represented by the amino acid sequence covering the 42nd to 77th residues of the sequence defined under SEQ ID NO:40 were dissolved in sterile distilled water to a concentration of 1×10$^{-3}$ M and each solution was diluted to the peptide concentrations of 10$^{-8}$, 10$^{-9}$, 10$^{-10}$ and 10$^{-11}$ M using the Cytosensor medium containing 0.1% BSA. CHO cells with the APJ receptor cDNA introduced therein in the same manner as in Example 6 were set in the work station of the Cytosensor and, after stabilization of the acidification rate of each cell, one of the peptide dilutions was introduced into one of the channels of the Cytosensor and, by changing the channel, the cells were exposed to the dilution for 7 minutes and 2 seconds. The change in acidification rate when the cell reaction arrived at a maximum in the third cycle of sample introduction was calculated with the basal level value being taken as 100%. The results thus obtained are shown in FIG. 21.

EXAMPLE 18

Production of (a Portion of SEQ ID NO: 42) Val-Gln-Pro-Arg-Gly-Pro-Arg-Ser-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe A commercial Boc-Phe-OCH$_2$-PAM resin (0.72 mmole/g resin; 0.5 mmole) was charged into the reaction vessel of the peptide synthesizer ABI 430A, and peptide synthesis was carried out by introducing Boc-Pro, Boc-Met, Boc-Gly, Boc-Lys(Cl-Z), Boc-His(Bom), Boc-Ser(Bzl), Boc-Leu, Boc-Arg (Tos), Boc-Gln, Boc-Phe, Boc-Trp(CHO) and Boc-Val in the order of the above amino acid sequence by the Boc-strategy (NMP-HOBt) method to give the desired protected peptide resin. This resin (0.17 g) was stirred with 1.0 g of p-cresol and 1.0 ml of 1,4-butanedithiol in 8 ml of anhydrous hydrogen fluoride at 0° C. for 60 minutes, the hydrogen fluoride was distilled off, acetic acid-water was added to the residue, and the peptide was extracted with acetic acid-water. The extract was concentrated to a sufficient extent, distilled water and diethyl ether were added for extraction and phase separation, the aqueous layer was collected and lyophilized, the lyophilizate was dissolved in a small amount of 50% aqueous acetic acid, the solution was applied to a Sephadex™ G-25 column (2.0×80 cm) prepared by packing with the same solvent, development was effected with the same solvent, main fractions were collected and lyophilized to give about 70 mg of a white powder. This was applied to a reversed phase chromatography column (2.6×60 cm) packed with LiChroprep™ RP-18, the column was washed with 200 ml of 0.1% TFA-water, and linear gradient elution was carried out using 300 ml of 10% acetonitrile-water containing 0.1% TFA and 300 ml of 30% acetonitrile-water containing 0.1% TFA. The main fractions were combined and lyophilized to give 33 mg of a white powder.

Mass analysis (M+H)$^+$: 4064.6 (calculated value 4064.2)

HPLC elution time: 16.0 minutes

Column Conditions:

Column: Wakosil 5C18T, 4.6×100 mm

Eluent: solution A -0.1% TFA-water;

solution B -0.1% TFA-containing acetonitrile.

Linear concentration gradient from A/B=95/5 to A/B=45/55 (25 minutes)

Flow rate: 1.0 ml/minute.

EXAMPLE 19

Production of (a Portion of SEQ ID NO: 42) Leu-Val-Gln-Pro-Arg-Gly-Pro-Arg-Ser-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe Boc-Leu was further introduced into the resin obtained in Example 18 and, subsequently, the hydrogen fluoride treatment and chromatographic purification were carried out in the same manner as in Example 18. The main fractions were combined and lyophilized to give 23 mg of a white powder.

Mass analysis (M+H)⁺: 4177.7 (calculated value 4177.3)
HPLC elution time: 16.2 minutes
Column Conditions:
Column: Wakosil 5C18T, 4.6×100 mm
Eluent: solution A -0.1% TFA-water;
solution B -0.1% TFA-containing acetonitrile.
Linear concentration gradient from A/B=95/5 to A/B=45/55 (25 minutes)
Flow rate: 1.0 ml/minute.

EXAMPLE 20

Production of (a Portion of SEQ ID NO: 40) Leu-Val-Gln-Pro-Arg-Gly-Ser-Arg-Asn-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe The reaction vessel of a peptide synthesizer (ABI 433A) was charged with 0.25 mmol of a Fmoc-Phe-O-Clt resin (0.32 mmol/g) prepared by introducing Fmoc-Phe-OH into a commercial 2-chlorotrityl resin (Clt resin, 1.3 mmol/g), and solid phase synthesis was carried out by the Fmoc/DCC/HOBt method. The protective group employed for the side chain of the Fmoc amino acid was Pbf in the case of Arg, tBu in the case of Ser, Boc in the case of Trp and Lys, and Trt in the case of His, Asn and Gln. Other amino acids were used without side chain protection. Peptide chain introduction from Phe in the direction of the N-terminal Leu in the order indicated by the sequence shown above gave the desired protected peptide resin.

A 50-mg (4.45-mmol) portion of this resin was stirred in 1 ml of a mixed solution composed of TFA, thioanisole, m-cresol, H₂O and ethanedithiol (82.5:5:5:5:2.5) at room temperature for 2 hours, ether was added to the reaction mixture, and the resulting precipitate white powder was recovered by centrifugation. The procedure for removing the supernatant was repeated three times. The residue was extracted with water. Lyophilization gave 23.1 mg of a white powder. The thus-obtained crude peptide was subjected to preparative HPLC using a TSK GEL ODS 120T column (20×300 mm). Using solution A: 0.1% TFA-water and solution B: 0.1% TFA-containing acetonitrile, linear concentration gradient elution (60 minutes) was performed from A/B=85/15 to 75/25. Fractions containing the desired product were combined and lyophilized to give 10.2 mg of a white powder.

Mass analysis (M+H)⁺: 4194.8 (calculated value 4194.3)
HPLC elution time: 16.5 minutes
Elution Conditions:
Column: YMC A-301-3 (4.6×100 mm)
Eluent: solution A -0.1% TFA-water;
solution B -0.1% TFA-containing acetonitrile.
Linear concentration gradient from A/B=100/0 to A/B=50/50 (25 minutes)
Flow rate: 1.0 ml/minute.

EXAMPLE 21

Production of (a Portion of SEQ ID NO: 40) His-Leu-Val-Gln-Pro-Arg-Gly-Ser-Arg-Asn-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe The resin obtained in Example 20 was further subjected to condensation with Fmoc-His(Trt), followed by the same purification treatment as in Example 20, to give 10 mg of a white powder.

Mass analysis (M+H)⁺: 4331.2 (calculated value 4331.4)
HPLC elution time: 16.3 minutes
Elution Conditions:
Column: YMC A-301-3 (4.6×100 mm)
Eluent: solution A -0.1% TFA-water;
solution B -0.1% TFA-containing acetonitrile.
Linear concentration gradient from A/B=100/0 to A/B=50/50 (25 minutes)
Flow rate: 1.0 ml/minute.

EXAMPLE 22

Production of (a Portion of SEQ ID NO: 15) Leu-Val-Lys-Pro-Arg-Thr-Ser-Arg-Thr-Gly-Pro-Gly-Ala-Trp-Gln-Gly-Gly-Arg-Arg-Lys-Phe-Arg-Arg-Gln-Arg-Pro-Arg-Leu-Ser-His-Lys-Gly-Pro-Met-Pro-Phe Into a commercial Boc-Phe-OCH₂-PAM resin (0.72 mmole/g resin) were introduced Boc-Pro, Boc-Met, Boc-Gly, Boc-Lys(Cl-Z), Boc-His(Bom), Boc-Ser(Bzl), Boc-Leu, Boc-Arg(Tos), Boc-Gln, Boc-Phe, Boc-Trp(CHO), Boc-Ala, Boc-Thr(Bzl) and Boc-Val in the order based on the above amino acid sequence in the same manner as in Example 18, to give the desired protected peptide resin. This resin was treated with hydrogen fluoride in the same manner as in Example 18 and the peptide recovered was purified in the same manner to give 25 mg of a white powder.

Mass analysis (M+H)⁺: 4199.0 (calculated value 4199.3)

EXAMPLE 23

Production of (a Portion of SEQ ID NO: 15) Tyr-Leu-Val-Lys-Pro-Arg-Thr-Ser-Arg-Thr-Gly-Pro-Gly-Ala-Trp-Gln-Gly-Gly-Arg-Arg-Lys-Phe-Arg-Arg-Gln-Arg-Pro-Arg-Leu-Ser-His-Lys-Gly-Pro-Met-Pro-Phe Boc-Tyr(Br-Z) was further condensed with the resin obtained in Example 22. The resulting resin was subjected to the same treatment and purification procedure to give 12 mg of a white powder.

Mass analysis (M+H)⁺: 4362.7 (calculated value 4362.4)

EXAMPLE 24

Production of (a Portion of SEQ ID NO: 40) Pro-Arg-Leu-Ser-His-Lys-Gly-Pro-Met-Pro-Phe A commercial Boc-Phe-OCH₂-PAM resin (0.72 mmole/g resin) was condensed with Boc-Pro, Boc-Met, Boc-Pro, Boc-Gly, Boc-Lys(Cl-Z), Boc-His(Bom), Boc-Ser(Bzl), Boc-Leu, Boc-Arg(Tos) and Boc-Pro in that order. The resin was treated with hydrogen fluoride in the presence of p-cresol and the peptide purified in the same manner as in Example 18 to give 54 mg of a white powder.

Mass analysis (M+H)⁺: 1266.4 (calculated value 1266.7)

EXAMPLE 25

Production of (a Portion of SEQ ID NO: 15) Arg-Pro-Arg-Leu-Ser-His-Lys-Gly-Pro-Met-Pro-Phe The resin of (a portion of SEQ ID NO: 15) Example 24 was further condensed with Boc-Arg(Tos), followed by the same treatment and purification procedure, to give 30 mg of a white powder.

Mass analysis (M+H)⁺: 1422.6 (calculated value 1422.8)

EXAMPLE 26

Production of (a Portion of SEQ ID NO: 15) Gln-Arg-Pro-Arg-Leu-Ser-His-Lys-Gly-Pro-Met-Pro-Phe The resin of Example 25 was further condensed with Boc-Gln, followed by the same treatment and purification procedure and lyophilization from diluted aqueous hydrochloric acid, to give 21 mg of a white powder.

Mass analysis (M+H)$^+$: 1551.1 (calculated value 1550.8)

EXAMPLE 27

Production of (a Portion of SEQ ID NO: 40) Arg-Arg-Gln-Arg-Pro-Arg-Leu-Ser-His-Lys-Gly-Pro-Met-Pro-Phe The resin of Example 26 was further condensed with Boc-Arg(Tos) two times, followed by the same treatment and purification procedure, to give 17 mg of a white powder.

Mass analysis (M+H)$^+$: 1862.8 (calculated value 1863.0)

EXAMPLE 28

Production of (SEQ ID NO: 45) Cys-Phe-Arg-Arg-Gln-Arg-Pro-Arg-Leu-Ser-His-Lys-Gly-Pro-Met-Pro-Phe The resin of Example 27 was further condensed with Boc-Phe and then with Boc-Cys(MeBzl), followed by the same treatment and purification procedure, to give 30 mg of a white powder.

Mass analysis (M+H)$^+$: 2113.2 (calculated value 2113.1)
HPLC elution time: 16.0 minutes
Elution Conditions:
Column: YMC A-301-3 (4.6×100 mm)
Eluent: solution A -0.1% TFA-water;
solution B -0.1% TFA-containing acetonitrile.
Linear concentration gradient from A/B=100/0 to A/B=50/50 (25 minutes)
Flow rate: 1.0 ml/minute.

EXAMPLE 29

Production of (a Portion of SEQ ID NO: 15) Arg-Arg-Lys-Phe-Arg-Arg-Gln-Arg-Pro-Arg-Leu-Ser-His-Lys-Gly-Pro-Met-Pro-Phe The resin of Example 27 was further condensed with Boc-Phe, Boc-Lys(Cl-Z), Boc-Arg(Tos) and Boc-Arg(Tos) in that order, followed by the same treatment and purification procedure, to give 13 mg of a white powder.

Mass analysis (M+H)$^+$: 2450.4 (calculated value 2450.4)
HPLC elution time: 15.7 minutes
Elution Conditions:
Column: YMC A-301-3 (4.6×100 mm)
Eluent: solution A -0.1% TFA-water;
solution B -0.1% TFA-containing acetonitrile.
Linear concentration gradient from A/B=100/0 to A/B=50/50 (25 minutes)
Flow rate: 1.0 ml/minute.

EXAMPLE 30

Production of (SEQ ID NO: 46) pGlu-Arg-Pro-Arg-Leu-Ser-His-Lys-Gly-Pro-Met-Pro

A commercial Boc-Pro-OCH$_2$-PAM resin (0.63 mmole/g resin) was condensed with Boc-Met, Boc-Pro, Boc-Gly, Boc-Lys(Cl-Z), Boc-His(Bom), Boc-Ser(Bzl), Boc-Leu, Boc-Arg(Tos), Boc-Pro, Boc-Arg(Tos) and Z-Glu in that order. The resulting resin was treated with hydrogen fluoride in the presence of p-cresol and the peptide purified in the same manner as in Example 18 to give 56 mg of a white powder.

Mass analysis (M+H)$^+$: 1386.4 (calculated value 1386.7)
HPLC elution time: 12.7 minutes
Column Conditions:
Column: Wakosil 5C18T, 4.6×100 mm
Eluent: solution A -0.1% TFA-water;
solution B -0.1% TFA-containing acetonitrile.
Linear concentration gradient from A/B=95/5 to A/B=45/55 (25 minutes)
Flow rate: 1.0 ml/minute.

EXAMPLE 31

Production of (SEQ ID NO: 47) pGlu-Arg-Pro-Arg-Leu-Ser-His-Lys-Gly-Pro-Met

A commercial Boc-Met-OCH$_2$-PAM resin (0.66 mmole/g resin) was condensed with Boc-Pro, Boc-Gly, Boc-Lys(Cl-Z), Boc-His(Bom), Boc-Ser(Bzl), Boc-Leu, Boc-Arg(Tos), Boc-Pro, Boc-Arg(Tos) and Z-Glu in that order. The resulting resin was treated with hydrogen fluoride in the presence of p-cresol and the peptide purified in the same manner as in Example 18 to give 29 mg of a white powder.

Mass analysis (M+H)$^+$: 1289.9 (calculated value 1289.7)
HPLC elution time: 11.8 minutes
Column Conditions:
Column: Wakosil 5C18T, 4.6×100 mm
Eluent: solution A -0.1% TFA-water;
solution B -0.1% TFA-containing acetonitrile.
Linear concentration gradient from A/B=95/5 to A/B=45/55 (25 minutes)
Flow rate: 1.0 ml/minute.

EXAMPLE 32

Production of (SEQ ID NO: 48) Met-Leu-Val-Gln-Pro-Arg-Gly-Ser-Arg-Asn-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe The resin of Example 20 was further condensed with Fmoc-Met, followed by the same purification procedure, to give 5 mg of a white powder.

Mass analysis (M+H)$^+$: 4324.9 (calculated value 4325.3)
HPLC elution time: 16.8 minutes
Elution Conditions:
Column: YMC A-301-3 (4.6×100 mm)
Eluent: solution A -0.1% TFA-water;
solution B -0.1% TFA-containing acetonitrile.
Linear concentration gradient from A/B=100/0 to A/B=50/50 (25 minutes)
Flow rate: 1.0 ml/minute.

EXAMPLE 33

Assaying of Inhibitory Activity Against Forskolin-Stimulated cAMP Production

CHO-A10 clone 6 cells were sowed onto 24-well tissue culture plates ($3 \times 10^5$ cells/well) and cultured overnight. Hanks' balanced salt solution (HBSS) containing 0.2 mM 3-isobutyl-1-methylxanthine (IBMX) and 0.05% bovine serum albumin was prepared as an assay buffer. Each well was washed with two 500-µl portions of the assay buffer and then preincubation was performed at 37° C. for 30 minutes. After further washing with 500 µl of the assay buffer, 500 µl of a solution of the sample in the assay buffer supplemented with 1 µM forskolin was added to each well, and incubation was performed at 37° C. for 30 minutes. To know the basal level of cAMP production by the cells, wells were also prepared by incubation with the assay buffer without addition of forskolin and, to know the maximum level of cAMP production resulting from stimulation by forskolin, wells were further prepared by incubation with the assay buffer supplemented with forskolin. After completion of the incubation, each well was washed with 500 µl of the assay buffer, and 500 µl of lysis buffer 1B attached to the Amersham cAMP EIA kit was added to each well to thereby effect extraction of cAMP. According to the kit prescription, a 100-µl portion of each extract was subjected to cAMP assay. The inhibitory activity against CAMP production was calculated as the percentage, relative to the increase in forskolin-stimulated CAMP production (difference between the maximum level and the basal level), of the difference in cAMP production between the maximum level and the level in the well with the sample added (percent of inhibition of CAMP production). The results thus obtained are shown in FIG. 22.

EXAMPLE 34

Preparation of Structural Gene of the Polypeptide Having the Amino Acid Sequence of (a Portion of SEQ ID NO: 40) Leu-Val-Gln-Pro-Arg-Gly-Ser-Arg-Asn-Gly-Pro-Gly-Pro-Trp-Gln-Gly-Gly-Arg-Arg-Lys-Phe-Arg-Arg-Gln-Arg-Pro-Arg-Leu-Ser-His-Lys-Gly-Pro-Met-Pro-Phe (Human Apelin-36)

The structural gene for human apelin-36 was prepared using six DNA fragments shown in FIG. 23 (#1 and #5, products of Greiner Japan; #2 and #6, products of Kikotech; #3 and #4, products of Amersham Pharmacia Biotech).

a) Phosphorylation of DNA Oligomers

Four oligomers (1 µg each), except for #1 and #6 which were to form the 5' end, were each phosphorylated at the 5' end by carrying out the reaction in 100 µL of a phosphorylation reaction medium [50 mM Tris-HCl (pH 7.6), 10 mM MgCl$_2$, 1 mM spermidine, 10 mM dithiothreitol, 0.1 mg/mL bovine serum albumin, 1 mM ATP, 10 units of T4 polynucleotide kinase (Nippon Gene)] at 37° C. for 1 hour. After phenol treatment, the aqueous layer was recovered, 2 volumes of ethanol was added, the mixture was cooled to −70° C., and the DNA was precipitated by centrifugation.

b) Ligation of DNA Fragments

The phosphorylated DNA fragments obtained in the above manner and 1 µg each of #1 and #2 were combined to a total volume of 120 µL. This mixture was maintained at 80° C. for 10 minutes and then gradually cooled to room temperature to effect annealing. For the ligation reaction, TaKaRa DNA Ligation Kit ver. 2 (Takara Shuzo) was used. Thus, 30 µL of solution II was added to 30 µL of the annealing mixture and, after thorough mixing, 60 µL of solution I was added, and the ligation reaction was carried out at 37° C. for 1 hour. After phenol treatment, the aqueous layer was recovered, 2 volumes of ethanol was added, the mixture was cooled to −70° C., and the DNA was precipitated by centrifugation.

c) Phosphorylation at 5' End

The precipitate was dissolved in 10 µL of TE buffer (10 mM Tris-HCl (pH 8.0), 1 mM EDTA) and subjected to 5' end phosphorylation in 100 µL of a phosphorylation reaction medium [50 mM Tris-HCl (pH 7.6), 10 mM MgCl$_2$, 1 mM spermidine, 10 mM dithiothreitol, 0.1 mg/mL bovine serum albumin, 1 mM ATP, 10 units of T4 polynucleotide kinase (Nippon Gene)] at 37° C. for 1 hour. After phenol treatment, the aqueous layer was recovered, 2 volumes of ethanol was added, the mixture was cooled to −70° C., and the DNA was precipitated by centrifugation and dissolved in 20 µL of TE buffer.

EXAMPLE 35

Preparation of Human Apelin-36 Expression Plasmid pTB960-2 (EP-A-499990; Koyama et al., Journal of Biotechnology, vol. 32, p. 273) was digested with XbaI and AvaI, and the digestion mixture was subjected to 1% agarose electrophoresis. A DNA fragment of about 4.4 kp was extracted using QIAquick Gel Extraction Kit (Qiagen) and dissolved in 25 µL of TE buffer. This XbaI-AvaI fragment of pTB960-2 and human apelin-36 structural gene prepared as mentioned above were subjected to ligation reaction using TaKaRa DNA Ligation Kit ver. 2 (Takara Shuzo). Thus, 1 µL of the solution of the XbaI-AvaI fragment of pTB960-2 and 4 µL of the solution of human apelin-36 structural gene were mixed together, 5 µL of solution I was added and the ligation reaction was conducted at 16° C. for 30 minutes. Competent cells of *Escherichia coli* JM109 (Toyobo) were transformed using 10 µL of the ligation mixture, then sowed onto LB agar medium containing 10 µg/mL of tetracycline and cultured at 37° C. for 1 day. A tetracycline-resistant colony thus formed was selected. This transformant was cultured overnight in LB medium and a plasmid, pTB960-13, was prepared using QIAprep8 Miniprep Kit (Qiagen). The nucleotide sequence of human apelin-36 structural gene portion of said plasmid was confirmed using an Applied Biosystems model 377 DNA sequencer. The plasmid pTB960-13 was used to transform the *E. coli* BL21(DE3) strain (Novagen), the transformed cells were sowed onto LB agar medium containing 10 µg/mL of tetracycline and cultured at 37° C. for 1 day, whereby human apelin-36-CS23 fusion protein expression strain, BL21 (DE3)/pTB960-13, was obtained.

EXAMPLE 36

The transformant cells obtained in Example 35 were shake-cultured in a 2-liter flask at 37° C. for 8 hours using 1 L of LB medium (1% peptone, 0.5% yeast extract, 0.5% sodium chloride) containing 5.0 mg/L of tetracycline. The culture obtained was transferred to a 50-L fermenter charged with 19 L of a main fermentation medium (1.68% disodium monohydrogen phosphate, 0.3% potassium dihydrogen phosphate, 0.1% ammonium chloride, 0.05% sodium chloride, 0.05% magnesium sulfate, 0.02% antifoam, 0.00025% ferrous sulfate, 0.00025% thiamine hydrochloride, 1.5% glucose, 1.5% casamino acids), and cultivation under aeration and agitation was started at 30° C. When the turbidity of the culture arrived at about 500 Klett units, isopropyl-β-D-thiogalactopyranoside was added to a final concentration of 12 mg/L, and cultivation was carried out for further 4 hours. After completion of the cultivation, the culture fluid was centrifuged to give about 66 g of wet bacterial cells, which were frozen stored at −80° C.

EXAMPLE 37

Obtaining of Human Apelin-36

To 550 g of the bacterial cells obtained in Example 35 was added 1,500 ml of a solution comprising 10 mM EDTA plus 1 mM (p-amidinophenyl)methanesulfonyl fluoride hydrochloride (pH 6.0), and the mixture was sonicated (Branson Sonifier model 450) and centrifuged (10,000 rpm, 60 minutes). The supernatant was pooled, while the sediment was treated again in the same manner. The supernatants pooled were adjusted to pH 6.0 and applied to an AF-Heparin Toyopearl 650 M column (30 mm ID×500 mm L, Tosoh) equilibrated with 50 mM phosphate buffer (pH 6.0), for adsorption. The column was washed and then stepwise gradient elution was carried out with 0 to 100% B (B=50 mM phosphate buffer+2 M NaCl, pH 6.0) to give 530 ml of human apelin-36-CS23 fusion protein fraction. This eluate was concentrated using Pericon Minicassette (Millipore) while adding 0.1 M acetic acid. Thus was obtained a 0.1 M acetic acid solution of human apelin-36-CS23 fusion protein. Urea was added to this solution to a final concentration of 6 M, then 35 mg of 1-cyano-4-dimethylaminopyridinium salt (DMAP-CN) was added, and the reaction was allowed to proceed at room temperature for 15 minutes. After completion of the reaction, the reaction mixture was applied to a Sephadex G-25 column (46 mm ID, 600 mm L, Pharmacia) equilibrated with 10% acetic acid and development was effected using the same 10% acetic acid as used for equilibration at a flow rate of 6 ml/minute to give a fraction containing the S-cyanized human apelin-36-CS23 fusion protein. This eluate was concentrated and desalted using Pericon Minicassette (Millipore) to give a desalted solution of the human apelin-36-CS23 fusion protein. Urea was added to this desalted solution to a final concentration of 6 M, 1 N sodium hydroxide was further added to a final concentration of 0.06 N, and the reaction was allowed to proceed at 0° C. for 15 minutes. Thereafter, the reaction mixture was adjusted to pH 6.0 with acetic acid to give human apelin-36. This reaction mixture was applied to an SP-5PW column (21.5 mm ID×150 mm L, Tosoh) equilibrated with 50 mM phosphate buffer (pH 6.5) containing 3 M urea, for adsorption. After washing the column, stepwise gradient elution was carried out with 0 to 40% B (B=50 mM phosphate buffer+1 M NaCl+3 M urea, pH 6.5) to give human apelin-36 fraction. This human apelin-36 fraction was further applied to a C4P-50 column (21.5 mm ID×300 mm L, Showa Denko) equilibrated with 0.1% trifluoroacetic acid, for adsorption. After washing the column, stepwise gradient elution was carried out with 15 to 30% B (B=80% acetonitrile/ 0.1% trifluoroacetic acid). The human apelin-36 fractions obtained were pooled and lyophilized to give a lyophilizate powder of human apelin-36.

a) Amino Acid Composition Analysis

The amino acid composition was determined using an amino acid analyzer (Hitachi model L-8500A amino acid analyzer). As a result, the amino acid composition was in agreement with that deduced from the nucleotide sequence of the DNA for human apelin-36 with methionine added to the N terminus (Table 1).

TABLE 1

Amino acid composition analysis

| Amino acid for human apelin-36 | Number of residues per mole | Value predicted by nucleotide sequence |
|---|---|---|
| Asx | 1.0 | 1 |
| Thr[1] | | 0 |
| Ser[1] | 1.9 | 2 |
| Glx | 3.0 | 3 |
| Pro | 5.7 | 6 |
| Gly | 5.7 | 6 |
| Ala | 0 | 0 |
| Cys[2] | | 0 |
| Val | 1.0 | 1 |
| Met | 2.0 | 1 |
| Ile | 0 | 0 |
| Leu | 2.0 | 2 |
| Tyr | 0 | 0 |
| Phe | 1.9 | 2 |
| His | 1.0 | 1 |
| Lys | 1.8 | 2 |
| Arg | 7.3 | 8 |
| Trp | 0.9 | 1 |

Acid hydrolysis (6N hydrochloric acid-4% thioglycolic acid, 110° C., 24 or 48 hours of hydrolysis)
[1]Value obtained by extrapolation to hour 0.
[2]No detection made.

b) N-Terminal Amino Acid Sequence Analysis

The N-terminal amino acid sequence was determined using a gaseous phase protein sequencer (Applied Biosystems model 477A). As a result, the N-terminal amino acid sequence was in agreement with the sequence deduced from the nucleotide sequence of the DNA for human apelin-36 except for methionine added to the N terminus (Table 2).

TABLE 2

N-terminal amino acid sequence

| Residue No. | PTH[1]-amino acid detected (pmol) | Amino acid deduced from nucleotide sequence for human apelin-36 |
|---|---|---|
| 1 | Met (526) | |
| 2 | Leu (648) | Leu |
| 3 | Val (513) | Val |
| 4 | Gln (437) | Gln |
| 5 | Pro (463) | Pro |
| 6 | Arg (216) | Arg |
| 7 | Gly (232) | Gly |
| 8 | Ser (129) | Ser |
| 9 | Arg (129) | Arg |
| 10 | Asn (142) | Asn |
| 11 | Gly (185) | Gly |
| 12 | Pro (219) | Pro |
| 13 | Gly (202) | Gly |
| 14 | Pro (188) | Pro |
| 15 | Trp (88) | Trp |
| 16 | Gln (116) | Gln |
| 17 | Gly (120) | Gly |
| 18 | Gly (72) | Gly |
| 19 | Arg (56) | Arg |
| 20 | Arg (40) | Arg |

Analysis was made using 1 nmol.
[1]Phenylthiohydantoin.

c) C-Terminal Amino Acid Analysis

The C-terminal amino acid was analyzed using an amino acid analyzer (Hitachi molel L-8500A amino acid analyzer).

TABLE 3

C-terminal amino acid analysis

| human apelin-36 | C-terminal amino acid | Recovery (%) |
|---|---|---|
|  | Phe | 38.6 |

Gaseous phase hydrazine decomposition (100° C., 6 hours).

From the above results, it was revealed that the human apelin-36 obtained in Example 37 was a molecular species with methionine added to the N terminus (Met-human apelin-36).

EXAMPLE 38

Biological Activity Assay

The activity assay of the human apelin-36 obtained in Example 37 was performed by the method described in Example 33 and it was confirmed that its activity was equivalent to that of the synthetic product.

EXAMPLE 39

Elimination of N-Terminal Methionine

A 4-mg portion of the Met-human apelin-36 obtained in Example 37 was dissolved in 0.8 ml of a 3 M urea solution. Then, a mixture composed of 0.05 ml of 80 mM copper sulfate, 0.046 g of glyoxylic acid and 0.1 ml of pyridine was added, and the reaction was allowed to proceed at 25° C. for 1 hour. Thereafter, the reaction mixture was applied to a Sephadex G-25 column (10 mm ID×250 mm L) equilibrated with 2.5 M urea plus 10 mM phosphate buffer (pH 5.5), and development was carried out with the same solution as used for equilibration at a flow rate of 0.5 ml/minute The fractions containing the diketone form of Met-human apelin-36 were pooled. To the pooled fractions were then added 4 M acetic acid, 4 M sodium acetate and 3 M urea, followed by further addition of o-phenylenediamine to a concentration of 40 mM. The mixture was deaerated and sealed with nitrogen gas, and the reaction was allowed to proceed at 25° C. for 5 days. Thereafter, the reaction mixture was applied to a Sephadex G-25 column (25 mm ID×600 mm L) equilibrated with 50 mM phosphate buffer (pH 6.0) and development was carried out with the same buffer as used for equilibration at a flow rate of 4 ml/minute. The fractions containing human apelin-36 now free of methionine at the N terminus were pooled. The pooled human apelin-36 fractions were adjusted to pH 6.0 and applied, for adsorption, to a CM-5PW column (7.5 mm ID×75 mm L, Tosoh) equilibrated with 50 mM phosphate buffer+0.1 M NaCl+2.5 M urea (pH 5.0), and stepwise gradient elution was carried out with 0 to 100% B (B=50 mM borate buffer+0.1 M NaCl+2.5 M urea, pH 9.0) at a flow rate of 0.8 ml/minute for 40 minutes. The human apelin-36 fractions were pooled and further applied, for adsorption, to a C4P-50 column (10 mm ID×250 mm L, Showa Denko) equilibrated with 0.1% TFA, and stepwise gradient elution was carried out with 15 to 30% B (B=80% acetonitrile/0.1% TFA) at a flow rate of 2 ml/minute for 40 minutes. The human apelin-36 fractions were pooled and lyophilized to give human apelin-36.

a) Amino Acid Composition Analysis

The amino acid composition was determined using an amino acid analyzer (Hitachi model L-8500A amino acid analyzer). As a result, the amino acid composition was in agreement with that deduced from the nucleotide sequence of the DNA for human apelin-36 (Table 4).

TABLE 4

Amino acid composition analysis

| Amino acid for human apelin-36 | Number of residues per mole | Value predicted by nucleotide sequence |
|---|---|---|
| Asx | 1.0 | 1 |
| Thr[1] | 0 | 0 |
| Ser[1] | 1.8 | 2 |
| Glx | 3.0 | 3 |
| Pro | 5.7 | 6 |
| Gly | 5.6 | 6 |
| Ala | 0 | 0 |
| Cys[2] |  | 0 |
| Val | 1.0 | 1 |
| Met | 1.0 | 1 |
| Ile | 0 | 0 |
| Leu | 2.0 | 2 |
| Tyr | 0 | 0 |
| Phe | 1.8 | 2 |
| His | 1.0 | 1 |
| Lys | 1.8 | 2 |
| Arg | 7.2 | 8 |
| Trp | 0.9 | 1 |

Acid hydrolysis (6N hydrochloric acid-4% thioglycolic acid, 110° C., 24 or 48 hours of hydrolysis)
[1] Value obtained by extrapolation to hour 0.
[2] No detection made.

b) N-Terminal Amino Acid Sequence Analysis

The N-terminal amino acid sequence was determined using a gaseous phase protein sequencer (Applied Biosystems model 477A). As a result, the N-terminal amino acid sequence was in agreement with the sequence deduced from the nucleotide sequence of the DNA for human apelin-36 (Table 5).

TABLE 5

N-terminal amino acid sequence

| Residue No. | PTH[1]-amino acid detected (pmol) | Amino acid deduced from nucleotide sequence for human apelin-36 |
|---|---|---|
| 1 | Leu (570) | Leu |
| 2 | Val (611) | Val |
| 3 | Gln (594) | Gln |
| 4 | Pro (587) | Pro |
| 5 | Arg (332) | Arg |
| 6 | Gly (552) | Gly |
| 7 | Ser (255) | Ser |
| 8 | Arg (277) | Arg |
| 9 | Asn (345) | Asn |
| 10 | Gly (383) | Gly |
| 11 | Pro (383) | Pro |
| 12 | Gly (366) | Gly |
| 13 | Pro (318) | Pro |
| 14 | Trp (131) | Trp |
| 15 | Gln (210) | Gln |
| 16 | Gly (218) | Gly |
| 17 | Gly (281) | Gly |
| 18 | Arg (130) | Arg |
| 19 | Arg (190) | Arg |
| 20 | Lys (144) | Lys |

Analysis was made using 1 nmol.
[1] Phenylthiohydantoin.

c) C-Terminal Amino Acid Analysis

The C-terminal amino acid was analyzed using an amino acid analyzer (Hitachi model L-8500A amino acid analyzer).

TABLE 6

C-terminal amino acid analysis

| human apelin-36 | C-terminal amino acid | Recovery (%) |
|---|---|---|
| | Phe | 66.3 |

Gaseous phase hydrazine decomposition (100° C., 6 hours).

EXAMPLE 40

Biological Activity Assay

The activity assay of the human apelin-36 obtained in Example 39 was performed by the method described in Example 33 and it was confirmed that its activity was equivalent to that of the synthetic product.

INDUSTRIAL APPLICABILITY

The polypeptide of the invention is involved in the modulation of central nervous system function, circulatory function, immune function, gastrointestinal function, metabolic function, reproductive function, etc., it can be used as a drug for treating or preventing a variety of diseases, e.g. HIV infection or AIDS (acquired immune deficiency syndrome) or the like.

SEQUENCE LISTING

```
<160> NUMBER OF SEQ ID NOS: 48

<210> SEQ ID NO 1
<211> LENGTH: 17
<212> TYPE: PRT
<213> ORGANISM: Bovine sp.

<400> SEQUENCE: 1

Leu Val Gln Pro Arg Gly Pro Arg Ser Gly Pro Gly Pro Trp Gln Gly
 1               5                  10                  15

Gly

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (1)..(51)
<223> OTHER INFORMATION: "n" may be a, t, c, g

<400> SEQUENCE: 2
ytngtncarc cnmgnggncc nmgnwsnggn ccnggnccnt ggcarggngg n              51

<210> SEQ ID NO 3
<211> LENGTH: 380
<212> TYPE: PRT
<213> ORGANISM: Homo sapiens

<400> SEQUENCE: 3

Met Glu Glu Gly Gly Asp Phe Asp Asn Tyr Tyr Gly Ala Asp Asn Gln
 1               5                  10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
```

```
                    85                  90                  95
Phe Gly Thr Phe Phe Cys Lys Leu Ser Ser Tyr Leu Ile Phe Val Asn
            100                 105                 110
Met Tyr Ala Ser Val Phe Cys Leu Thr Gly Leu Ser Phe Asp Arg Tyr
            115                 120                 125
Leu Ala Ile Val Arg Pro Val Ala Asn Ala Arg Leu Arg Leu Arg Val
            130                 135                 140
Ser Gly Ala Val Ala Thr Ala Val Leu Trp Val Leu Ala Ala Leu Leu
145                 150                 155                 160
Ala Met Pro Val Met Val Leu Arg Thr Thr Gly Asp Leu Glu Asn Thr
                165                 170                 175
Thr Lys Val Gln Cys Tyr Met Asp Tyr Ser Met Val Ala Thr Val Ser
            180                 185                 190
Ser Glu Trp Ala Trp Glu Val Gly Leu Gly Val Ser Ser Thr Thr Val
            195                 200                 205
Gly Phe Val Val Pro Phe Thr Ile Met Leu Thr Cys Tyr Phe Phe Ile
            210                 215                 220
Ala Gln Thr Ile Ala Gly His Phe Arg Lys Glu Arg Ile Glu Gly Leu
225                 230                 235                 240
Arg Lys Arg Arg Arg Leu Leu Ser Ile Ile Val Val Leu Val Val Thr
                245                 250                 255
Phe Ala Leu Cys Trp Met Pro Tyr His Leu Val Lys Thr Leu Tyr Met
            260                 265                 270
Leu Gly Ser Leu Leu His Trp Pro Cys Asp Phe Asp Leu Phe Leu Met
            275                 280                 285
Asn Ile Phe Pro Tyr Cys Thr Cys Ile Ser Tyr Val Asn Ser Cys Leu
            290                 295                 300
Asn Pro Phe Leu Tyr Ala Phe Phe Asp Pro Arg Phe Arg Gln Ala Cys
305                 310                 315                 320
Thr Ser Met Leu Cys Cys Gly Gln Ser Arg Cys Ala Gly Thr Ser His
                325                 330                 335
Ser Ser Ser Gly Glu Lys Ser Ala Ser Tyr Ser Ser Gly His Ser Gln
            340                 345                 350
Gly Pro Gly Pro Asn Met Gly Lys Gly Gly Glu Gln Met His Glu Lys
            355                 360                 365
Ser Ile Pro Tyr Ser Gln Glu Thr Leu Val Val Asp
            370                 375                 380

<210> SEQ ID NO 4
<211> LENGTH: 1758
<212> TYPE: DNA
<213> ORGANISM: Homo sapiens
<220> FEATURE:
<221> NAME/KEY: CDS
<222> LOCATION: (242)..(1381)

<400> SEQUENCE: 4
gaattccggg ggggtaaggc aagagagggt ggaggaaatt ctgcaggaga caggcttcct      60
ccagggtctg gagaacccag aggcagctcc tcctgagtgc tgggaaggac tctgggcatc     120
ttcagccctt cttactctct gaggctcaag ccagaaattc aggctgcttg cagagtgggt     180
gacagagcca cggagctggt gtccctggga ccctctgccc gtcttctctc cactcccag      240 c atg gag gaa ggt ggt gat ttt gac aac tac tat ggg gca gac aac cag     289
  Met Glu Glu Gly Gly Asp Phe Asp Asn Tyr Tyr Gly Ala Asp Asn Gln
  1               5                   10                  15
```

-continued

| | |
|---|---|
| tct gag tgt gag tac aca gac tgg aaa tcc tcg ggg gcc ctc atc cct<br>Ser Glu Cys Glu Tyr Thr Asp Trp Lys Ser Ser Gly Ala Leu Ile Pro<br>20                          25                            30 | 337 |
| gcc atc tac atg ttg gtc ttc ctc ctg ggc acc acg gga aac ggt ctg<br>Ala Ile Tyr Met Leu Val Phe Leu Leu Gly Thr Thr Gly Asn Gly Leu<br>         35                       40                          45 | 385 |
| gtg ctc tgg acc gtg ttt cgg agc agc cgg gag aag agg cgc tca gct<br>Val Leu Trp Thr Val Phe Arg Ser Ser Arg Glu Lys Arg Arg Ser Ala<br>50                          55                          60 | 433 |
| gat atc ttc att gct agc ctg gcg gtg gct gac ctg acc ttc gtg gtg<br>Asp Ile Phe Ile Ala Ser Leu Ala Val Ala Asp Leu Thr Phe Val Val<br>65                          70                          75                        80 | 481 |
| acg ctg ccc ctg tgg gct acc tac acg tac cgg gac tat gac tgg ccc<br>Thr Leu Pro Leu Trp Ala Thr Tyr Thr Tyr Arg Asp Tyr Asp Trp Pro<br>                     85                          90                          95 | 529 |
| ttt ggg acc ttc ttc tgc aag ctc agc agc tac ctc atc ttc gtc aac<br>Phe Gly Thr Phe Phe Cys Lys Leu Ser Ser Tyr Leu Ile Phe Val Asn<br>                  100                      105                      110 | 577 |
| atg tac gcc agc gtc ttc tgc ctc acc ggc ctc agc ttc gac cgc tac<br>Met Tyr Ala Ser Val Phe Cys Leu Thr Gly Leu Ser Phe Asp Arg Tyr<br>                  115                      120                      125 | 625 |
| ctg gcc atc gtg agg cca gtg gcc aat gct cgg ctg agg ctg cgg gtc<br>Leu Ala Ile Val Arg Pro Val Ala Asn Ala Arg Leu Arg Leu Arg Val<br>130                         135                      140 | 673 |
| agc ggg gcc gtg gcc acg gca gtt ctt tgg gtg ctg gcc gcc ctc ctg<br>Ser Gly Ala Val Ala Thr Ala Val Leu Trp Val Leu Ala Ala Leu Leu<br>145                      150                      155                      160 | 721 |
| gcc atg cct gtc atg gtg tta cgc acc acc ggg gac ttg gag aac acc<br>Ala Met Pro Val Met Val Leu Arg Thr Thr Gly Asp Leu Glu Asn Thr<br>                  165                      170                      175 | 769 |
| act aag gtg cag tgc tac atg gac tac tcc atg gtg gcc act gtg agc<br>Thr Lys Val Gln Cys Tyr Met Asp Tyr Ser Met Val Ala Thr Val Ser<br>180                         185                      190 | 817 |
| tca gag tgg gcc tgg gag gtg ggc ctt ggg gtc tcg tcc acc acc gtg<br>Ser Glu Trp Ala Trp Glu Val Gly Leu Gly Val Ser Ser Thr Thr Val<br>                  195                      200                      205 | 865 |
| ggc ttt gtg gtg ccc ttc acc atc atg ctg acc tgt tac ttc ttc atc<br>Gly Phe Val Val Pro Phe Thr Ile Met Leu Thr Cys Tyr Phe Phe Ile<br>210                         215                      220 | 913 |
| gcc caa acc atc gct ggc cac ttc cgc aag gaa cgc atc gag ggc ctg<br>Ala Gln Thr Ile Ala Gly His Phe Arg Lys Glu Arg Ile Glu Gly Leu<br>225                         230                      235                      240 | 961 |
| cgg aag cgg cgc cgg ctg ctc agc atc atc gtg gtg ctg gtg gtg acc<br>Arg Lys Arg Arg Arg Leu Leu Ser Ile Ile Val Val Leu Val Val Thr<br>                  245                      250                      255 | 1009 |
| ttt gcc ctg tgc tgg atg ccc tac cac ctg gtg aag acg ctg tac atg<br>Phe Ala Leu Cys Trp Met Pro Tyr His Leu Val Lys Thr Leu Tyr Met<br>                  260                      265                      270 | 1057 |
| ctg ggc agc ctg ctg cac tgg ccc tgt gac ttt gac ctc ttc ctc atg<br>Leu Gly Ser Leu Leu His Trp Pro Cys Asp Phe Asp Leu Phe Leu Met<br>                  275                      280                      285 | 1105 |
| aac atc ttc ccc tac tgc acc tgc atc agc tac gtc aac agc tgc ctc<br>Asn Ile Phe Pro Tyr Cys Thr Cys Ile Ser Tyr Val Asn Ser Cys Leu<br>290                         295                      300 | 1153 |
| aac ccc ttc ctc tat gcc ttt ttc gac ccc cgc ttc cgc cag gcc tgc<br>Asn Pro Phe Leu Tyr Ala Phe Phe Asp Pro Arg Phe Arg Gln Ala Cys<br>305                         310                      315                      320 | 1201 |
| acc tcc atg ctc tgc tgt ggc cag agc agg tgc gca ggc acc tcc cac<br>Thr Ser Met Leu Cys Cys Gly Gln Ser Arg Cys Ala Gly Thr Ser His<br>                  325                      330                      335 | 1249 |

| | | | | | | | | | | | | |
|---|---|---|---|---|---|---|---|---|---|---|---|---|
| agc | agc | agt | ggg | gag | aag | tca | gcc | agc | tac | tct | tcg ggg cac agc cag | 1297 |
| Ser | Ser | Ser | Gly | Glu | Lys | Ser | Ala | Ser | Tyr | Ser | Ser Gly His Ser Gln | |
| | | | 340 | | | | 345 | | | | 350 | |
| ggg | ccc | ggc | ccc | aac | atg | ggc | aag | ggt | gga | gaa | cag atg cac gag aaa | 1345 |
| Gly | Pro | Gly | Pro | Asn | Met | Gly | Lys | Gly | Gly | Glu | Gln Met His Glu Lys | |
| | | | 355 | | | | 360 | | | | 365 | |
| tcc | atc | ccc | tac | agc | cag | gag | acc | ctt | gtg | gtt | gac tagggctggg | 1391 |
| Ser | Ile | Pro | Tyr | Ser | Gln | Glu | Thr | Leu | Val | Val | Asp | |
| | | | 370 | | | | 375 | | | | 380 | | agcagagaga agcctggcgc cctcggccct ccccggcctt tgcccttgct ttctgaaaat    1451 caggtagtgt ggctactcct tgtcctatgc acatcctta actgtccct gattctgccc    1511 cgccctgtcc tcctctactg ctttattctt tctcagaggt ttgtggttta ggggaaagag    1571 actgggctct acagacctga ccctgcacaa gccatttaat ctcactcagc ctcagtttct    1631 ccattggtat gaaatggggg aaagtcatat tgatcctaaa atgttgaagc ctgagtctgg    1691 acgcagtaaa agcttgtttc cctctgctgc tttcttagat ctgcaatcgt ctttcctccc    1751 ggaattc    1758

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (20)
<223> OTHER INFORMATION: "n" may be a, t, c, g

<400> SEQUENCE: 5
cgtggscmts stgggcaacn ycctg    25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (1)..(27)
<223> OTHER INFORMATION: "n" may be a, t, c, g

<400> SEQUENCE: 6
gtngwrrggc anccagcaga kggcaaa    27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
cagacaacca gtctgagtgt gagt    24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
atggatttct cgtgcatctg ttct                                              24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
ctggcaggga ggcaggagga a                                                 21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
gcaggaggaa atttcgcaga cagc                                              24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 11
gaagagaatt catctgtgga gta                                               23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 12
accggcaccg ggagggcact t                                                 21

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
gagagtcgcg ggcagagcag cgtcag                                            26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
gaaatcatcc aagtgagggg cgagac                                            26

<210> SEQ ID NO 15
<211> LENGTH: 77
<212> TYPE: PRT
<213> ORGANISM: Mus sp.

<400> SEQUENCE: 15

| Met | Asn | Leu | Arg | Leu | Cys | Val | Gln | Ala | Leu | Leu | Leu | Trp | Leu | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Leu Thr Ala Val Cys Gly Val Pro Leu Met Leu Pro Pro Asp Gly Thr
                20                  25                  30

Gly Leu Glu Glu Gly Ser Met Arg Tyr Leu Val Lys Pro Arg Thr Ser
        35                  40                  45

Arg Thr Gly Pro Gly Ala Trp Gln Gly Gly Arg Arg Lys Phe Arg Arg
    50                  55                  60

Gln Arg Pro Arg Leu Ser His Lys Gly Pro Met Pro Phe
65                  70                  75

```
<210> SEQ ID NO 16
<211> LENGTH: 683
<212> TYPE: DNA
<213> ORGANISM: Mus sp.
<220> FEATURE:
<221> NAME/KEY: CDS
<222> LOCATION: (283)..(513)
```

<400> SEQUENCE: 16

```
ccacttagag agttttttgcc gccgacccga agccaccaag gccagcttcg cggcgctgcc     60
ccgcggcggc agagaaggct gcaccagagc agaggcagcg agcaggagtg gggcaggcag    120
ccagcggtgc ggctggggcg ctcaccctcc cgcggtccgg gagccacgcg agctccgtgc    180
ccgcacgcgc cagccccggc tcgcgccttt ctttgcgtcc gggtgccctg cctctccgcc    240
cactcgccgg ctcctctggg ctgccgcgga ccgagttgca gc atg aat ctg agg       294
                                              Met Asn Leu Arg
                                              1 ctc tgc gtg cag gcg ctg ctg ctg ctc tgg ctc tcc ttg act gca gtt     342
Leu Cys Val Gln Ala Leu Leu Leu Leu Trp Leu Ser Leu Thr Ala Val
    5                   10                  15                  20 tgt gga gtg cca ctg atg ttg cct cca gat gga aca gga cta gaa gaa     390
Cys Gly Val Pro Leu Met Leu Pro Pro Asp Gly Thr Gly Leu Glu Glu
                25                  30                  35 gga agc atg cgc tac ctg gtg aag ccc aga act tcg agg act gga cca     438
Gly Ser Met Arg Tyr Leu Val Lys Pro Arg Thr Ser Arg Thr Gly Pro
            40                  45                  50 gga gcc tgg cag gga ggc agg agg aaa ttt cgc aga cag cgc ccc cgg     486
Gly Ala Trp Gln Gly Gly Arg Arg Lys Phe Arg Arg Gln Arg Pro Arg
        55                  60                  65 ctc tcc cat aag ggc ccc atg cct ttc taaagcagga ttgaagggct            533
Leu Ser His Lys Gly Pro Met Pro Phe
    70                  75 cgccaagtgc cctcccggtg ccggtctctc tactccacag atgaattctc ttctctggaa    593
ccctcacatc tatttggctt tcatcttgca cctgttctag ctgctgatgg tcccggctct    653
tctcacccac caagttcctc taatggcgtg                                     683
```

```
<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer
```

<400> SEQUENCE: 17

```
gaatctgagt ttctgcgtgc aggc                                            24
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
ttagaaaggc atggggccct tatg                                    24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 19
gtagttggga gtcgcgggca gagcac                                  26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 20
tagaaccatg tcaggatcag cacttt                                  26

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 21
agtcgacgca tgaatctgag tttctg                                  26

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22
gagcccttca agctagcttt agaaag                                  26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
gtgccactga tgctgcctcc agatgg                                  26

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Primer

```
<400> SEQUENCE: 24
ttagaaaggc atgggtccct tatg                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
acggcaatgt ccgccacctg gtgc                                          24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
ccctggcagg gaggtcggag gaaa                                          24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 27
gggccgctgg cggcggaatt tcct                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 28
gctgcaccag gtggcggaca ttgc                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 29
ttggcctccg ggcgcccgac ctct                                          24

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 30
gacataaccg cagggggtgg gcacttg                                       27

<210> SEQ ID NO 31
```

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 31
cctgctgctc tggctctgcc tgag                                          24

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 32
ccatcctaat acgactcact atagggc                                       27

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 33
gcggtgtgcg gaggacccct gctg                                          24

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
actcactata gggctcgagc ggc                                           23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 35
ggccgcggcg gcccaaggag cagc                                          24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36
gcgtgtggtg gccccttcgg tcct                                          24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 37
```

```
aatcacaggg ggtgggcgtg tggt                                                24
```

<210> SEQ ID NO 38
<211> LENGTH: 77
<212> TYPE: PRT
<213> ORGANISM: Rattus sp.

<400> SEQUENCE: 38

```
Met Asn Leu Ser Phe Cys Val Gln Ala Leu Leu Leu Leu Trp Leu Ser
  1               5                  10                  15

Leu Thr Ala Val Cys Gly Val Pro Leu Met Leu Pro Pro Asp Gly Lys
             20                  25                  30

Gly Leu Glu Glu Gly Asn Met Arg Tyr Leu Val Lys Pro Arg Thr Ser
         35                  40                  45

Arg Thr Gly Pro Gly Ala Trp Gln Gly Gly Arg Arg Lys Phe Arg Arg
     50                  55                  60

Gln Arg Pro Arg Leu Ser His Lys Gly Pro Met Pro Phe
 65                  70                  75
```

<210> SEQ ID NO 39
<211> LENGTH: 261
<212> TYPE: DNA
<213> ORGANISM: Rattus sp.
<220> FEATURE:
<221> NAME/KEY: CDS
<222> LOCATION: (10)..(240)

<400> SEQUENCE: 39

```
agtcgacgc atg aat ctg agt ttc tgc gtg cag gcg ctg ctg ctg ctc tgg      51
          Met Asn Leu Ser Phe Cys Val Gln Ala Leu Leu Leu Leu Trp
            1               5                  10 ctc tcc ttg act gcc gtg tgt gga gtg cca ctg atg ctg cct cca gat       99
Leu Ser Leu Thr Ala Val Cys Gly Val Pro Leu Met Leu Pro Pro Asp
 15                  20                  25                  30 ggg aaa ggg cta gaa gaa ggc aac atg cgc tac ctg gtg aag ccc aga      147
Gly Lys Gly Leu Glu Glu Gly Asn Met Arg Tyr Leu Val Lys Pro Arg
                 35                  40                  45 act tcg agg act gga cca ggg gcc tgg cag gga ggc agg agg aaa ttt      195
Thr Ser Arg Thr Gly Pro Gly Ala Trp Gln Gly Gly Arg Arg Lys Phe
             50                  55                  60 cgc aga cag cgg ccc cgt ctc tcc cat aag gga ccc atg cct ttc          240
Arg Arg Gln Arg Pro Arg Leu Ser His Lys Gly Pro Met Pro Phe
 65                  70                  75 taaagctagc ttgaagggct c                                              261
```

<210> SEQ ID NO 40
<211> LENGTH: 77
<212> TYPE: PRT
<213> ORGANISM: Homo sapiens

<400> SEQUENCE: 40

```
Met Asn Leu Arg Leu Cys Val Gln Ala Leu Leu Leu Leu Trp Leu Ser
  1               5                  10                  15

Leu Thr Ala Val Cys Gly Gly Ser Leu Met Pro Leu Pro Asp Gly Asn
             20                  25                  30

Gly Leu Glu Asp Gly Asn Val Arg His Leu Val Gln Pro Arg Gly Ser
         35                  40                  45

Arg Asn Gly Pro Gly Pro Trp Gln Gly Gly Arg Arg Lys Phe Arg Arg
     50                  55                  60
```

```
Gln Arg Pro Arg Leu Ser His Lys Gly Pro Met Pro Phe
 65                  70                  75
```

<210> SEQ ID NO 41
<211> LENGTH: 301
<212> TYPE: DNA
<213> ORGANISM: Homo sapiens
<220> FEATURE:
<221> NAME/KEY: CDS
<222> LOCATION: (48)..(278)

<400> SEQUENCE: 41

```
cctcccccgc gccggctcgc cggggccgcg gcggcccaag gagcagc atg aat ctg      56
                                                   Met Asn Leu
                                                    1 cgg ctc tgc gtg cag gcg ctc ctg ctg ctc tgg ctc tcc ttg acc gcg    104
Arg Leu Cys Val Gln Ala Leu Leu Leu Leu Trp Leu Ser Leu Thr Ala
      5                  10                  15 gtg tgt gga ggg tcc ctg atg ccg ctt ccc gat ggg aat ggg ctg gaa    152
Val Cys Gly Gly Ser Leu Met Pro Leu Pro Asp Gly Asn Gly Leu Glu
 20                  25                  30                  35 gac ggc aat gtc cgc cac ctg gtg cag ccc aga ggg tca agg aat ggg    200
Asp Gly Asn Val Arg His Leu Val Gln Pro Arg Gly Ser Arg Asn Gly
                 40                  45                  50 cca ggg ccc tgg cag gga ggt cgg agg aaa ttc cgc gcc cag cgg ccc    248
Pro Gly Pro Trp Gln Gly Gly Arg Arg Lys Phe Arg Ala Gln Arg Pro
             55                  60                  65 cgc ctc tcc cat aag gga ccc atg cct ttc tgaagcagga ctgaaggggc ccc  301
Arg Leu Ser His Lys Gly Pro Met Pro Phe
             70                  75
```

<210> SEQ ID NO 42
<211> LENGTH: 77
<212> TYPE: PRT
<213> ORGANISM: Bovine sp.

<400> SEQUENCE: 42

```
Met Asn Leu Arg Arg Cys Val Gln Ala Leu Leu Leu Leu Trp Leu Cys
 1               5                  10                  15

Leu Ser Ala Val Cys Gly Gly Pro Leu Leu Gln Thr Ser Asp Gly Lys
                 20                  25                  30

Glu Met Glu Glu Gly Thr Ile Arg Tyr Leu Val Gln Pro Arg Gly Pro
             35                  40                  45

Arg Ser Gly Pro Gly Pro Trp Gln Gly Gly Arg Arg Lys Phe Arg Arg
         50                  55                  60

Gln Arg Pro Arg Leu Ser His Lys Gly Pro Met Pro Phe
 65                  70                  75
```

<210> SEQ ID NO 43
<211> LENGTH: 234
<212> TYPE: DNA
<213> ORGANISM: Bovine sp.
<220> FEATURE:
<221> NAME/KEY: CDS
<222> LOCATION: (1)..(231)

<400> SEQUENCE: 43

```
atg aat ctg cgg cgc tgc gtg cag gcg ctc ctg ctg ctc tgg ctc tgc     48
Met Asn Leu Arg Arg Cys Val Gln Ala Leu Leu Leu Leu Trp Leu Cys
 1               5                  10                  15 ctg agc gcg gtg tgc gga gga ccc ctg ctg cag act tct gac ggg aag     96
Leu Ser Ala Val Cys Gly Gly Pro Leu Leu Gln Thr Ser Asp Gly Lys
                 20                  25                  30
```

```
gag atg gaa gaa ggc acc atc cga tac ctg gtg cag ccc agg ggg ccg        144
Glu Met Glu Glu Gly Thr Ile Arg Tyr Leu Val Gln Pro Arg Gly Pro
        35                  40                  45 agg agc ggc cca ggc ccc tgg cag gga ggt cgg agg aag ttc cgg cgc        192
Arg Ser Gly Pro Gly Pro Trp Gln Gly Gly Arg Arg Lys Phe Arg Arg
    50                  55                  60 cag cgg cca cgc ctc tcc cac aag ggt ccc atg cct ttc tga                234
Gln Arg Pro Arg Leu Ser His Lys Gly Pro Met Pro Phe
65                  70                  75

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: pGlu

<400> SEQUENCE: 44

Glu Arg Pro Arg Leu Ser His Lys Gly Pro Met Pro Phe
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Phe Arg Arg Gln Arg Pro Arg Leu Ser His Lys Gly Pro Met Pro
1               5                   10                  15

Phe

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: pGlu

<400> SEQUENCE: 46

Glu Arg Pro Arg Leu Ser His Lys Gly Pro Met Pro
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: pGlu

<400> SEQUENCE: 47

Glu Arg Pro Arg Leu Ser His Lys Gly Pro Met
1               5                   10
```

```
<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Leu Val Gln Pro Arg Gly Ser Arg Asn Gly Pro Gly Pro Trp Gln
 1               5                  10                  15

Gly Gly Arg Arg Lys Phe Arg Arg Gln Arg Pro Arg Leu Ser His Lys
                20                  25                  30

Gly Pro Met Pro Phe
            35
```

The invention claimed is:

1. An isolated DNA comprising a nucleotide sequence coding for a ligand polypeptide capable of binding to a receptor protein, wherein the receptor protein comprises the amino acid sequence of SEQ ID NO: 3, and wherein the ligand polypeptide comprises the amino acid sequence of SEQ ID NO: 40.

2. A recombinant vector which comprises the DNA as claimed in claim 1.

3. A transformant carrying the DNA as claimed in claim 1 or the recombinant vector as claimed in claim 2.

4. A method for producing a polypeptide, a precursor polypeptide thereof or a salt thereof which comprises cultivating the transformant as claimed in claim 3.

* * * * *